United States Patent
Kim et al.

(10) Patent No.: US 10,478,508 B2
(45) Date of Patent: Nov. 19, 2019

(54) COMPOSITIONS, METHODS AND USES FOR ALPHA-1 ANTITRYPSIN FUSION MOLECULES

(71) Applicants: The Regents of the University of Colorado, a body corporate, Denver, CO (US); Konkuk University Industry Cooperation Foundation, Seoul (KR)

(72) Inventors: Soohyun Kim, Greenwood Village (KR); Charles A. Dinarello, Denver, CO (US)

(73) Assignees: The Regents of the University of Colorado, A Body Corporate, Denver, CO (US); Konkuk University Industry Cooperation Foundation, Seoul (KR)

( * ) Notice: Subject to any disclaimer, the term of this patent is extended or adjusted under 35 U.S.C. 154(b) by 473 days.

(21) Appl. No.: 14/370,442

(22) PCT Filed: Jan. 10, 2013

(86) PCT No.: PCT/US2013/021057
§ 371 (c)(1),
(2) Date: Jul. 2, 2014

(87) PCT Pub. No.: WO2013/106589
PCT Pub. Date: Jul. 18, 2013

(65) Prior Publication Data
US 2014/0348859 A1    Nov. 27, 2014

Related U.S. Application Data

(60) Provisional application No. 61/586,038, filed on Jan. 12, 2012, provisional application No. 61/614,391, filed on Mar. 22, 2012, provisional application No. 61/585,182, filed on Jan. 10, 2012.

(51) Int. Cl.
| | |
|---|---|
| *C07K 14/81* | (2006.01) |
| *A61K 38/51* | (2006.01) |
| *C12N 15/62* | (2006.01) |
| *C12N 15/70* | (2006.01) |
| *C12N 15/86* | (2006.01) |
| *A61K 47/68* | (2017.01) |
| *A61K 38/57* | (2006.01) |
| *C12N 15/09* | (2006.01) |

(52) U.S. Cl.
CPC .......... *A61K 47/6803* (2017.08); *A61K 38/57* (2013.01); *A61K 47/6811* (2017.08); *C07K 14/81* (2013.01); *C07K 14/8125* (2013.01); *C07K 2319/30* (2013.01)

(58) Field of Classification Search
None
See application file for complete search history.

(56) References Cited

U.S. PATENT DOCUMENTS

| | | |
|---|---|---|
| 4,021,472 A | 5/1977 | Fujii et al. |
| 4,215,051 A | 7/1980 | Schroeder et al. |
| 4,224,342 A | 9/1980 | Fujii |
| 4,283,418 A | 8/1981 | Fujii et al. |
| 4,522,811 A | 6/1985 | Eppstein et al. |
| 4,629,567 A | 12/1986 | Bollen et al. |
| 4,711,848 A | 12/1987 | Insley et al. |
| 4,829,052 A | 5/1989 | Glover et al. |
| 4,829,054 A | 5/1989 | Emerson et al. |
| 4,857,538 A | 8/1989 | Kashman et al. |
| 4,963,654 A | 10/1990 | Katunuma |
| 5,008,242 A | 4/1991 | Lezdey et al. |
| 5,093,316 A | 3/1992 | Lezdey et al. |
| 5,116,964 A | 5/1992 | Capon et al. |
| 5,134,119 A | 7/1992 | Lezdey et al. |
| 5,134,419 A | 7/1992 | Egashira |
| 5,157,019 A | 10/1992 | Glover |
| 5,175,253 A | 12/1992 | Fallon et al. |
| 5,216,022 A | 6/1993 | Oleksyszyn |
| 5,346,886 A | 9/1994 | Lezdey |
| 5,420,110 A | 5/1995 | Miller |
| 5,455,165 A | 10/1995 | Capon et al. |
| 5,514,582 A | 5/1996 | Capon et al. |
| 5,514,653 A | 5/1996 | Perlmutter |
| 5,604,201 A | 2/1997 | Thomas et al. |

(Continued)

FOREIGN PATENT DOCUMENTS

| | | |
|---|---|---|
| EP | 0511188 B1 | 6/1997 |
| JP | 2002506040 A | 2/2002 |

(Continued)

OTHER PUBLICATIONS

Roitt et al (Immunology, 1985, Gower Medical Publ, London/New York, p. 5.3 at Figure 5.5).*
(Structural Features, Biological Functions of the Alpha-1 Antitrypsin and Contribution to Esophageal Cancer, Squamous Cell Carcinoma. Prof. Xiamoning Li (Ed.), 2012, pp. 281-290, worldwide web at intechopen.com).*
Canfield and Morrison (JEM, 1991, 173: 1483-1491).*
D. J. King, Applications and Engineering of Monoclonal Antibodies, London: Taylor & Francis, 1998, Chapter on Antibody Engineering; Design for Specific Applications; p. 40-41 and Fig. 2.3.

(Continued)

*Primary Examiner* — Michael Szperka
*Assistant Examiner* — Marianne Dibrino
(74) *Attorney, Agent, or Firm* — Polsinelli PC

(57) ABSTRACT

Embodiments herein report compositions of and methods for making and using alpha-1 antitrypsin (AAT) fusion molecules or peptide derivatives thereof. In certain embodiments, compositions and methods relate to generating an AAT fusion molecule of use in pharmaceutically acceptable compositions to treat a subject in need of AAT therapy or treatment. In other embodiments, compositions and methods disclosed herein concern linking AAT or derivative thereof to an immune fragment.

20 Claims, 13 Drawing Sheets

Specification includes a Sequence Listing.

(56) References Cited

U.S. PATENT DOCUMENTS

| | | | |
|---|---|---|---|
| 5,604,281 A | 2/1997 | Kamei et al. |
| 5,610,285 A | 3/1997 | Lebold et al. |
| 5,612,194 A | 3/1997 | Rubin et al. |
| 5,616,693 A | 4/1997 | Hwang et al. |
| 5,686,564 A | 11/1997 | Brundish et al. |
| 5,710,026 A | 1/1998 | Sprecher |
| 5,714,140 A | 2/1998 | Strassmann |
| 5,714,147 A | 2/1998 | Capon et al. |
| 5,734,014 A | 3/1998 | Ishima et al. |
| 5,780,440 A | 7/1998 | Lezdey et al. |
| 5,861,380 A | 1/1999 | Gyorkos et al. |
| 5,869,455 A | 2/1999 | Gyorkos et al. |
| 5,874,424 A | 2/1999 | Batchelor |
| 5,905,023 A | 5/1999 | Sager et al. |
| 5,985,279 A | 11/1999 | Waldmann et al. |
| 6,022,855 A | 2/2000 | Thomas et al. |
| 6,124,257 A | 9/2000 | Lezdey |
| 6,136,834 A | 10/2000 | Ohmoto |
| 6,174,859 B1 | 1/2001 | Lezdey et al. |
| 6,287,817 B1 | 9/2001 | Davis et al. |
| 6,489,308 B1 | 12/2002 | Shapiro |
| 6,797,493 B2 | 9/2004 | Sun et al. |
| 6,849,605 B1 | 2/2005 | Shapiro |
| 6,924,267 B2 | 8/2005 | Daemen et al. |
| 7,034,033 B2 | 4/2006 | Boyce et al. |
| 7,138,370 B2 | 11/2006 | Oiiner et al. |
| 7,850,970 B2 | 12/2010 | Shapiro |
| 8,633,305 B2 * | 1/2014 | Shapiro ............ A61K 31/519 |
| | | | 435/320.1 |
| 2002/0081607 A1 | 6/2002 | Ruben et al. |
| 2003/0040097 A1 | 2/2003 | Ruben et al. |
| 2003/0069395 A1 | 4/2003 | Sato et al. |
| 2003/0073217 A1 | 4/2003 | Barr et al. |
| 2003/0120059 A1 | 6/2003 | Tao et al. |
| 2003/0190311 A1 | 10/2003 | Dall'Acqua et al. |
| 2004/0019022 A1 | 1/2004 | Stec et al. |
| 2004/0220239 A1 | 11/2004 | Shapiro |
| 2004/0220242 A1 | 11/2004 | Shapiro |
| 2004/0254349 A1 | 12/2004 | James et al. |
| 2008/0085854 A1 | 4/2008 | Barr et al. |
| 2008/0199467 A1 | 8/2008 | Mjalli et al. |
| 2008/0261869 A1 | 10/2008 | Shapiro |
| 2009/0203580 A1 | 8/2009 | Dinarello et al. |
| 2009/0298747 A1 | 12/2009 | Shapiro |
| 2010/0061979 A1 | 3/2010 | Blanche et al. |
| 2010/0111940 A1 | 5/2010 | Flier et al. |
| 2011/0020269 A1 | 1/2011 | Strom |
| 2011/0021416 A1 | 1/2011 | Shapiro |
| 2011/0053787 A1 | 3/2011 | Brulliard et al. |
| 2011/0077383 A1 | 3/2011 | Dall'acqua et al. |
| 2014/0341899 A1 | 11/2014 | Dinarello et al. |

FOREIGN PATENT DOCUMENTS

| | | | |
|---|---|---|---|
| JP | 2007504144 A | 3/2007 |
| JP | 2007537992 A | 12/2007 |
| JP | 2010524971 A | 7/2010 |
| WO | 1986000337 A1 | 1/1986 |
| WO | 9206706 A1 | 4/1992 |
| WO | 93018794 A | 9/1993 |
| WO | 95028422 A | 10/1995 |
| WO | 95034538 A | 12/1995 |
| WO | 97021690 A | 6/1997 |
| WO | 9733996 A | 9/1997 |
| WO | WO 98/06248 A2 * | 2/1998 |
| WO | 1998023645 A1 | 6/1998 |
| WO | 1998024806 B1 | 5/1999 |
| WO | 0052034 A | 8/2000 |
| WO | 2000044390 A1 | 8/2000 |
| WO | 0051625 A | 9/2000 |
| WO | 2000052034 A2 | 9/2000 |
| WO | WO0051623 A2 | 9/2000 |
| WO | WO0051624 A2 | 9/2000 |
| WO | WO0103737 A1 | 1/2001 |
| WO | w02002002318 A1 | 1/2002 |
| WO | WO02053092 A2 | 7/2002 |
| WO | WO02060919 A2 | 8/2002 |
| WO | 2002068455 A2 | 9/2002 |
| WO | 020949864 A2 | 11/2002 |
| WO | 2002094864 A2 | 11/2002 |
| WO | 2003021273 A2 | 3/2003 |
| WO | WO03059935 A2 | 7/2003 |
| WO | 03068934 R | 8/2003 |
| WO | 2005019434 A2 | 3/2005 |
| WO | 2005046454 A2 | 5/2005 |
| WO | 2005047337 A1 | 5/2005 |
| WO | 2005112970 A2 | 12/2005 |
| WO | WO2007079312 A2 | 7/2007 |
| WO | 2008033890 A2 | 3/2008 |
| WO | 2008100470 A2 | 8/2008 |
| WO | 0051260 A1 | 9/2008 |
| WO | 2009015345 A1 | 1/2009 |
| WO | 2010123290 A2 | 10/2010 |
| WO | 2011102860 A1 | 8/2011 |
| WO | 2012178102 A2 | 12/2012 |
| WO | 2013003641 A2 | 1/2013 |
| WO | 2013003649 A2 | 1/2013 |

OTHER PUBLICATIONS

AETC Clinical Manual for Management of the HIV-Infected Adult, 2006 Edition, pp. 1-5.

Anderson, Inhibition of HIV-1 gp 160-dependent Membrane Fusion by a Furin-directed Alpha 1-Antitrypsin Variant, The Journal of Biological Chemistry, vol. 268, No. 33 (Nov. 25, 1003), pp. 24887-24891.

Baecher, Allan et al. Human regulatory T cells and their role in autoimmune disease, Immunology Reviews, vol. 212, (2006), pp. 203-216.

Bell, J.J. et al. In Trans T Cell Tolerance Diminishes Autoantibody Responses and Exacerbates Experimental Allergic Encephalomyelitis, The Journal of Immunology, vol. 180 (2008), pp. 1508-1516.

Blanco, et al. Efficacy of alpha1-antitrypsin augmentation therapy in conditions other than pulmonary emphysema. Orphanet Journal of Rare Diseases 2011, 6:14; Abstract.

Bollen A, Herzog A, Cravador A, Herion P, Chuchana P, Vander Straten A, Loriau R, Jacobs P, van Elsen A., "Cloning and expression in *Escherichia coli* of full-length complementary DNA coding for human alpha 1-antitrypsin" DNA. Dec. 1983, 2(4): 255-264. doi:10.1089/dna.1983.2.255.

Bowie et al. (Science, 1990, 247:1306-1310).

Castilla-Llorente C, Martin PJ, McDonald GB, et al. Prognostic factors and outcomes of severe gastrointestinal GVHD after allogeneic hematopoietic cell transplantation. Bone Marrow Transplant. 2014;49:966-971.

Chaiet, Pamela Pam Chaiet Reveals the Latest Tech in the Struggle to Cure Diabetes, The Potomac, Issue 10, (Dec. 14, 2010).

Chan, et al., Alpha-1-antitrypsin (AAT) anomalies are associated with lung disease due to rapidly growing mycobacteria and AAT inhibits *Mycobacterium abscessus* infection of macrophages, Scandinavian Journal of Infectious Diseases, vol. 39 (2007), pp. 690-696.

Dermer, "Another Anniversary for the War on Cancer," Bio/Technology 1994, 12:320.

Dong, VM, et al., Transplantation tolerance: The concept and its applicability; The Pediatric Transplantation, 3, (1999), pp. 181-192.

Eckman et al. In Vitro Transport of Active A1-Antitrypsin to the Apical Surface of Epithelia by Targeting the Polymeric Immunoglobulin Receptor, Am. J. Respir. Cell Mol. Biol., vol. 21; pp. 246-252 (1999).

eMedicineHealth, Anthrax, Apr. 25, 2007, found at www.emedicinehealth.com/script/main/art.asp?articlekey=59372&pf=3&page=7.

European Search Report (Inhibrx) issued in EP Application No. 12804863.4 dated Jul. 16, 2015, 14 pages.

Extended European Search Report and search opinion dated Jul. 16, 2015 for EP 12804863.4.

(56) References Cited

OTHER PUBLICATIONS

Extended European Search Report issued in EP13735645.7, dated Aug. 4, 2015, 13 pages.
Final Office Action issued in U.S. Appl. No. 14/804,132 dated Mar. 6, 2015, 11 pages.
Freshney "Culture of Animal Cells, A Manual of Basic Technique," A.R. Liss, Inc., NY, 1983, p. 4.
Gaur et al., "Effect of nasal immunization with protective antigen of Bacillus anthracis on protective immune response against anthrax toxin," Vaccine 2002, 20:2836-39.
George et al.; An Analysis of Protein Domain Linkers: Their Classification and Role in Protein Folding; Protein Engineering, vol. 15(11), pp. 871-879, Nov. 2003.
Goodnow, Christopher C. Pathways for self-tolerance and the treatment of autoimmune diseases. The Lancet, vol. 357 (Jun. 30, 2001), pp. 2115-2121.
Gooley TA, Chien JW, Pergam SA, et al. Reduced mortality after allogeneic hematopoietic-cell transplantation. N Engl J Med. 2010;363:2091-2101.
Greenspan et al., "Defining epitopes: It's not as easy as it seems," Nature Biotechnology 1999, 17(1):936-37.
Handbook of Targeted Delivery of Imaging Agents. CRC Press, USA, Jan. 1, 1995. pp. 54-55.
Hoppner Clinical Impact of Molecular Diagnostics in Endocrinology (Horm Re. 2002, 58 Suppl. 3:7-15).
Ihse, I., et al. 1876 "Oral trypsin-inhibitor-induced improvement of the exocrine and endocrine pancreatic functions in alloxan diabetic rats," Scandinavian Journal of Gastroenterology, vol. 11, pp. 363-368.
Ikeda, T., et al., 1996, "An inhibition of urinary albumin excretion by protease inhibitor in streptozotocin-diabetic rats," Nephron, vol. 74, No. 4, pp. 709-712.
International Search Report and Written Opinion issued in PCT/US04/27711, dated Jul. 19, 2005. 4 pages.
International Search Report and Written Opinion issued in PCT/US06/22436, dated Feb. 20, 2007, 5 pages.
International Search Report and Written Opinion issued in PCT/US06/61577, dated Jul. 12, 2007, 13 pages.
International Search Report and Written Opinion issued in PCT/US13/21057, dated Jun. 19, 2013, 19 pages.
Janciauskiene et al. (Biochem. Biophys. Res. Comm., 2004, 321:592-600).
Jones TD, Hanlon M, Smith BJ, Heise CT, Nayee PD, Sanders DA, Hamilton A, Sweet C, Unitt E, Alexander G, La KM, Gillies SD, Carr FJ, Baker MP. The development of a modified human IFN-alpha2b linked to the Fc portion of human IgG1 as a novel potential therapeutic for the treatment of hepatitis C virus infection. J Interferon Cytokine Res.
Kamaukhova E, Ophir Y, Golding B. Recombinant human alpha-1 proteinase inhibitor: towards therapeutic use. Amino.
Katsura, M., et al., "Effect of long-term oral administration of trypsin inhibitor on pancreatic exocrine dysfunction in non-insulin dependent diabetes mellitus (NIDDM)", Journal of Pancreas, vol. 7, No. 2, pp. 1-8, 1992, with English translation.
Kinugasa et al. "Neuroglycan C, A Novel Member of the Neuregulin Family" Biochemical and Biophysical Research Communications, vol. 321(4), pp. 1045-1049, Sep. 3, 2004.
Kraus, T.A. et al., Oral tolerance and inflammatory bowel disease, Current Opinion in Gastroenterology, vol. 21 (2005), pp. 692-696.
Kurachi, K., et. al. Cloning and Sequence of cDNA Coding for Alpha 1-Antitrypsin. Proc. Natl. Acad. Sci., 78(11): 5826-6830, Nov. 1981.
Langner KD, Niedrig M, Fultz P, Anderson D, Reiner G, Repke H, Gelderblom H, Seed B, Hilfenhaus J, Zelllmeissl G. Antiviral effects of different CD4-immunoglobulin constructs against HIV-1 and SIV: immunological characterization, pharmacokinetic data and in vivo experiments. Arch Viral. 1993;130(1-2):157-70.
Lee et al. Effect of Recombinant a1- Antitrypsin Fc-Fused (AAT-Fc_Protein on the Inibition of Inflammatory Cytokine Production and Streptozotocin-Induced Diabetes; Molecular Medicine vol. 19, Jan. 1, 2013 pp. 65-71.
Leppla et al., "Development of an improved vaccine for anthrax," J Clin Invest 2002, 109:141-44.
Lewis, Eli C. et al., "Alpha-Antitrypsin Monotherapy Prolongs islet Allograft Survival in Mice", Proceedings of the National Academy of Sciences, National Academy of Sciences US, vol. 102 No. 34, Aug. 2005, 6 pages.
Libert et al. Alpha1-Antitrypsin Inhibits the Lethal Response to TNF in Mice; The Journal of Immunology, 1996, 157: 5123-5129.
Lieberman, J., Augmentation therapy reduces frequency of lung infections in antitrypsin deficiency: a new hypothesis with supporting data, Chest, 2000, vol. 118, No. 5, pp. 1480-1485.
Lomas et al., "Commercial plasma alpha 1-antitrypsin (Prolastin) contains a conformationally inactive, latent component," Eur Respir J. 1997, 10(3):672-675.
Lomas, David A., et al., Preparation and Characterization of Latent alpha-1 antitrypsin. Journal of Biological Chemistry, vol. 270, No. 10, (Mar. 10, 1995) pp. 5282-5288.
Luznik L, O'Donnell PV, Fuchs EJ. Post-transplantation cyclophosphamide for tolerance induction in HLA-haploidentical bone marrow transplantation. Semin Oncol.
MacMillan ML, Robin M, Harris AC, et al. A refined risk score for acute graft-versus-host disease that predicts response to initial therapy, survival, and transplant-related mortality. Biol Blood Marrow Transplant. 2015;21:761-767.
Marcondes AM, Karoopongse E, Lesnikova M, et al. □-1-antitrypsin (ATT)-modified donor cells suppress GVHD but enhance the GVL effect: a role for mitochondrial bioenergetics. Blood. 2014;124:2881-2891.
Marcondes et al. Response of Steroid-Refractory Acute GVHD to A1-Anti-Trypsin ; BBMT Revised MS No. YBBMT-D-15-00664-R2 May 9, 2016 25 pgs.
Market Letter, Sep. 13, 2009, 2 Pages.
Martin PJ, Inamoto Y, Flowers ME, Carpenter PA. Secondary treatment of acute graft- versus-host disease: a critical review. Biol Blood Marrow Transplant. 2012;18:982-988.
Martin PJ, Rizzo JD, Wingard JR, et al. First- and second-line systemic treatment of acute graft-versus-host disease: Recommendations of the American Society of Blood and Marrow Transplantation. Biol Blood Marrow Transplant. 2012;18:1150-1163.
Mast AE, Salvesen G, Schnebli HP, Pizzo SV. Evaluation of the rapid plasma elimination of recombinant alpha 1-proteinase inhibitor: synthesis of polyethylene glycol conjugates with improved therapeutic potential. J Lab Clin Med. 1990; 116(1):58-65.
Michaelsen, et. al. Enhancement of Complement Activation and Cytolysis of Human IgG3 by Deletion of Hinge Exons. Scand. J. Immunol., 32(5):517-528, 1990.
Mohler KM, Torrance DS, Smith CA, Goodwin RG, Stremler KE, Fung VP, Madani H, Widmer MB. Soluble tumor necrosis factor (TNF) receptors are effective therapeutic agents in lethal endotoxemia and function simultaneously as both TNF carriers and TNF antagonists. J Immunol. 1993; 151(3):1548-61.
Musson, J. et al., "Differential Processing of CD4 T-cell epitopes from the protective antigen of Bacillus anthracis," Biol Chem 2003, 278(52): 52425-52431.
Nakamura, N. et al., Effect of trypsin inhibitor on blood sugar, insulin, and glucagon levfels in normal and streptozotocin rats, Journal of the Kyoto Prefecture University of Medicine, vol. 89, No. 6 (1980) pp. 465-470.
Non-Final Office Action issued in U.S. Appl. No. 13/536,976, dated Jan. 31, 2014, 16 pages.
Novak EJ, Blosch CM, Perkins JD, Davis CL, Barr D, McVicar JP, Griffin RS, Farrand AL, Wener M, Marsh CL. Recombinant human tumor necrosis factor receptor Fc fusion protein therapy in kidney transplant recipients undergoing OKT3 induction therapy. Transplantation. 1998; 66(12):1732-5.
Office Action in Ex Parte Reexamination dated Feb. 6, 2015 in connection with U.S. Pat. No. 8,633,305, 15 pages.

(56) References Cited

OTHER PUBLICATIONS

O'Riordan et al. a1-Antitrypsin Deficiency-Associated Panniculitis, Departments of Medicine, Pathology, and Transplantation Surgery, Northwestern University Medical School, vol. 63, No. 3, (1996) pp. 1052-1055.

Palomino, Juan Carlos, New Anti-Tuberculosis Drugs: Strategies, Sources and New Molecules, Current Medicinal Chemistry, vol. 16 (2009) pp. 1898-1904.

Panasyuk, A.V., et al., Disseminated Pulmonary Tuberculosis, Sugar Diabetes, and Amyloidosis in a Patient with Hereditary alpha 1-antitrypsin deficiency. Probl. Tuberk., No. 1, (1988), pp. 72-74.

Powell LM, Pain RH.Effects of glycosylation on the folding and stability of human, recombinant and cleaved alpha 1-antitrypsin. J Mol Bioi. 1992 ;224(1):241-52.

Pozzilli, P. et al., No effect of oral insulin on residual beta-cell function in recent-onset Type 1 diabetes (the IMDIABVII), Diabetologia, vol. 43, (2000) pp. 1000-1004.

Request for Ex Parte Reexamination filed Sep. 19, 2014 in connection with U.S. Pat. No. 8,633,305, 79 pages.

Rothe, Helga, et al., IL-18 Inhibits Diabetes Development in Nonobese Diabetic Mice by Counterregulation of Th1-Dependent Destructive Insulitis, The Journal of Immunology, 163 (1999), pp. 1230-1236.

Rutishauser, U., et. al. Amino Acid Sequence of the Fc Region of a Human Gamma G Immunoglobulin. Proc. Natl. Acad. Sci., 61(4): 1414-1421, Dec. 1968.

Sandborn et al. Etanercept for Active Crohn'S Disease: A Randomized, Double-Blind, Placebo-Controlled Trial.

Schroeder, Rebecca A. et al., Tolerance and the "Holy Grail" of Transplantation, Journal of Surgical Research, vol. 111, (2003) pp. 109-119.

Schwaiblmair M. Vogelmeier C. Alpha 1-antitrypsin. Hope on the horizon for emphysema sufferers? Drugs Aging.

Seo et al. Concerted Regulation of Inhibitory Activity of a1-Antitrypsin by the Native Strain Distributed Throughout the Molecule.

Shapiro et al., "Alpha-1-antitrypsin inhibits human immunodeficiency virus type 1," FASEB J 2001, 15(1):115-122.

Shimoda, Izumi et al., Physiological Characteristics of Spontaneously Developed Diabetes in Male WBGN/Kob Rat and Prevention of Development of Diabetes by Chronic Oral Administration of Synthetic Trypsin Inhibitor (FOY-305), Pancreas, vol. 8, No. 2, (1993) pp. 196-203.

Simpson et al., "Adenoviral augmentation of elafin protects the lung against acute injury mediated by activated neutrophils and bacterial infection," J Immunol , 2001, 167:1778-86.

Skyler, Jay S. et al., Use of Inhaled Insulin in a Basal/Bolus Insulin Regimen in Type 1 Diabetic Subjects, Diabetes Care vol. 28, (2005) pp. 1630-1635.

Song, S. et al. Recombinant Adeno-Associated Virus-Mediated Alpha-1 Antitrypsin Gene Therapy Prevents Type 1 Diabetes in NOD Mice. Gene Therapy (2004) 11:181-186.

Strom, Terry B., Saving islets from allograft rejection, PNAS, vol. 102, No. 36 (2005) pp. 12651-12652.

Subramaniyam, Devipriya et al. C-36 Peptide, a Degradation Product of Alpha1-Antitrypsin, Modulates Human Monocyte Activation Through LPS Signaling Pathways. The International Journal of Biochemistry & Cell Biology 38:563-575, 2006.

Supplementary European Search Report issued in Application No. 04801916.0 dated Aug. 17, 2016, 3 pages.

Tang et al. Interleukin-17 Antagonism Inhibits Acute But Not Chronic Vascular Rejection1; Transplantation, vol. 348-350, Jul. 27, 2001.

Tania Azam et al. "10 Recombinant Alpha-1 Antitrypsan- Fc (AAT-Fc) Inhibits Candida Induced IL 1beta Secretion from Human CD14 Monocytes Comparison to Plasema-Derive AAT and Capase 1 Inhibition" Cytokine vol. 63. 3, Sep. 1, 2013, p. 245.

Tawara, I., et. al. Alpha-1-Antitrypsin Monotherapy Reduces Graft-Versus-Host Disease After Experimental Allogeneic Bone Marrow Transplantation. PNAS, 109(2): 564-569, Jan. 10, 2012.

Tawara, Isao et al., "Alpha-1-Antitrypsin Monotherapy Reduces Graft-Versus-Host Disease After Experimental Allogenic Bone Transplantation", Proceedings of the National Academy of Sciences, Dec. 2011, vol. 109 No. 2, 6 pages.

Travis et al. Isolation and Properties of Recombinant DNA Produced Variants of Human a1-Proteinase Inhibitor: Journal of Biological Chemistry, vol. 260 (7), pp. 4384-4389, Apr. 10, 1985.

UniProt. Accession No. P01857, Jul. 21, 1986, 2 pages.

Vaerman et al. Complexes of albumin and alpha1-antitrypsin with Fc-fragment of IgA monomer are disulfide-bound to penultimate C-terminal cysteine in the Calpha3-domain. Immunology Letters, 1987, 15, pp. 67-72.

Vaerman, et. al. Complexes of Albumin and Alphal-Antitrypsin with Fc-Fragment of IgA Monomer are Disulfide-bound to Penultimate C-Terminal Cysteine in the CAlpha3-Domain. Immunology Letters, 15:67-72, 1987.

van Steenbergen, Acta Clinica Belgica 48.3: 1993:171-189.

Vanhove, et. al. Selective Blockade of CD28 and not CTLA-4 with a Single-Chain Fv-Alpha1-Antitrypsin Fusion Antibody. Blood, 102(2):564-570, Jul. 2003.

Vassar et al. "Beta-Secretase Cleavage of Alzheimer's Amyloid Precursor Protein by the Transmembrane Aspartic Protease Bace" Science, vol. 288 (5440), pp. 735-741, Oct. 22, 1999.

Yang et al (J. Am. Soc. Nephrol. 2003, 14:214-225).

Zamora NP, Pia RV, Del Rio PG, Margaleff RJ, Frias FR, Ronsano JB. Intravenous human plasma-derived augmentation therapy in alpha 1-antitrypsin deficiency: from pharmacokinetic analysis to individualizing therapy. Ann Pharmacother. 2008; 42(5):640-6.

Zettelmeissl G, Gregersen JP, Duport JM, Mehdi S, Reiner G, Seed B. Expression and characterization of human CD4: immunoglobulin fusion proteins. DNA Cell Bioi. 1990; 9(5):347-53.

Aventis Behring. "Alpha1—Proteinase Inhibitor (Human)—Zemaira." Jul. 2003, pp. 1-13.

Carrell Reactive-Centre Variants of Clrantitrypsin. A New Range of Anti-Inflammatory Agents; Biotechnology and Genetic Engineering Reviews, vol. 4, Sep. 1986, pp. 291-310.

Jallat et al. "Modelling alpha antitrypsin function by protein engineering" Journal of Cellular Biochemistry, 1986 Supplement 1OA, p. 274, abstract E111.

Lewis, Eli C. et al. Aplha 1-Antitrypsin Monotherapy Prolongs Islet Allograft Survival in Mice. PNAS, vol. 102, No. 34 (Aug. 23, 2005), pp. 12153-12158.

* cited by examiner

Human AAT (insert) can also be a carboxyterminal fragment of AAT of the last 80 amino acids or less Note: Hinge deletion or mutation: ▭

A.

B.

C.

Time course: Fc-AAT2 pretreatment intraperitoneally before instillation of monosodium urate (MSU) crystals into the knee joint of mouse.

SEQUENCE LISTING

```
<160> NUMBER OF SEQ ID NOS: 58

<210> SEQ ID NO 1
<211> LENGTH: 394
<212> TYPE: PRT
<213> ORGANISM: Homo Sapiens

<400> SEQUENCE: 1

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190
```

-continued

```
Lys Trp Glu Arg Pro Phe Glu Val Lys Asp Thr Glu Glu Asp Phe
            195                 200                 205
His Val Asp Gln Val Thr Thr Val Lys Val Pro Met Met Lys Arg Leu
        210                 215                 220
Gly Met Phe Asn Ile Gln His Cys Lys Lys Leu Ser Ser Trp Val Leu
225                 230                 235                 240
Leu Met Lys Tyr Leu Gly Asn Ala Thr Ala Ile Phe Phe Leu Pro Asp
                245                 250                 255
Glu Gly Lys Leu Gln His Leu Glu Asn Glu Leu Thr His Asp Ile Ile
            260                 265                 270
Thr Lys Phe Leu Glu Asn Glu Asp Arg Arg Ser Ala Ser Leu His Leu
        275                 280                 285
Pro Lys Leu Ser Ile Thr Gly Thr Tyr Asp Leu Lys Ser Val Leu Gly
    290                 295                 300
Gln Leu Gly Ile Thr Lys Val Phe Ser Asn Gly Ala Asp Leu Ser Gly
305                 310                 315                 320
Val Thr Glu Glu Ala Pro Leu Lys Leu Ser Lys Ala Val His Lys Ala
                325                 330                 335
Val Leu Thr Ile Asp Glu Lys Gly Thr Glu Ala Ala Gly Ala Met Phe
            340                 345                 350
Leu Glu Ala Ile Pro Met Ser Ile Pro Pro Glu Val Lys Phe Asn Lys
        355                 360                 365
Pro Phe Val Phe Leu Met Ile Glu Gln Asn Thr Lys Ser Pro Leu Phe
    370                 375                 380
Met Gly Lys Val Val Asn Pro Thr Gln Lys
385                 390

<210> SEQ ID NO 2
<211> LENGTH: 5
<212> TYPE: PRT
<213> ORGANISM: Artificial
<220> FEATURE:
<223> OTHER INFORMATION: synthetic peptide

<400> SEQUENCE: 2

Phe Val Phe Leu Met
1               5

<210> SEQ ID NO 3
<211> LENGTH: 5
<212> TYPE: PRT
<213> ORGANISM: Artificial
<220> FEATURE:
<223> OTHER INFORMATION: synthetic peptide

<400> SEQUENCE: 3

Phe Val Phe Ala Met
1               5

<210> SEQ ID NO 4
<211> LENGTH: 5
<212> TYPE: PRT
<213> ORGANISM: Artificial
<220> FEATURE:
<223> OTHER INFORMATION: synthetic peptide

<400> SEQUENCE: 4

Phe Val Ala Leu Met
1               5
```

```
<210> SEQ ID NO 5
<211> LENGTH: 5
<212> TYPE: PRT
<213> ORGANISM: Artificial
<220> FEATURE:
<223> OTHER INFORMATION: synthetic peptide

<400> SEQUENCE: 5

Phe Val Phe Leu Ala
1               5

<210> SEQ ID NO 6
<211> LENGTH: 5
<212> TYPE: PRT
<213> ORGANISM: Artificial
<220> FEATURE:
<223> OTHER INFORMATION: synthetic peptide

<400> SEQUENCE: 6

Phe Leu Val Phe Ile
1               5

<210> SEQ ID NO 7
<211> LENGTH: 5
<212> TYPE: PRT
<213> ORGANISM: Artificial
<220> FEATURE:
<223> OTHER INFORMATION: synthetic peptide

<400> SEQUENCE: 7

Phe Leu Met Ile Ile
1               5

<210> SEQ ID NO 8
<211> LENGTH: 5
<212> TYPE: PRT
<213> ORGANISM: Artificial
<220> FEATURE:
<223> OTHER INFORMATION: synthetic peptide

<400> SEQUENCE: 8

Phe Leu Phe Val Leu
1               5

<210> SEQ ID NO 9
<211> LENGTH: 5
<212> TYPE: PRT
<213> ORGANISM: Artificial
<220> FEATURE:
<223> OTHER INFORMATION: synthetic peptide

<400> SEQUENCE: 9

Phe Leu Phe Val Val
1               5

<210> SEQ ID NO 10
<211> LENGTH: 5
<212> TYPE: PRT
<213> ORGANISM: Artificial
<220> FEATURE:
<223> OTHER INFORMATION: synthetic peptide

<400> SEQUENCE: 10

Phe Leu Phe Leu Ile
1               5

<210> SEQ ID NO 11
```

```
<211> LENGTH: 5
<212> TYPE: PRT
<213> ORGANISM: Artificial
<220> FEATURE:
<223> OTHER INFORMATION: synthetic peptide

<400> SEQUENCE: 11

Phe Leu Phe Phe Ile
1               5

<210> SEQ ID NO 12
<211> LENGTH: 5
<212> TYPE: PRT
<213> ORGANISM: Artificial
<220> FEATURE:
<223> OTHER INFORMATION: synthetic peptide

<400> SEQUENCE: 12

Phe Leu Met Phe Ile
1               5

<210> SEQ ID NO 13
<211> LENGTH: 5
<212> TYPE: PRT
<213> ORGANISM: Artificial
<220> FEATURE:
<223> OTHER INFORMATION: synthetic peptide

<400> SEQUENCE: 13

Phe Met Leu Leu Ile
1               5

<210> SEQ ID NO 14
<211> LENGTH: 5
<212> TYPE: PRT
<213> ORGANISM: Artificial
<220> FEATURE:
<223> OTHER INFORMATION: synthetic peptide

<400> SEQUENCE: 14

Phe Ile Ile Met Ile
1               5

<210> SEQ ID NO 15
<211> LENGTH: 5
<212> TYPE: PRT
<213> ORGANISM: Artificial
<220> FEATURE:
<223> OTHER INFORMATION: synthetic peptide

<400> SEQUENCE: 15

Phe Leu Phe Cys Ile
1               5

<210> SEQ ID NO 16
<211> LENGTH: 5
<212> TYPE: PRT
<213> ORGANISM: Artificial
<220> FEATURE:
<223> OTHER INFORMATION: synthetic peptide

<400> SEQUENCE: 16

Phe Leu Phe Ala Val
1               5

<210> SEQ ID NO 17
<211> LENGTH: 5
```

```
<212> TYPE: PRT
<213> ORGANISM: Artificial
<220> FEATURE:
<223> OTHER INFORMATION: synthetic peptide

<400> SEQUENCE: 17

Phe Val Tyr Leu Ile
1               5

<210> SEQ ID NO 18
<211> LENGTH: 5
<212> TYPE: PRT
<213> ORGANISM: Artificial
<220> FEATURE:
<223> OTHER INFORMATION: synthetic peptide

<400> SEQUENCE: 18

Phe Ala Phe Leu Met
1               5

<210> SEQ ID NO 19
<211> LENGTH: 5
<212> TYPE: PRT
<213> ORGANISM: Artificial
<220> FEATURE:
<223> OTHER INFORMATION: synthetic peptide

<400> SEQUENCE: 19

Ala Val Phe Leu Met
1               5

<210> SEQ ID NO 20
<211> LENGTH: 10
<212> TYPE: PRT
<213> ORGANISM: Artificial
<220> FEATURE:
<223> OTHER INFORMATION: synthetic peptide

<400> SEQUENCE: 20

Gly Ile Thr Lys Val Phe Ser Asn Gly Ala
1               5                   10

<210> SEQ ID NO 21
<211> LENGTH: 10
<212> TYPE: PRT
<213> ORGANISM: Artificial
<220> FEATURE:
<223> OTHER INFORMATION: synthetic peptide

<400> SEQUENCE: 21

Asp Leu Ser Gly Val Thr Glu Glu Ala Pro
1               5                   10

<210> SEQ ID NO 22
<211> LENGTH: 10
<212> TYPE: PRT
<213> ORGANISM: Artificial
<220> FEATURE:
<223> OTHER INFORMATION: synthetic peptide

<400> SEQUENCE: 22

Leu Lys Leu Ser Lys Ala Val His Lys Ala
1               5                   10

<210> SEQ ID NO 23
<211> LENGTH: 10
<212> TYPE: PRT
```

<213> ORGANISM: Artificial
<220> FEATURE:
<223> OTHER INFORMATION: synthetic peptide

<400> SEQUENCE: 23

Val Leu Thr Ile Asp Glu Lys Gly Thr Glu
1               5                   10

<210> SEQ ID NO 24
<211> LENGTH: 10
<212> TYPE: PRT
<213> ORGANISM: Artificial
<220> FEATURE:
<223> OTHER INFORMATION: synthetic peptide

<400> SEQUENCE: 24

Ala Ala Gly Ala Met Phe Leu Glu Ala Ile
1               5                   10

<210> SEQ ID NO 25
<211> LENGTH: 10
<212> TYPE: PRT
<213> ORGANISM: Artificial
<220> FEATURE:
<223> OTHER INFORMATION: synthetic peptide

<400> SEQUENCE: 25

Pro Met Ser Ile Pro Pro Glu Val Lys Phe
1               5                   10

<210> SEQ ID NO 26
<211> LENGTH: 10
<212> TYPE: PRT
<213> ORGANISM: Artificial
<220> FEATURE:
<223> OTHER INFORMATION: synthetic peptide

<400> SEQUENCE: 26

Asn Lys Pro Phe Val Phe Leu Met Ile Glu
1               5                   10

<210> SEQ ID NO 27
<211> LENGTH: 10
<212> TYPE: PRT
<213> ORGANISM: Artificial
<220> FEATURE:
<223> OTHER INFORMATION: synthetic peptide

<400> SEQUENCE: 27

Gln Asn Thr Lys Ser Pro Leu Phe Met Gly
1               5                   10

<210> SEQ ID NO 28
<211> LENGTH: 8
<212> TYPE: PRT
<213> ORGANISM: Artificial
<220> FEATURE:
<223> OTHER INFORMATION: synthetic peptide

<400> SEQUENCE: 28

Lys Val Val Asn Pro Thr Gln Lys
1               5

<210> SEQ ID NO 29
<211> LENGTH: 22
<212> TYPE: PRT
<213> ORGANISM: Artificial

```
<220> FEATURE:
<223> OTHER INFORMATION: synthetic peptide

<400> SEQUENCE: 29

Leu Glu Ala Ile Pro Met Ser Ile Pro Pro Glu Val Lys Phe Asn Lys
1               5                   10                  15

Pro Phe Val Phe Leu Met
            20

<210> SEQ ID NO 30
<211> LENGTH: 20
<212> TYPE: PRT
<213> ORGANISM: Artificial
<220> FEATURE:
<223> OTHER INFORMATION: Synthetic peptide

<400> SEQUENCE: 30

Leu Glu Ala Ile Pro Met Ser Ile Pro Pro Glu Val Lys Phe Asn Lys
1               5                   10                  15

Pro Phe Val Phe
            20

<210> SEQ ID NO 31
<211> LENGTH: 80
<212> TYPE: PRT
<213> ORGANISM: Artificial
<220> FEATURE:
<223> OTHER INFORMATION: synthetic peptide

<400> SEQUENCE: 31

Gly Ala Asp Leu Ser Gly Val Thr Glu Glu Ala Pro Leu Lys Leu Ser
1               5                   10                  15

Lys Ala Val His Lys Ala Val Leu Thr Ile Asp Glu Lys Gly Thr Glu
                20                  25                  30

Ala Ala Gly Ala Met Phe Leu Glu Ala Ile Pro Met Ser Ile Pro Pro
            35                  40                  45

Glu Val Lys Phe Asn Lys Pro Phe Val Phe Leu Met Ile Glu Gln Asn
        50                  55                  60

Thr Lys Ser Pro Leu Phe Met Gly Lys Val Val Asn Pro Thr Gln Lys
65                  70                  75                  80

<210> SEQ ID NO 32
<211> LENGTH: 652
<212> TYPE: PRT
<213> ORGANISM: Artificial Sequence
<220> FEATURE:
<223> OTHER INFORMATION: FC-AAT fusion polypeptide

<400> SEQUENCE: 32

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95
```

```
His Asp Glu Ile Leu Glu Gly Leu Asn Phe Asn Leu Thr Glu Ile Pro
            100                 105                 110
Glu Ala Gln Ile His Glu Gly Phe Gln Glu Leu Leu Arg Thr Leu Asn
        115                 120                 125
Gln Pro Asp Ser Gln Leu Gln Leu Thr Thr Gly Asn Gly Leu Phe Leu
    130                 135                 140
Ser Glu Gly Leu Lys Leu Val Asp Lys Phe Leu Glu Asp Val Lys Lys
145                 150                 155                 160
Leu Tyr His Ser Glu Ala Phe Thr Val Asn Phe Gly Asp Thr Glu Glu
                165                 170                 175
Ala Lys Lys Gln Ile Asn Asp Tyr Val Glu Lys Gly Thr Gln Gly Lys
            180                 185                 190
Ile Val Asp Leu Val Lys Glu Leu Asp Arg Asp Thr Val Phe Ala Leu
        195                 200                 205
Val Asn Tyr Ile Phe Phe Lys Gly Lys Trp Glu Arg Pro Phe Glu Val
    210                 215                 220
Lys Asp Thr Glu Glu Glu Asp Phe His Val Asp Gln Ala Thr Thr Val
225                 230                 235                 240
Lys Val Pro Met Met Lys Arg Leu Gly Met Phe Asn Ile Gln His Cys
                245                 250                 255
Lys Lys Leu Ser Ser Trp Val Leu Leu Met Lys Tyr Leu Gly Asn Ala
            260                 265                 270
Thr Ala Ile Phe Phe Leu Pro Asp Glu Gly Lys Leu Gln His Leu Glu
        275                 280                 285
Asn Glu Leu Thr His Asp Ile Ile Thr Lys Phe Leu Glu Asn Glu Asp
    290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Glu Ala Pro Leu Lys
            340                 345                 350
Leu Ser Lys Ala Val His Lys Ala Val Leu Thr Ile Asp Glu Lys Gly
        355                 360                 365
Thr Glu Ala Ala Gly Ala Met Phe Leu Glu Ala Ile Pro Met Ser Ile
    370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys Thr Arg Glu Pro Lys Ser Cys Asp Lys Thr His Thr Cys Pro
            420                 425                 430
Pro Cys Pro Ala Pro Glu Leu Leu Gly Gly Pro Ser Val Phe Leu Phe
        435                 440                 445
Pro Pro Lys Pro Lys Asp Thr Leu Met Ile Ser Arg Thr Pro Glu Val
    450                 455                 460
Thr Cys Val Val Val Asp Val Ser His Glu Asp Pro Glu Val Lys Phe
465                 470                 475                 480
Asn Trp Tyr Val Asp Gly Val Glu Val His Asn Ala Lys Thr Lys Pro
                485                 490                 495
Arg Glu Glu Gln Tyr Asn Ser Thr Tyr Arg Val Val Ser Val Leu Thr
            500                 505                 510
```

```
Val Leu His Gln Asp Trp Leu Asn Gly Lys Glu Tyr Lys Cys Lys Val
            515                 520                 525

Ser Asn Lys Ala Leu Pro Ala Pro Ile Glu Lys Thr Ile Ser Lys Ala
530                 535                 540

Lys Gly Gln Pro Arg Glu Pro Gln Val Tyr Thr Leu Pro Pro Ser Arg
545                 550                 555                 560

Asp Glu Leu Thr Lys Asn Gln Val Ser Leu Thr Cys Leu Val Lys Gly
            565                 570                 575

Phe Tyr Pro Ser Asp Ile Ala Val Glu Trp Glu Ser Asn Gly Gln Pro
            580                 585                 590

Glu Asn Asn Tyr Lys Thr Thr Pro Pro Val Leu Asp Ser Asp Gly Ser
            595                 600                 605

Phe Phe Leu Tyr Ser Lys Leu Thr Val Asp Lys Ser Arg Trp Gln Gln
610                 615                 620

Gly Asn Val Phe Ser Cys Ser Val Met His Glu Ala Leu His Asn His
625                 630                 635                 640

Tyr Thr Gln Lys Ser Leu Ser Leu Ser Pro Gly Lys
            645                 650

<210> SEQ ID NO 33
<211> LENGTH: 394
<212> TYPE: PRT
<213> ORGANISM: Homo Sapiens

<400> SEQUENCE: 33

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Ala Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240
```

```
Leu Met Lys Tyr Leu Gly Asn Ala Thr Ala Ile Phe Phe Leu Pro Asp
                245                 250                 255
Glu Gly Lys Leu Gln His Leu Glu Asn Glu Leu Thr His Asp Ile Ile
            260                 265                 270
Thr Lys Phe Leu Glu Asn Glu Asp Arg Arg Ser Ala Ser Leu His Leu
        275                 280                 285
Pro Lys Leu Ser Ile Thr Gly Thr Tyr Asp Leu Lys Ser Val Leu Gly
    290                 295                 300
Gln Leu Gly Ile Thr Lys Val Phe Ser Asn Gly Ala Asp Leu Ser Gly
305                 310                 315                 320
Val Thr Glu Glu Ala Pro Leu Lys Leu Ser Lys Ala Val His Lys Ala
                325                 330                 335
Val Leu Thr Ile Asp Glu Lys Gly Thr Glu Ala Ala Gly Ala Met Phe
            340                 345                 350
Leu Glu Ala Ile Pro Met Ser Ile Pro Pro Glu Val Lys Phe Asn Lys
        355                 360                 365
Pro Phe Val Phe Leu Met Ile Glu Gln Asn Thr Lys Ser Pro Leu Phe
    370                 375                 380
Met Gly Lys Val Val Asn Pro Thr Gln Lys
385                 390

<210> SEQ ID NO 34
<211> LENGTH: 36
<212> TYPE: PRT
<213> ORGANISM: Artificial
<220> FEATURE:
<223> OTHER INFORMATION: synthetic peptide

<400> SEQUENCE: 34

Ser Ile Pro Pro Glu Val Lys Phe Asn Lys Pro Phe Val Phe Leu Met
1               5                   10                  15
Ile Glu Gln Asn Thr Lys Ser Pro Leu Phe Met Gly Lys Val Val Asn
            20                  25                  30
Pro Thr Gln Lys
        35

<210> SEQ ID NO 35
<211> LENGTH: 62
<212> TYPE: DNA
<213> ORGANISM: Homo sapiens

<400> SEQUENCE: 35
tttagaggcc atacccatgt ctatcccccc cgaggtcaag ttcaacaaac cctttgtct       60 tt                                                                    62

<210> SEQ ID NO 36
<211> LENGTH: 62
<212> TYPE: DNA
<213> ORGANISM: Artificial Sequence
<220> FEATURE:
<223> OTHER INFORMATION: mutant

<400> SEQUENCE: 36
tttagaggcc atatgcatgt ctatcccccc cgaggtcaag ttcaacaaac cctttgtct       60 tt                                                                    62

<210> SEQ ID NO 37
<211> LENGTH: 9
```

```
<212> TYPE: PRT
<213> ORGANISM: Homo sapiens

<400> SEQUENCE: 37

Ala Ile Pro Arg Ser Ile Pro Pro Glu
1               5

<210> SEQ ID NO 38
<211> LENGTH: 9
<212> TYPE: PRT
<213> ORGANISM: Artificial Sequence
<220> FEATURE:
<223> OTHER INFORMATION: synthetic peptide

<400> SEQUENCE: 38

Ala Ile Pro Val Ser Ile Pro Pro Glu
1               5

<210> SEQ ID NO 39
<211> LENGTH: 9
<212> TYPE: PRT
<213> ORGANISM: Artificial Sequence
<220> FEATURE:
<223> OTHER INFORMATION: syntehtic peptide

<400> SEQUENCE: 39

Ala Ile Pro Val Ser Ile Pro Pro Glu
1               5

<210> SEQ ID NO 40
<211> LENGTH: 9
<212> TYPE: PRT
<213> ORGANISM: Artificial Sequence
<220> FEATURE:
<223> OTHER INFORMATION: synthetic peptide

<400> SEQUENCE: 40

Ala Ile Pro Leu Ser Ile Pro Pro Glu
1               5

<210> SEQ ID NO 41
<211> LENGTH: 9
<212> TYPE: PRT
<213> ORGANISM: Artificial Sequence
<220> FEATURE:
<223> OTHER INFORMATION: synthetic peptide

<400> SEQUENCE: 41

Ala Ile Cys Met Ser Ile Pro Pro Glu
1               5

<210> SEQ ID NO 42
<211> LENGTH: 9
<212> TYPE: PRT
<213> ORGANISM: Artificial Sequence
<220> FEATURE:
<223> OTHER INFORMATION: syntehtic peptide

<400> SEQUENCE: 42

Ala Ile Pro Ala Ser Ile Pro Pro Glu
1               5

<210> SEQ ID NO 43
<211> LENGTH: 9
<212> TYPE: PRT
<213> ORGANISM: Artificial Sequence
<220> FEATURE:
```

<223> OTHER INFORMATION: synthetic peptide

<400> SEQUENCE: 43

Ala Ile Pro Met Ser Ile Pro Pro Lys
1               5

<210> SEQ ID NO 44
<211> LENGTH: 9
<212> TYPE: PRT
<213> ORGANISM: Artificial Sequence
<220> FEATURE:
<223> OTHER INFORMATION: synthetic peptide

<400> SEQUENCE: 44

Ala Ala Gly Arg Ser Leu Asn Pro Glu
1               5

<210> SEQ ID NO 45
<211> LENGTH: 9
<212> TYPE: PRT
<213> ORGANISM: Artificial Sequence
<220> FEATURE:
<223> OTHER INFORMATION: synthetic peptide

<400> SEQUENCE: 45

Ile Ala Gly Arg Ser Leu Asn Pro Asn
1               5

<210> SEQ ID NO 46
<211> LENGTH: 9
<212> TYPE: PRT
<213> ORGANISM: Artificial Sequence
<220> FEATURE:
<223> OTHER INFORMATION: synthetic peptide

<400> SEQUENCE: 46

Ile Ala Gly Arg Leu Leu Asn Pro Asn
1               5

<210> SEQ ID NO 47
<211> LENGTH: 1977
<212> TYPE: DNA
<213> ORGANISM: Artificial Sequence
<220> FEATURE:
<223> OTHER INFORMATION: derived from human alpha-1 antitrypsin and
      human Fc fragment of IgG1

<400> SEQUENCE: 47

```
gaattcgcca ccatgccgtc ttctgtctcg tggggcatcc tcctgctggc aggcctgtgc    60
tgcctggtcc ctgtctccct ggctgaggat ccccagggag atgctgccca agacacagat   120 acatccacc acgatcagga tcacccaacc ttcaacaaga tcaccccaa cctggctgag    180 ttcgccttca gcctataccg ccagctggca caccagtcca acagcaccaa tatcttcttc   240
tccccagtga gcatcgctac agcctttgca atgctctccc tggggaccaa ggctgacact   300
cacgatgaaa tcctggaggg cctgaatttc aacctcacgg agattccgga ggctcagatc   360
catgaaggct tccaggaact cctccgtacc ctcaaccagc cagacagcca gctccagctg   420
accaccggca tggcctgtt cctcagcgag ggctgaagc tagtggataa gttttggag    480 gatgttaaaa agttgtacca ctcagaagcc ttcactgtca acttcgggga caccgaagag   540
gccaagaaac agatcaacga ttacgtggag aagggtactc aagggaaaat tgtggatttg   600
gtcaaggagc ttgacagaga cacagttttt gctctggtga attacatctt ctttaaaggc   660
```

| | |
|---|---|
| aaatgggaga gaccctttga agtcaaggac accgaggaag aggacttcca cgtggaccag | 720 |
| gcgaccaccg tgaaggtgcc tatgatgaag cgtttaggca tgtttaacat ccagcactgt | 780 |
| aagaagctgt ccagctgggt gctgctgatg aaatacctgg gcaatgccac cgccatcttc | 840 |
| ttcctgcctg atgaggggaa actacagcac ctggaaaatg aactcaccca cgatatcatc | 900 |
| accaagttcc tggaaaatga agacagaagg tctgccagct acatttacc caaactgtcc | 960 |
| attactggaa cctatgatct gaagagcgtc ctgggtcaac tgggcatcac taaggtcttc | 1020 |
| agcaatgggg ctgacctctc cggggtcaca gaggaggcac ccctgaagct ctccaaggcc | 1080 |
| gtgcataagg ctgtgctgac catcgacgag aaagggactg aagctgctgg ggccatgttt | 1140 |
| ttagaggcca tacccatgtc tatccccccc gaggtcaagt tcaacaaacc ctttgtcttc | 1200 |
| ttaatgattg aacaaaatac caagtctccc ctcttcatgg aaaagtggt gaatcccacc | 1260 |
| caaaaaacgc gtgagcccaa atcttgtgac aaaactcaca catgcccacc gtgcccagca | 1320 |
| cctgaactcc tggggggacc gtcagtcttc ctcttccccc caaaacccaa ggacaccctc | 1380 |
| atgatctccc ggaccctga ggtcacatgc gtggtggtgg acgtgagcca cgaagaccct | 1440 |
| gaggtcaagt tcaactggta cgtggacggc gtggaggtgc ataatgccaa gacaaagccg | 1500 |
| cgggaggagc agtacaacag cacgtaccgt gtggtcagcg tcctcaccgt cctgcaccag | 1560 |
| gactggctga atggcaagga gtacaagtgc aaggtctcca acaaagccct cccagccccc | 1620 |
| atcgagaaaa ccatctccaa agccaaaggg cagccccgag aaccacaggt gtacaccctg | 1680 |
| cccccatccc gggatgagct gaccaagaac caggtcagcc tgacctgcct ggtcaaaggc | 1740 |
| ttctatccca gcgacatcgc cgtggagtgg gagagcaatg ggcagccgga gaacaactac | 1800 |
| aagaccacgc ctcccgtgct ggactccgac ggctccttct tcctctacag caagctcacc | 1860 |
| gtggacaaga gcaggtggca gcaggggaac gtcttctcat gctccgtgat gcatgaggct | 1920 |
| ctgcacaacc actacacgca gaagagcctc tccctgtctc cgggtaaatg aggatct | 1977 |

<210> SEQ ID NO 48
<211> LENGTH: 1950
<212> TYPE: DNA
<213> ORGANISM: Artificial Sequence
<220> FEATURE:
<223> OTHER INFORMATION: Artificial: derived from human alpha-1
      antitrypsin and human Fc fragment of IgG1 with hinge deletion

<400> SEQUENCE: 48

| | |
|---|---|
| gaattcgcca ccatgccgtc ttctgtctcg tggggcatcc tcctgctggc aggcctgtgc | 60 |
| tgcctggtcc ctgtctccct ggctgaggat ccccagggga tgctgcccca agacacagat | 120 |
| acatcccacc acgatcagga tcacccaacc ttcaacaaga tcaccccaa cctggctgag | 180 |
| ttcgccttca gcctataccg ccagctggca caccagtcca acagcaccaa tatcttcttc | 240 |
| tccccagtga gcatcgctac agccttgca atgctctccc tggggaccaa ggctgacact | 300 |
| cacgatgaaa tcctggaggg cctgaatttc aacctcacgg agattccgga ggctcagatc | 360 |
| catgaaggct tccaggaact cctccgtacc ctcaaccagc cagacagcca gctccagctg | 420 |
| accaccggca atggcctgtt cctcagcgag ggcctgaagc tagtggataa gttttttggag | 480 |
| gatgttaaaa agttgtacca ctcagaagcc ttcactgtca acttcgggga caccgaagag | 540 |
| gccaagaaac agatcaacga ttacgtggag aagggtactc aagggaaaat tgtggatttg | 600 |
| gtcaaggagc ttgacagaga cacagttttt gctctggtga attacatctt ctttaaaggc | 660 |
| aaatgggaga gaccctttga agtcaaggac accgaggaag aggacttcca cgtggaccag | 720 |

```
gcgaccaccg tgaaggtgcc tatgatgaag cgtttaggca tgtttaacat ccagcactgt    780
aagaagctgt ccagctgggt gctgctgatg aaatacctgg caatgccac cgccatcttc    840 ttcctgcctg atgagggaa actacagcac ctggaaaatg aactcaccca cgatatcatc    900
accaagttcc tggaaaatga agacagaagg tctgccagct acatttacc caaactgtcc    960 attactggaa cctatgatct gaagagcgtc ctgggtcaac tgggcatcac taaggtcttc   1020
agcaatgggg ctgacctctc cggggtcaca gaggaggcac ccctgaagct ctccaaggcc   1080
gtgcataagg ctgtgctgac catcgacgag aaagggactg aagctgctgg ggccatgttt   1140
ttagaggcca tacccatgtc tatcccccc gaggtcaagt tcaacaaacc ctttgtcttc    1200
ttaatgattg aacaaaatac caagtctccc ctcttcatgg aaaagtggt gaatcccacc    1260 caaaaaacgc gtacatgccc accgtgccca gcacctgaac tcctgggggg accgtcagtc   1320
ttcctcttcc ccccaaaacc caaggacacc ctcatgatct cccggacccc tgaggtcaca   1380
tgcgtggtgg tggacgtgag ccacgaagac cctgaggtca agttcaactg gtacgtggac   1440
ggcgtggagg tgcataatgc caagacaaag ccgcgggagg agcagtacaa cagcacgtac   1500
cgtgtggtca gcgtcctcac cgtcctgcac caggactggc tgaatggcaa ggagtacaag   1560
tgcaaggtct ccaacaaagc cctcccagcc cccatcgaga aaaccatctc caaagccaaa   1620
gggcagcccc gagaaccaca ggtgtacacc ctgcccccat cccgggatga gctgaccaag   1680
aaccaggtca gcctgacctg cctggtcaaa ggcttctatc ccagcgacat cgccgtggag   1740
tgggagagca atgggcagcc ggagaacaac tacaagacca cgcctcccgt gctggactcc   1800
gacggctcct tcttcctcta cagcaagctc accgtggaca agagcaggtg gcagcagggg   1860
aacgtcttct catgctccgt gatgcatgag gctctgcaca accactacac gcagaagagc   1920 ctctcccctgt ctccgggtaa atgaggatct                                    1950
```

<210> SEQ ID NO 49
<211> LENGTH: 643
<212> TYPE: PRT
<213> ORGANISM: Artificial Sequence
<220> FEATURE:
<223> OTHER INFORMATION: derived from human alpha-1 antitrypsin and
      human Fc fragment of IgG1

<400> SEQUENCE: 49

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140
```

```
Ser Glu Gly Leu Lys Leu Val Asp Lys Phe Leu Asp Val Lys Lys
145                 150                 155                 160

Leu Tyr His Ser Glu Ala Phe Thr Val Asn Phe Gly Asp Thr Glu Glu
        165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Thr Arg Thr Cys Pro Pro Cys Pro Ala Pro Glu Leu Leu Gly
            420                 425                 430

Gly Pro Ser Val Phe Leu Phe Pro Pro Lys Pro Lys Asp Thr Leu Met
        435                 440                 445

Ile Ser Arg Thr Pro Glu Val Thr Cys Val Val Val Asp Val Ser His
    450                 455                 460

Glu Asp Pro Glu Val Lys Phe Asn Trp Tyr Val Asp Gly Val Glu Val
465                 470                 475                 480

His Asn Ala Lys Thr Lys Pro Arg Glu Glu Gln Tyr Asn Ser Thr Tyr
                485                 490                 495

Arg Val Val Ser Val Leu Thr Val Leu His Gln Asp Trp Leu Asn Gly
            500                 505                 510

Lys Glu Tyr Lys Cys Lys Val Ser Asn Lys Ala Leu Pro Ala Pro Ile
        515                 520                 525

Glu Lys Thr Ile Ser Lys Ala Lys Gly Gln Pro Arg Glu Pro Gln Val
    530                 535                 540

Tyr Thr Leu Pro Pro Ser Arg Asp Glu Leu Thr Lys Asn Gln Val Ser
545                 550                 555                 560
```

| | | | | | | | | | | | | |
|---|---|---|---|---|---|---|---|---|---|---|---|---|
|Leu|Thr|Cys|Leu|Val|Lys|Gly|Phe|Tyr|Pro|Ser|Asp|Ile|Ala|Val|Glu|
| | | | |565| | | |570| | | |575|

| | | | | | | | | | | | |
|---|---|---|---|---|---|---|---|---|---|---|---|
|Trp|Glu|Ser|Asn|Gly|Gln|Pro|Glu|Asn|Asn|Tyr|Lys|Thr|Thr|Pro|Pro|
| | | |580| | | |585| | | |590|

| | | | | | | | | | | | |
|---|---|---|---|---|---|---|---|---|---|---|---|
|Val|Leu|Asp|Ser|Asp|Gly|Ser|Phe|Phe|Leu|Tyr|Ser|Lys|Leu|Thr|Val|
| | |595| | | |600| | | |605|

| | | | | | | | | | | | |
|---|---|---|---|---|---|---|---|---|---|---|---|
|Asp|Lys|Ser|Arg|Trp|Gln|Gln|Gly|Asn|Val|Phe|Ser|Cys|Ser|Val|Met|
| |610| | | |615| | | |620|

| | | | | | | | | | | | |
|---|---|---|---|---|---|---|---|---|---|---|---|
|His|Glu|Ala|Leu|His|Asn|His|Tyr|Thr|Gln|Lys|Ser|Leu|Ser|Leu|Ser|
|625| | | |630| | | |635| | | |640|

Pro Gly Lys

<210> SEQ ID NO 50
<211> LENGTH: 1962
<212> TYPE: DNA
<213> ORGANISM: Artificial Sequence
<220> FEATURE:
<223> OTHER INFORMATION: derived from human alpha-1 antitrypsin and human Fc fragment of IgG2

<400> SEQUENCE: 50

```
gaattcgcca ccatgccgtc ttctgtctcg tggggcatcc tcctgctggc aggcctgtgc      60
tgcctggtcc ctgtctccct ggctgaggat ccccagggag atgctgccca agaacagat      120
acatcccacc acgatcagga tcacccaacc ttcaacaaga tcaccccca cctggctgag      180
ttcgccttca gcctataccg ccagctggca caccagtcca acagcaccaa tatcttcttc      240
tccccagtga gcatcgctac agcctttgca atgctctccc tggggaccaa ggctgacact      300
cacgatgaaa tcctggaggg cctgaatttc aacctcacgg agattccgga ggctcagatc      360
catgaaggct tccaggaact cctccgtacc ctcaaccagc cagacagcca gctccagctg      420
accaccggca atggcctgtt cctcagcgag ggcctgaagc tagtggataa gtttttggag      480
gatgttaaaa agttgtacca ctcagaagcc ttcactgtca acttcgggga caccgaagag      540
gccaagaaac agatcaacga ttacgtggag aagggtactc aagggaaaat tgtggatttg      600
gtcaaggagc ttgacagaga cacagttttt gctctggtga attacatctt ctttaaaggc      660
aaatgggaga gaccctttga agtcaaggac accgaggaag aggacttcca cgtggaccag      720
gcgaccaccg tgaaggtgcc tatgatgaag cgtttaggca tgtttaacat ccagcactgt      780
aagaagctgt ccagctgggt gctgctgatg aaatacctgg gcaatgccac cgccatcttc      840
ttcctgcctg atgagggaa actacagcac ctggaaaatg aactcaccca cgatatcatc      900
accaagttcc tggaaaatga agacagaagg tctgccagct acatttacc caaactgtcc      960
attactggaa cctatgatct gaagagcgtc ctgggtcaac tggcatcac taaggtcttc     1020
agcaatgggg ctgacctctc cggggtcaca gaggaggcac ccctgaagct ctccaaggcc     1080
gtgcataagg ctgtgctgac catcgacgag aaagggactg aagctgctgg ggccatgttt     1140
ttagaggcca tacccatgtc tatccccccc gaggtcaagt tcaacaaacc ctttgtcttc     1200
ttaatgattg aacaaaatac caagtctccc ctcttcatgg gaaaagtggt gaatcccacc     1260
caaaaaacgc gtcgcaaatg ttgtgtcgag tgcccaccgt gcccagcacc acctgtggca     1320
ggaccgtcag tcttcctctt ccccccaaaa cccaaggaca ccctcatgat ctcccggacc     1380
cctgaggtca catgcgtggt ggtggacgtg agccacgaag accctgaggt caagttcaac     1440
tggtacgtgg acggcgtgga ggtgcataat gccaagacaa agccgcggga ggagcagtac     1500
aacagcacgt accgtgtggt cagcgtcctc accgtcctgc accaggactg gctgaatggc     1560
```

-continued

```
aaggagtaca agtgcaaggt ctccaacaaa gccctcccag ccccatcga gaaaaccatc    1620 tccaaagcca aagggcagcc ccgagaacca caggtgtaca ccctgccccc atcccgggat    1680
gagctgacca agaaccaggt cagcctgacc tgcctggtca aaggcttcta tcccagcgac    1740
atcgccgtgg agtgggagag caatgggcag ccggagaaca actacaagac cacgcctccc    1800
gtgctggact ccgacggctc cttcttcctc tacagcaagc tcaccgtgga caagagcagg    1860
tggcagcagg ggaacgtctt ctcatgctcc gtgatgcatg aggctctgca caaccactac    1920
acgcagaaga gcctctccct gtctccgggt aaatgaggat ct                      1962
```

<210> SEQ ID NO 51
<211> LENGTH: 647
<212> TYPE: PRT
<213> ORGANISM: Artificial Sequence
<220> FEATURE:
<223> OTHER INFORMATION: derived from human alpha-1 antitrypsin and
      human Fc fragment of IgG2

<400> SEQUENCE: 51

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285
```

```
Asn Glu Leu Thr His Asp Ile Ile Thr Lys Phe Leu Glu Asn Glu Asp
        290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
                340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Thr Arg Arg Lys Cys Cys Val Glu Cys Pro Pro Cys Pro Ala
                420                 425                 430

Pro Pro Val Ala Gly Pro Ser Val Phe Leu Phe Pro Pro Lys Pro Lys
            435                 440                 445

Asp Thr Leu Met Ile Ser Arg Thr Pro Glu Val Thr Cys Val Val Val
450                 455                 460

Asp Val Ser His Glu Asp Pro Glu Val Lys Phe Asn Trp Tyr Val Asp
465                 470                 475                 480

Gly Val Glu Val His Asn Ala Lys Thr Lys Pro Arg Glu Glu Gln Tyr
                485                 490                 495

Asn Ser Thr Tyr Arg Val Val Ser Val Leu Thr Val Leu His Gln Asp
                500                 505                 510

Trp Leu Asn Gly Lys Glu Tyr Lys Cys Lys Val Ser Asn Lys Ala Leu
            515                 520                 525

Pro Ala Pro Ile Glu Lys Thr Ile Ser Lys Ala Lys Gly Gln Pro Arg
530                 535                 540

Glu Pro Gln Val Tyr Thr Leu Pro Pro Ser Arg Asp Glu Leu Thr Lys
545                 550                 555                 560

Asn Gln Val Ser Leu Thr Cys Leu Val Lys Gly Phe Tyr Pro Ser Asp
                565                 570                 575

Ile Ala Val Glu Trp Glu Ser Asn Gly Gln Pro Glu Asn Asn Tyr Lys
                580                 585                 590

Thr Thr Pro Pro Val Leu Asp Ser Asp Gly Ser Phe Phe Leu Tyr Ser
            595                 600                 605

Lys Leu Thr Val Asp Lys Ser Arg Trp Gln Gln Gly Asn Val Phe Ser
610                 615                 620

Cys Ser Val Met His Glu Ala Leu His Asn His Tyr Thr Gln Lys Ser
625                 630                 635                 640

Leu Ser Leu Ser Pro Gly Lys
                645

<210> SEQ ID NO 52
<211> LENGTH: 1995
<212> TYPE: DNA
<213> ORGANISM: Artificial Sequence
<220> FEATURE:
<223> OTHER INFORMATION: derived from human alpha-1 antitrypsin and
      human Fc fragment of IgG3
```

<400> SEQUENCE: 52

```
gaattcgcca ccatgccgtc ttctgtctcg tggggcatcc tcctgctggc aggcctgtgc      60
tgcctggtcc ctgtctccct ggctgaggat ccccagggag atgctgccca agacagat      120
acatcccacc acgatcagga tcacccaacc ttcaacaaga tcaccccaa cctggctgag      180
ttcgccttca gcctataccg ccagctggca caccagtcca acagcaccaa tatcttcttc      240
tccccagtga gcatcgctac agcctttgca atgctctccc tggggaccaa ggctgacact      300
cacgatgaaa tcctggaggg cctgaatttc aacctcacgg agattccgga ggctcagatc      360
catgaaggct tccaggaact cctccgtacc ctcaaccagc cagacagcca gctccagctg      420
accaccggca atggcctgtt cctcagcgag ggcctgaagc tagtggataa gttttttggag      480
gatgttaaaa agttgtacca ctcagaagcc ttcactgtca acttcgggga caccgaagag      540
gccaagaaac agatcaacga ttacgtggag aagggtactc aagggaaaat tgtggatttg      600
gtcaaggagc ttgacagaga cacagttttt gctctggtga attacatctt ctttaaaggc      660
aaatgggaga gacccttgga agtcaaggac accgaggaag aggacttcca cgtggaccag      720
gcgaccaccg tgaaggtgcc tatgatgaag cgtttaggca tgtttaacat ccagcactgt      780
aagaagctgt ccagctgggt gctgctgatg aaatacctgg gcaatgccac cgccatcttc      840
ttcctgcctg atgaggggaa actacagcac ctggaaaatg aactcaccca cgatatcatc      900
accaagttcc tggaaaatga agacagaagg tctgccagct acatttacc caaactgtcc      960
attactggaa cctatgatct gaagagcgtc ctgggtcaac tgggcatcac taaggtcttc     1020
agcaatgggg ctgacctctc cggggtcaca gaggaggcac ccctgaagct ctccaaggcc     1080
gtgcataagg ctgtgctgac catcgacgag aaagggactg aagctgctgg ggccatgttt     1140
ttagaggcca tacccatgtc tatccccccc gaggtcaagt tcaacaaacc ctttgtcttc     1200
ttaatgattg aacaaaatac caagtctccc ctcttcatgg gaaaagtggt gaatcccacc     1260
caaaaaacgc gtccatgccc acggtgccca gagcccaaat cttgtgacac acctcccccg     1320
tgcccaaggt gcccagcacc tgaactcctg ggggaccgt cagtcttcct cttccccccca     1380
aaacccaagg acaccctcat gatctccccgg acccctgagg tcacatgcgt ggtggtggac     1440
gtgagccacg aagaccctga ggtcaagttc aactggtacg tggacggcgt ggaggtgcat     1500
aatgccaaga caaagccgcg ggaggagcag tacaacagca cgtaccgtgt ggtcagcgtc     1560
ctcaccgtcc tgcaccagga ctggctgaat ggcaaggagt acaagtgcaa ggtctccaac     1620
aaagccctcc cagcccccat cgagaaaacc atctccaaag ccaaagggca gccccgagaa     1680
ccacaggtgt acaccctgcc cccatcccgg gatgagctga ccaagaacca ggtcagcctg     1740
acctgcctgg tcaaaggctt ctatcccagc gacatcgccg tggagtggga gagcaatggg     1800
cagccggaga acaactacaa gaccacgcct cccgtgctgg actccgacgg ctccttcttc     1860
ctctacagca agctcaccgt ggacaagagc aggtggcagc aggggaacgt cttctcatgc     1920
tccgtgatgc atgaggctct gcacaaccac tacacgcaga gagcctctc cctgtctccg     1980
ggtaaatgag gatct                                                     1995
```

<210> SEQ ID NO 53
<211> LENGTH: 658
<212> TYPE: PRT
<213> ORGANISM: Artificial Sequence
<220> FEATURE:
<223> OTHER INFORMATION: derived from human alpha-1 antitrypsin and human Fc fragment of IgG3

<400> SEQUENCE: 53

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415
```

Gln Lys Thr Arg Pro Cys Pro Arg Cys Pro Glu Pro Lys Ser Cys Asp
                420                 425                 430

Thr Pro Pro Pro Cys Pro Arg Cys Pro Ala Pro Glu Leu Leu Gly Gly
                435                 440                 445

Pro Ser Val Phe Leu Phe Pro Lys Pro Lys Asp Thr Leu Met Ile
450                 455                 460

Ser Arg Thr Pro Glu Val Thr Cys Val Val Val Asp Val Ser His Glu
465                 470                 475                 480

Asp Pro Glu Val Lys Phe Asn Trp Tyr Val Asp Gly Val Glu Val His
                485                 490                 495

Asn Ala Lys Thr Lys Pro Arg Glu Glu Gln Tyr Asn Ser Thr Tyr Arg
                500                 505                 510

Val Val Ser Val Leu Thr Val Leu His Gln Asp Trp Leu Asn Gly Lys
                515                 520                 525

Glu Tyr Lys Cys Lys Val Ser Asn Lys Ala Leu Pro Ala Pro Ile Glu
            530                 535                 540

Lys Thr Ile Ser Lys Ala Lys Gly Gln Pro Arg Glu Pro Gln Val Tyr
545                 550                 555                 560

Thr Leu Pro Pro Ser Arg Asp Glu Leu Thr Lys Asn Gln Val Ser Leu
                565                 570                 575

Thr Cys Leu Val Lys Gly Phe Tyr Pro Ser Asp Ile Ala Val Glu Trp
                580                 585                 590

Glu Ser Asn Gly Gln Pro Glu Asn Asn Tyr Lys Thr Thr Pro Pro Val
            595                 600                 605

Leu Asp Ser Asp Gly Ser Phe Phe Leu Tyr Ser Lys Leu Thr Val Asp
610                 615                 620

Lys Ser Arg Trp Gln Gln Gly Asn Val Phe Ser Cys Ser Val Met His
625                 630                 635                 640

Glu Ala Leu His Asn His Tyr Thr Gln Lys Ser Leu Ser Leu Ser Pro
                645                 650                 655

Gly Lys

<210> SEQ ID NO 54
<211> LENGTH: 1965
<212> TYPE: DNA
<213> ORGANISM: Artificial Sequence
<220> FEATURE:
<223> OTHER INFORMATION: derived from human alpha-1 antitrypsin and
      human Fc fragment of IgG4

<400> SEQUENCE: 54
gaattcgcca ccatgccgtc ttctgtctcg tggggcatcc tcctgctggc aggcctgtgc     60
tgcctggtcc ctgtctccct ggctgaggat ccccagggag atgctgccca agaagacagat   120 acatcccacc acgatcagga tcacccaacc ttcaacaaga tcacccccaa cctggctgag   180
ttcgccttca gcctataccg ccagctggca caccagtcca acagcaccaa tatcttcttc   240
tccccagtga gcatcgctac agccttttgca atgctctccc tggggaccaa ggctgacact   300
cacgatgaaa tcctggaggg cctgaatttc aacctcacgg agattccgga ggctcagatc   360
catgaaggct tccaggaact cctccgtacc ctcaaccagc cagacagcca gctccagctg   420
accaccggca atggcctgtt cctcagcgag ggcctgaagc tagtggataa gttttttggag   480 gatgttaaaa agttgtacca ctcagaagcc ttcactgtca acttcgggga caccgaagag   540
gccaagaaac agatcaacga ttacgtggag aagggtactc aagggaaaat tgtggatttg   600

```
gtcaaggagc ttgacagaga cacagttttt gctctggtga attacatctt ctttaaaggc      660
aaatgggaga gaccctttga agtcaaggac accgaggaag aggacttcca cgtggaccag      720
gcgaccaccg tgaaggtgcc tatgatgaag cgtttaggca tgtttaacat ccagcactgt      780
aagaagctgt ccagctgggt gctgctgatg aaatacctgg gcaatgccac cgccatcttc      840
ttcctgcctg atgaggggaa actacagcac ctggaaaatg aactcaccca cgatatcatc      900
accaagttcc tggaaaatga agacagaagg tctgccagct acatttaccc aaactgtcc       960 attactggaa cctatgatct gaagagcgtc ctgggtcaac tgggcatcac taaggtcttc      1020
agcaatgggg ctgacctctc cggggtcaca gaggaggcac ccctgaagct ctccaaggcc     1080
gtgcataagg ctgtgctgac catcgacgag aaagggactg aagctgctgg ggccatgttt     1140
ttagaggcca tacccatgtc tatccccccc gaggtcaagt tcaacaaacc ctttgtcttc     1200
ttaatgattg aacaaaatac caagtctccc ctcttcatgg gaaaagtggt gaatcccacc     1260 caaaaacgc gttccaaata tggtccccca tgcccatcat gcccagcacc tgagttcctg      1320
gggggaccgt cagtcttcct cttccccca aacccaagg acaccctcat gatctcccgg       1380
acccctgagg tcacatgcgt ggtggtggac gtgagccacg aagaccctga ggtcaagttc     1440
aactggtacg tggacggcgt ggaggtgcat aatgccaaga caaagccgcg ggaggagcag    1500
tacaacagca cgtaccgtgt ggtcagcgtc ctcaccgtcc tgcaccagga ctggctgaat     1560
ggcaaggagt acaagtgcaa ggtctccaac aaagccctcc cagcccccat cgagaaaacc    1620
atctccaaag ccaaagggca gccccgagaa ccacaggtgt acaccctgcc cccatcccgg     1680
gatgagctga ccaagaacca ggtcagcctg acctgcctgg tcaaaggctt ctatcccagc     1740
gacatcgccg tggagtggga gagcaatggg cagccggaga caactacaa gaccacgcct      1800 cccgtgctgg actccgacgg ctccttcttc ctctacagca agctcaccgt ggacaagagc    1860
aggtggcagc aggggaacgt cttctcatgc tccgtgatgc atgaggctct gcacaaccac    1920
tacacgcaga agagcctctc cctgtctccg ggtaaatgag gatct                     1965
```

<210> SEQ ID NO 55
<211> LENGTH: 648
<212> TYPE: PRT
<213> ORGANISM: Artificial Sequence
<220> FEATURE:
<223> OTHER INFORMATION: derived from human alpha-1 antitrypsin and
      human Fc fragment of IgG4

<400> SEQUENCE: 55

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
```

```
            115                 120                 125
Gln Pro Asp Ser Gln Leu Gln Leu Thr Thr Gly Asn Gly Leu Phe Leu
130                 135                 140
Ser Glu Gly Leu Lys Leu Val Asp Lys Phe Leu Glu Asp Val Lys Lys
145                 150                 155                 160
Leu Tyr His Ser Glu Ala Phe Thr Val Asn Phe Gly Asp Thr Glu Glu
            165                 170                 175
Ala Lys Lys Gln Ile Asn Asp Tyr Val Glu Lys Gly Thr Gln Gly Lys
            180                 185                 190
Ile Val Asp Leu Val Lys Glu Leu Asp Arg Asp Thr Val Phe Ala Leu
            195                 200                 205
Val Asn Tyr Ile Phe Phe Lys Gly Lys Trp Glu Arg Pro Phe Glu Val
210                 215                 220
Lys Asp Thr Glu Glu Glu Asp Phe His Val Asp Gln Ala Thr Thr Val
225                 230                 235                 240
Lys Val Pro Met Met Lys Arg Leu Gly Met Phe Asn Ile Gln His Cys
            245                 250                 255
Lys Lys Leu Ser Ser Trp Val Leu Leu Met Lys Tyr Leu Gly Asn Ala
            260                 265                 270
Thr Ala Ile Phe Phe Leu Pro Asp Glu Gly Lys Leu Gln His Leu Glu
            275                 280                 285
Asn Glu Leu Thr His Asp Ile Ile Thr Lys Phe Leu Glu Asn Glu Asp
290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
            325                 330                 335
Ser Asn Gly Ala Asp Leu Ser Gly Val Thr Glu Glu Ala Pro Leu Lys
            340                 345                 350
Leu Ser Lys Ala Val His Lys Ala Val Leu Thr Ile Asp Glu Lys Gly
            355                 360                 365
Thr Glu Ala Ala Gly Ala Met Phe Leu Glu Ala Ile Pro Met Ser Ile
370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
            405                 410                 415
Gln Lys Thr Arg Ser Lys Tyr Gly Pro Pro Cys Pro Ser Cys Pro Ala
            420                 425                 430
Pro Glu Phe Leu Gly Gly Pro Ser Val Phe Leu Phe Pro Pro Lys Pro
            435                 440                 445
Lys Asp Thr Leu Met Ile Ser Arg Thr Pro Glu Val Thr Cys Val Val
            450                 455                 460
Val Asp Val Ser His Glu Asp Pro Glu Val Lys Phe Asn Trp Tyr Val
465                 470                 475                 480
Asp Gly Val Glu Val His Asn Ala Lys Thr Lys Pro Arg Glu Glu Gln
            485                 490                 495
Tyr Asn Ser Thr Tyr Arg Val Val Ser Val Leu Thr Val Leu His Gln
            500                 505                 510
Asp Trp Leu Asn Gly Lys Glu Tyr Lys Cys Lys Val Ser Asn Lys Ala
            515                 520                 525
Leu Pro Ala Pro Ile Glu Lys Thr Ile Ser Lys Ala Lys Gly Gln Pro
530                 535                 540
```

Arg Glu Pro Gln Val Tyr Thr Leu Pro Pro Ser Arg Asp Glu Leu Thr
545                 550                 555                 560

Lys Asn Gln Val Ser Leu Thr Cys Leu Val Lys Gly Phe Tyr Pro Ser
                565                 570                 575

Asp Ile Ala Val Glu Trp Glu Ser Asn Gly Gln Pro Glu Asn Asn Tyr
            580                 585                 590

Lys Thr Thr Pro Pro Val Leu Asp Ser Asp Gly Ser Phe Phe Leu Tyr
        595                 600                 605

Ser Lys Leu Thr Val Asp Lys Ser Arg Trp Gln Gln Gly Asn Val Phe
610                 615                 620

Ser Cys Ser Val Met His Glu Ala Leu His Asn His Tyr Thr Gln Lys
625                 630                 635                 640

Ser Leu Ser Leu Ser Pro Gly Lys
                645

<210> SEQ ID NO 56
<211> LENGTH: 634
<212> TYPE: PRT
<213> ORGANISM: Artificial Sequence
<220> FEATURE:
<223> OTHER INFORMATION: derived from human alpha-1 antitrypsin and
      human Fc fragment of IgG2 with hinge deletion

<400> SEQUENCE: 56

Met Pro Ser Ser Val Ser Trp Gly Ile Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys 245                 250                 255
Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Thr Arg Pro Val Ala Gly Pro Ser Val Phe Leu Phe Pro Pro
            420                 425                 430

Lys Pro Lys Asp Thr Leu Met Ile Ser Arg Thr Pro Glu Val Thr Cys
        435                 440                 445

Val Val Val Asp Val Ser His Glu Asp Pro Glu Val Lys Phe Asn Trp
    450                 455                 460

Tyr Val Asp Gly Val Glu Val His Asn Ala Lys Thr Lys Pro Arg Glu
465                 470                 475                 480

Glu Gln Tyr Asn Ser Thr Tyr Arg Val Val Ser Val Leu Thr Val Leu
                485                 490                 495

His Gln Asp Trp Leu Asn Gly Lys Glu Tyr Lys Cys Lys Val Ser Asn
            500                 505                 510

Lys Ala Leu Pro Ala Pro Ile Glu Lys Thr Ile Ser Lys Ala Lys Gly
        515                 520                 525

Gln Pro Arg Glu Pro Gln Val Tyr Thr Leu Pro Pro Ser Arg Asp Glu
    530                 535                 540

Leu Thr Lys Asn Gln Val Ser Leu Thr Cys Leu Val Lys Gly Phe Tyr
545                 550                 555                 560

Pro Ser Asp Ile Ala Val Glu Trp Glu Ser Asn Gly Gln Pro Glu Asn
                565                 570                 575

Asn Tyr Lys Thr Thr Pro Pro Val Leu Asp Ser Asp Gly Ser Phe Phe
            580                 585                 590

Leu Tyr Ser Lys Leu Thr Val Asp Lys Ser Arg Trp Gln Gln Gly Asn
        595                 600                 605

Val Phe Ser Cys Ser Val Met His Glu Ala Leu His Asn His Tyr Thr
    610                 615                 620

Gln Lys Ser Leu Ser Leu Ser Pro Gly Lys
625                 630

<210> SEQ ID NO 57
<211> LENGTH: 632
<212> TYPE: PRT
<213> ORGANISM: Artificial Sequence -continued
<220> FEATURE:
<223> OTHER INFORMATION: derived from human alpha-1 antitrypsin and
      human Fc fragment of IgG3 with hinge deletion)

<400> SEQUENCE: 57

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
```

```
                385                 390                 395                 400
        Gln Asn Thr Lys Ser Pro Leu Phe Met Gly Lys Val Val Asn Pro Thr
                        405                 410                 415

Gln Lys Thr Arg Gly Gly Pro Ser Val Phe Leu Phe Pro Pro Lys Pro
                        420                 425                 430

Lys Asp Thr Leu Met Ile Ser Arg Thr Pro Glu Val Thr Cys Val Val
                        435                 440                 445

Val Asp Val Ser His Glu Asp Pro Glu Val Lys Phe Asn Trp Tyr Val
                450                 455                 460

Asp Gly Val Glu Val His Asn Ala Lys Thr Lys Pro Arg Glu Glu Gln
        465                 470                 475                 480

Tyr Asn Ser Thr Tyr Arg Val Val Ser Val Leu Thr Val Leu His Gln
                        485                 490                 495

Asp Trp Leu Asn Gly Lys Glu Tyr Lys Cys Lys Val Ser Asn Lys Ala
                        500                 505                 510

Leu Pro Ala Pro Ile Glu Lys Thr Ile Ser Lys Ala Lys Gly Gln Pro
                        515                 520                 525

Arg Glu Pro Gln Val Tyr Thr Leu Pro Pro Ser Arg Asp Glu Leu Thr
                530                 535                 540

Lys Asn Gln Val Ser Leu Thr Cys Leu Val Lys Gly Phe Tyr Pro Ser
        545                 550                 555                 560

Asp Ile Ala Val Glu Trp Glu Ser Asn Gly Gln Pro Glu Asn Asn Tyr
                        565                 570                 575

Lys Thr Thr Pro Pro Val Leu Asp Ser Asp Gly Ser Phe Phe Leu Tyr
                        580                 585                 590

Ser Lys Leu Thr Val Asp Lys Ser Arg Trp Gln Gln Gly Asn Val Phe
                        595                 600                 605

Ser Cys Ser Val Met His Glu Ala Leu His Asn His Tyr Thr Gln Lys
                        610                 615                 620

Ser Leu Ser Leu Ser Pro Gly Lys
        625                 630

<210> SEQ ID NO 58
<211> LENGTH: 632
<212> TYPE: PRT
<213> ORGANISM: Artificial Sequence
<220> FEATURE:
<223> OTHER INFORMATION: derived from human alpha-1 antitrypsin and
      human Fc fragment of IgG4 with hinge deletion

<400> SEQUENCE: 58

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
                35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
                100                 105                 110
```

-continued

```
Glu Ala Gln Ile His Glu Gly Phe Gln Glu Leu Leu Arg Thr Leu Asn
            115                 120                 125
Gln Pro Asp Ser Gln Leu Gln Leu Thr Thr Gly Asn Gly Leu Phe Leu
130                 135                 140
Ser Glu Gly Leu Lys Leu Val Asp Lys Phe Leu Glu Asp Val Lys Lys
145                 150                 155                 160
Leu Tyr His Ser Glu Ala Phe Thr Val Asn Phe Gly Asp Thr Glu Glu
                165                 170                 175
Ala Lys Lys Gln Ile Asn Asp Tyr Val Glu Lys Gly Thr Gln Gly Lys
            180                 185                 190
Ile Val Asp Leu Val Lys Glu Leu Asp Arg Asp Thr Val Phe Ala Leu
        195                 200                 205
Val Asn Tyr Ile Phe Phe Lys Gly Lys Trp Glu Arg Pro Phe Glu Val
    210                 215                 220
Lys Asp Thr Glu Glu Asp Phe His Val Asp Gln Ala Thr Thr Val
225                 230                 235                 240
Lys Val Pro Met Met Lys Arg Leu Gly Met Phe Asn Ile Gln His Cys
                245                 250                 255
Lys Lys Leu Ser Ser Trp Val Leu Leu Met Lys Tyr Leu Gly Asn Ala
            260                 265                 270
Thr Ala Ile Phe Phe Leu Pro Asp Glu Gly Lys Leu Gln His Leu Glu
        275                 280                 285
Asn Glu Leu Thr His Asp Ile Ile Thr Lys Phe Leu Glu Asn Glu Asp
    290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Glu Ala Pro Leu Lys
            340                 345                 350
Leu Ser Lys Ala Val His Lys Ala Val Leu Thr Ile Asp Glu Lys Gly
        355                 360                 365
Thr Glu Ala Ala Gly Ala Met Phe Leu Glu Ala Ile Pro Met Ser Ile
    370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys Thr Arg Gly Gly Pro Ser Val Phe Leu Phe Pro Pro Lys Pro
            420                 425                 430
Lys Asp Thr Leu Met Ile Ser Arg Thr Pro Glu Val Thr Cys Val Val
        435                 440                 445
Val Asp Val Ser His Glu Asp Pro Glu Val Lys Phe Asn Trp Tyr Val
    450                 455                 460
Asp Gly Val Glu Val His Asn Ala Lys Thr Lys Pro Arg Glu Glu Gln
465                 470                 475                 480
Tyr Asn Ser Thr Tyr Arg Val Val Ser Val Leu Thr Val Leu His Gln
                485                 490                 495
Asp Trp Leu Asn Gly Lys Glu Tyr Lys Cys Lys Val Ser Asn Lys Ala
            500                 505                 510
Leu Pro Ala Pro Ile Glu Lys Thr Ile Ser Lys Ala Lys Gly Gln Pro
        515                 520                 525
Arg Glu Pro Gln Val Tyr Thr Leu Pro Pro Ser Arg Asp Glu Leu Thr
```

-continued

```
            530                 535                 540
Lys Asn Gln Val Ser Leu Thr Cys Leu Val Lys Gly Phe Tyr Pro Ser
545                 550                 555                 560

Asp Ile Ala Val Glu Trp Glu Ser Asn Gly Gln Pro Glu Asn Asn Tyr
                565                 570                 575

Lys Thr Thr Pro Pro Val Leu Asp Ser Asp Gly Ser Phe Phe Leu Tyr
            580                 585                 590

Ser Lys Leu Thr Val Asp Lys Ser Arg Trp Gln Gln Gly Asn Val Phe
        595                 600                 605

Ser Cys Ser Val Met His Glu Ala Leu His Asn His Tyr Thr Gln Lys
    610                 615                 620

Ser Leu Ser Leu Ser Pro Gly Lys
625                 630
```

COMPOSITIONS, METHODS AND USES FOR ALPHA-1 ANTITRYPSIN FUSION MOLECULES

PRIORITY

This application claims the benefit of U.S. Provisional Patent Application Ser. No. 61/614,391, filed on Mar. 22, 2012, U.S. Provisional Patent Application Ser. No. 61/586,038, filed on Jan. 12, 2012, and U.S. Provisional Patent Application Ser. No. 61/585,182, filed on Jan. 10, 2012, and International Application No. PCT/US13/21057 filed Jan. 10, 2013, all of which are incorporated herein by reference in their entirety for all purposes.

FIELD

Embodiments herein relate to compositions, methods and uses for recombinant alpha-1 antitrypsin (α-1 antitrypsin, AAT). In certain embodiments, recombinant AAT disclosed herein can be isolated more readily than other forms of AAT. In other embodiments, recombinant AAT has enhanced anti-inflammatory and anti-immune activities compared to naturally-occurring AAT or other commercial formulations of AAT. In yet other embodiments, 10-fold, 100 fold or even 1000 fold less recombinant AAT (rAAT) or AAT fusion molecules may be used in the place of any and all current forms of AAT for prevention or treatment of a condition or disease in a subject. In some embodiments, AAT fusion molecules can be used to treat a subject having a condition such as an infection or other health condition. Yet other embodiments reported herein concern compositions and methods for treating a myocardial indication, diabetes, inflammatory bowel disease, graft rejection or other known AAT-responsive conditions.

BACKGROUND

AAT

Normal plasma concentration of alpha-1 antitrypsin (AAT) ranges from 1.3 to 3.5 mg/ml. Under certain conditions, AAT easily diffuses into tissue spaces and forms a 1:1 complex with target proteases, principally neutrophil elastase. Other enzymes such as trypsin, chymotrypsin, cathepsin G, plasmin, thrombin, tissue kallikrein, and factor Xa can also serve as substrates. The enzyme/inhibitor complex is then removed from circulation by binding to serpin-enzyme complex (SEC) receptor and catabolized by the liver and spleen.

SUMMARY

Embodiments herein report generating and using recombinant constructs of alpha-1 antitrypsin (AAT) having superior properties to commercially available AAT compositions. Other embodiments report methods for purifying and scaling-up recombinant AAT production for therapeutic uses. In accordance with these embodiments, recombinant AAT can be isolated for use for any AAT-related activity, for example, as an anti-inflammatory agent, an immune modulator and/or a serine protease inhibitor.

In certain embodiments, recombinant AAT disclosed herein includes a full length molecule or carboxyterminal peptide derivative thereof generated by any recombinant technology known in the art. Some embodiments concern constructs including AAT or a carboxyterminal derivative thereof having immunological elements associated with AAT, for example, to use for rapid purification and activity conservation of the AAT or to increase activity of AAT or its peptides. Other embodiments concern simultaneous synthesis of more than one constructs having AAT molecules each associated with an immunological element (e.g. an Fc fragment) and co-purified as a unit. Other embodiments can concern generating a construct of one or more carboxyterminal derivative(s) or fragment(s) of AAT including, for example, a fragment of the last 80 AAs or subfragments thereof (e.g. about 40, about 30, about 20 or about 10 AAs, or about 5 AAs) of the molecule associated with one or more immune molecule to form a construct for compositions, methods and uses disclosed herein.

An AAT molecule of a construct contemplated herein can concern naturally occurring alpha-1 antitrypsin (e.g. human) or the most abundant form of AAT or other naturally-occurring form thereof, or fragments, or derivatives thereof, or mutant forms of AAT having no significant serine protease inhibitor activity, or alleles thereof (for example, there are approximately 100 naturally occurring AAT variants and any of these variants can be used in constructs disclosed herein), or analogs thereof or fusion protein thereof (e.g. a human IgG or fragment of human IgG). In accordance with these embodiments, a final construct may include 2 AAT constructs each associated with an immunological fragment (e.g. an Fc fragment) wherein the AAT-immune fragment constructs are linked together by disulfide bonds to form dual AAT-immune fragment constructs joined by one or more disulfide bonds (See for example, FIG. 1 and FIG. 2). In certain methods disclosed herein, rapid purification of AAT- or AAT-peptide linked to an immune molecule significantly reduced inactivation of AAT activities and reduced time to purification. Rapid purification eliminates multiple purification steps while preserving critical activities of the constructs. For example, these rapidly purified fusion molecules are capable of retaining cytokine inhibiting functions, modulate immune and inflammatory molecule production compared to control plasma derived AAT (e.g. typical purification of naturally occurring AAT and purification of commercially available formulas). Significantly reduced concentrations of fusion molecules can be used to achieve the same or improved modulatory functions. Further, fusion molecules disclosed herein where an Fc region of Fc-AAT has a truncated hinge or deleted hinge region has superior activity when compared to plasma-derived AAT or fusion molecules of Fc-AAT with intact Fc.

In accordance with these embodiments, a unit including two or more AAT-Fc (hinge deletion/truncation) constructs (or carboxyterminal AAT peptide fragments) can be purified and used in compositions and methods disclosed herein. Some of these embodiments of Fc-huAAT (hinge deletion) can be used in any method or composition contemplated herein. Other embodiments can include using IgG1, IgG2, IgG3 or IgG4 Fc fragments (hinge truncated or deleted) linked to an AAT molecule purified by rapid purification methods in order to preserve activity of the AAT molecule.

Certain embodiments disclosed herein concern using Protein A for a minimum step (e.g. one-step) purification of Fc-fusion constructs in order to avoid the deleterious effects of other methods and multiple steps as used in plasma AAT purification. Some embodiments herein concern preserving 85%, 90%, 95% or more AAT's anti-inflammatory activity in the fusion molecule compared to standard purifications used for commercially available products (e.g. Aralast™, Prolastin™) and/or compared to naturally-occurring AAT found in blood plasma. In some embodiments, fusion molecules of the instant application have demonstrated 100 to 1000 fold more activity to reduce inflammation or treat a condition compared to commercially available formulations. In other embodiments, AAT-Fc having a truncated or deleted hinge region of the Fc portion demonstrated superior activity in vivo to Fc-AAT where Fc is intact.

Disclosed herein are methods to create and recover constructs having activities similar and in certain embodiments superior plasma-derived AAT. Certain activities known to be of interest regarding AAT include immunomodulatory or inflammatory modulation activities. It is contemplated herein that constructs described are isolated and assessed for activities other than serine protease inhibitor activities. In some embodiments, constructs disclosed herein have increased IL-1 receptor antagonist activity compared to commercially available compositions and reduced IL-1β production as well as other pro-inflammatory cytokines.

In certain embodiments, compositions (e.g. construct compositions) and methods concern modulating adverse effects of radiation on a subject. In some embodiments, compositions and methods concern treating a subject having radiation therapy or radiation for example, when administered to a subject having cancer or suspected of developing a malignancy or for uncontrolled cellular growth. Other embodiments disclosed herein concern treating a subject having been exposed to radiation, for example, by accident or by a purposeful act.

Some embodiments concern administering AAT generated using recombinant technology to a subject in need of AAT therapy. In accordance to these embodiments, a subject could have an AAT-deficiency, an inflammatory or immune condition or other AAT-related condition known in the art. Certain embodiments herein include administering a composition having at least one construct and a pharmaceutically acceptable carrier to a subject in need of such a treatment. In certain embodiments, doses administered to a subject can include a 10-fold, 100-fold or 1,000 fold reduction in dose (e.g. of an Fc-AAT3 construct) to the subject compared to commercially available formulations. In certain embodiments, a dose can be about 1 mg/kg to about 10 mg/kg to a subject compared to 10 mg/kg to 100 mg/kg (concentrations of commonly used commercially available AAT such as Aralast™ or Prolastin C™).

Some embodiments of the present invention concern reducing adverse effects of ischemia reperfusion. In accordance with these embodiments, compositions herein can be used to modulate the effects of ischemia reperfusion damage as a consequence of a myocardial infarction or kidney failure or other condition. In other embodiment, fusion constructs reported herein can be used to modulate the onset or progression of cardiac tissue remodeling (e.g. enlargement and necrosis of cardiac tissue), for example, left or right ventricular (LV) remodeling. In accordance with these embodiments, intervention for example, by administering a composition disclosed herein, can modulate onset, severity (e.g. of damage) or progression before, during, or after a cardiac event that can lead to heart muscle damage. In yet other embodiment, compositions disclosed herein can be administered to a subject having a heart condition to reduce early or late infarct size. In accordance with these embodiments, an early infarct can be one measured before (for example, a baseline), during or within 48 hours after surgery or other cardiac event. In other embodiments, a late infarct can be one measured after 48 hours or up to days or weeks after surgery or other cardiac event, for example 7 days after a cardiac event. In yet other embodiments, compositions disclosed herein can be used to treat a subject having a cardiac event (e.g. myocardial infarction), to modulate cardiac enlargement and dysfunction as a consequence of the cardiac event by about 5%, or about 10%, or about 15%, or about 20% or about 25%, or about 30% or more compared to a subject not treated with these compositions.

Certain embodiments concern compositions for treating a subject having a cardiac event. In accordance with these embodiments, a composition can include, an AAT-Fc (hinge deletion or truncation) (e.g. human AAT or fragment thereof), or mutants thereof having no significant serine protease inhibitor activity, or alleles thereof (for example, there are approximately 100 naturally occurring AAT variants), or analogs thereof or fusion protein thereof (e.g. a human IgG or fragment of human IgG (Fc)). Some embodiments concern administering naturally-occurring AAT to a subject having or having had a cardiac event in order to modulate LV remodeling. Other embodiments can concern administering a composition of one or more carboxyterminal derivative(s) or fragment(s) of AAT including, for example, a fragment of the last 80 AAs of the 394 AA naturally occurring AAT (SEQ ID NO. 1 and 33). Some embodiments concern treating a subject having a cardiac condition with a recombinantly-produced AAT fusion peptide disclosed herein, in order to ameliorate the cardiac condition.

Other embodiments include treating a subject having an infection (e.g. bacteria or viral infection) or preventing a subject from getting an infection using compositions disclosed herein. In certain embodiments, a viral infection can be an infection due to HIV or influenza (e.g. H1N1, influenza A or B). In other embodiments, a bacterial infection can include bacterial pneumonia, a mycobacterial infection, exposure to bacillis anthracis or other bacterial infection.

Some embodiments concern compositions disclosed herein to reduce or prevent graft rejection. In other embodiments, compositions disclosed herein can be used to reduce the incidence or prevent Graft versus Host disease (GVHD). In certain embodiments, a composition disclosed herein can be used to treat a subject before, during or after organ, tissue or cellular transplantation. In other embodiments, an organ, tissue or cell culture can be exposed to a composition having an Fc-AAT (hinge deleted or truncated) fusion molecule in order to preserve the organ, tissue or cell culture prior to and during transplantation.

In certain embodiments, compositions for administration can be in a range of between about 0.1 ng and about 10 mg per ml or mg of the formulation. A therapeutically effective amount of AAT peptides or constructs that have similar activities as AAT or peptides may be measured in molar concentrations and may range between about 1 nM and about 10 mM. The formulation is also contemplated in combination with a pharmaceutically or cosmetically acceptable carrier. Precise doses can be established by well known routine clinical trials without undue experimentation. In one embodiment, a subject may be treated for a conditions with a single dose (e.g. 0.6 mg/kg to 0.8 mg/kg by IV infusion depending on the potency of the construct composition compared to a control) of an active agent (e.g. AAT construct or AAT peptide derivative thereof). In accordance with this embodiment, the subject can be treated with follow-on treatments (e.g. 5 to 10 days following a single dose or more) as determined by a health professional. Other embodiments can include using a control population having a placebo (e.g. human serum albumin administration or other comparable placebo) and comparing a placebo effect to a population receiving compositions disclosed herein.

In other embodiments, a composition disclosed herein can be administered to a subject every time a subject undergoes radiation and/or chemotherapy. Some embodiments disclosed herein concern treatment of a subject undergoing cancer therapies. Cancer treatments include, but are not limited to, treatment for bladder, breast, kidney, leukemia, lung, myeloma, liposarcoma, lymphoma, tongue, prostate, stomach, colon, uterine cancers, melanoma, pancreatic, eye and other known cancers.

Some embodiments disclosed herein concern treating a subject having prostate cancer. In accordance with these embodiments, a male subject having prostate cancer can be treated with compositions disclosed herein before, during or after radiation and/or chemotherapy in order to reduce development of impotence or erectile dysfunction, common side effects of prostate cancer therapies.

In certain embodiments, the subject is a mammal. In some embodiments, the mammal is a human. In yet other embodiments, the subject is a pregnant female or young child. In other embodiments, the subject is a pet, a domesticated animal or livestock.

In other embodiments, the subject or mammal can be a non-domesticated mammal such as a captive or free wild animal.

In certain embodiments, compositions comprising human AAT mutants having no significant serine protease inhibitor activity can be used in constructs disclosed herein for use in methods described (e.g. AAT fusion peptide derivative or Reactive Center Loop related mutant fusion polypeptide). In accordance with these embodiments, recombinant molecules or fusion protein constructs disclosed herein have no significant serine protease inhibition activity. These constructs can be generated where they associate with an immune molecule (e.g. Fc). Association with the immune molecule can be used for rapid purification of the construct thereby preserving activities of the AAT or carboxyterminal thereof by reducing purification steps. In certain embodiments, the purification step is a single step using an affinity process (e.g. Protein A). These processes preserve conformation of the constructs disclosed herein by reducing deleterious purification steps used in other commercially available formulations (e.g. Aralast™, Zemaira™, Prolastin C™, and Glassia™). Other embodiments concern AAT-derived fragment constructs adapted to have no significant serine protease inhibitor activity. Constructs herein can include, but are not limited to constructs including a carboxy-terminal peptide or amino-terminal peptides corresponding to AAT, an analog thereof, any derivative of AAT carboxy terminus that binds to serpin-enzyme complex (SEC) receptor or a combination thereof linked to an immune molecule (e.g. IgG molecule).

Pharmaceutical compositions contemplated herein may further include an agent selected from the group consisting of an anti-inflammatory agent, an immunosuppressive agent, an immunomodulatory agent, an anti-viral agent, an anti-pathogenic agent, an anti-bacterial agent, a protease inhibitor, and a combination thereof. Some of these agents include, but are not limited to, one or more of interferon, interferon derivatives including betaseron, beta-interferon, prostane derivatives including iloprost, cicaprost; glucocorticoids including cortisol, prednisolone, methyl-prednisolone, dexamethasone; immunosuppressives including cyclosporine A, FK-506, methoxsalene, thalidomide, sulfasalazine, azathioprine, methotrexate; lipoxygenase inhibitors comprising zileutone, MK-886, WY-50295, SC-45662, SC-41661A, BI-L-357; leukotriene antagonists; peptide derivatives including ACTH and analogs thereof; soluble TNF-receptors; TNF-antibodies; soluble receptors of interleukins, other cytokines, T-cell-proteins; antibodies against receptors of interleukins, other cytokines, T-cell-proteins; and calcipotriols; Celcept®, mycophenolate mofetil, and analogues thereof taken either alone or in combination.

Other embodiments concern combination therapies for the treatment of a subject undergoing cancer related therapies, for example a composition disclosed herein can be combined with any other agent known to shrink or eliminate a tumor or reduce metastasis of a tumor in the subject or treat other aspects of cancer in the subject.

In certain embodiments, treating the subject with a composition encompassed herein to modulate normal cell damage can be by at least 10%, or by at least 20% or by at least 30%, or by at least 40%, or by at least 50%, or by at least 60%, or by at least 70%, or by at least 80%, or by at least 90% compared to a subject not treated with the composition.

As such, those skilled in the art will appreciate that the conception, upon which this disclosure is based, can readily be used as a basis for designing other methods for carrying out the several features and advantages of embodiments of the present invention.

BRIEF DESCRIPTION OF THE DRAWINGS

The following drawings form part of the present specification and are included to further demonstrate certain embodiments disclosed herein. Embodiments may be better understood by reference to one or more of these drawings in combination with the detailed description of specific embodiments presented herein.

DESCRIPTION OF ILLUSTRATIVE EMBODIMENTS

Definitions

Figure 1:
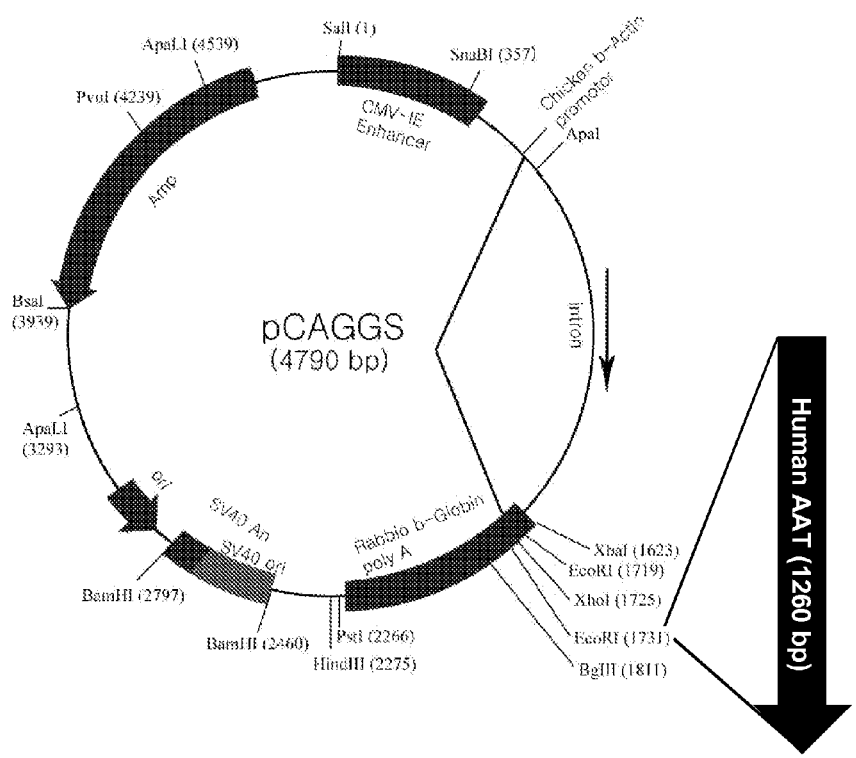
FIG. 1 represents a schematic of an AAT construct contemplated of use for some embodiments disclosed herein for production of recombinant AAT is certain embodiments. AAT peptide fragments can also be produced using certain embodiments of the present invention.

As used herein, "a" or "an" may mean one or more than one of an item.

As used herein, "about" can mean plus or minus 10%, for example, about 10 minutes can mean from 9 to 11 minutes.

As used herein, "Fc-AAT" or "AAT-Fc" can mean an Fc fragment linked to AAT or AAT carboxyterminal fragment either at the carboxy-terminal or amino-terminal end of an AAT polypeptide.

DETAILED DESCRIPTION

In the following sections, various exemplary compositions and methods are described in order to detail various embodiments of the invention. It will be obvious to one skilled in the art that practicing the various embodiments does not require the employment of all or even some of the specific details outlined herein, but rather that concentrations, times and other specific details may be modified through routine experimentation. In some cases, well known methods, or components have not been included in the description.

It has been traditionally thought that AAT (alpha-1 antitrypsin) anti-inflammatory activities were attributed to its ability to inhibit serine proteases, and particularly neutrophil elastase. This is the basis for its use in replacement therapy for humans with AAT deficiencies. AAT that is currently commercially available for human use is standardized by its anti-elastase units not for other AAT-related activities. These commercially available formulations are purified from pooled human plasma, but these are not pure (although some are purer than others) because they contain other human serum proteins. The majority of studies on human AAT in vitro as well as in vivo models depend on the use of these commercially available preparations directed to serine protease inhibition activity, each approved for use in humans. Although infusions of AAT in humans with various AAT deficiency states are considered safe, the role of contaminating proteins remains unknown. Certain embodiments herein report quick production of recombinant forms of AAT of high purity and high activity to overcome issues of contaminating co-purified plasma proteins.

In certain embodiments disclosed herein a challenge is presented regarding a long-held concept that inhibition of neutrophil elastase is the sole mechanism for the therapeutic benefit of augmentation therapy due to AAT. One contribution clarified herein is creation of novel forms of fusion molecules of AAT such as Fc fusions that not only aide in purification of AAT but are more potent in activity than native, commercially available compositions. For decades scientists have attempted to generate recombinant forms of AAT that retain similar or equal beneficial effects of AAT but have been largely unsuccessful. Fc fusion proteins have a long history of having safety and many are used therapeutically by hundreds of thousands (e.g. Enbrel™ and Alabacept™, for example, of use for rheumatoid arthritis treatment). Fc-AAT fusion molecules presented herein can be readily produced and purified in large quantities and have reduced side effects of other constructs. In addition, fusion constructs presented herein have up to 10, to 20, to 30, to 40 to, 50 . . . to 100 and in certain cases up to 1,000 times more potency when compared to commercially available formulations (e.g. Zemaira™, Aralast™, Prolastin™ etc.) regarding AAT activities such as anti-inflammatory and anti-immune activities. In certain aspects, it is considered superior to commercially available formulations in part because the commercially purified plasma-derived AAT formulations likely destroy anti-inflammatory domains during the purification. In certain methods, one of the initial steps in purifying plasma-derived AAT is cold-alcohol precipitation which is highly oxidative. Thus, fusion molecules provided herein provide a superior substitute for AAT for any of clinical indications such as a superior treatment for COPD in AAT deficient patients, for reducing effects of graft rejection, for treatment of inflammatory conditions because preparations disclosed herein focus in-part on maintaining anti-inflammatory domains of AAT rather than on elastase inhibition although AAT activities are preserved in total in other formulations.

Other embodiments disclosed herein concern modified Fc molecules associated with various forms of AAT. In accordance with these embodiments, immunoglobulin molecules fused to AAT or a peptide fragment of AAT can be IgG1, IgG2, IgG3, or IgG4. In certain embodiments, a fusion molecule of AAT can include IgG2 where a 12-amino acid hinge region is mutated, truncated or eliminated prior to fusing it to AAT. For example, one fusion molecule disclosed herein in concerns IgG2 with a hinge deletion (also referred to as clone 3 or Fc3) fused to AAT. Truncation, mutation or elimination of the hinge region of IgG2 reduces in vivo side effects of the fusion molecule. Some embodiments include reduced ability to activate complement and other activities. Fusion molecules disclosed herein retain superior activity to a native AAT, plasma-derived composition (e.g. commercially available compositions such as Aralast™.

Excess inflammation or inflammation activation can result in the initiation, progression and destructive nature of several chronic diseases, for example chronic destructive or wasting diseases. These include, but are not limited to, autoimmune diseases, such as rheumatoid arthritis, lupus (systemic lupus erythematosus), diabetes such as Type 1 where insulin-producing beta cells can be destroyed by an immune attack. Other conditions that may be treated by compositions and methods disclosed herein include Type 2 diabetes. In addition to autoimmune diseases, chronic inflammation of coronary arteries can increase the risk of a heart attack or stroke. Chronic inflammation also contributes to inflammation in the intestines (e.g. Crohn's Disease, inflammatory bowel disease (IBD) or ulcerative colitis). Several naturally occurring proteins are produced each day in a subject that control inflammation in the subject. AAT is one of these proteins. One drawback of a therapy with AAT is that commercially available AAT is isolated from the plasma of human blood donors therefore supply is limited to available plasma. Uses of therapeutic AAT are growing because its application is not limited to the current uses such as chronic pulmonary obstructive disease (COPD) and AAT replacement therapies.

Certain embodiments herein report effective recombinant forms of human alpha 1 antitrypsin functional to treat AAT-deficient conditions or AAT-responsive conditions similar to and in certain aspects more efficiently than plasma-derived AAT. In certain embodiments, compositions and methods disclosed herein concern AAT (e.g. human or other mammal) fused to an immune molecule or fragment thereof (e.g. IgG1, IgG2). In other embodiments, fusion proteins can include truncated versions of AAT. In accordance with these embodiments, certain fusion polypeptide can be linked through the amino-terminus of AAT or fragment thereof. Some embodiments concern constructs of AAT fused to an immunoglobulin molecule such as Fc. In certain embodiments, AAT or a carboxyterminal peptide fragment thereof can be linked to Fc derived from IgG1 or IgG2. Fc derived from IgG2 can be used, for example, because the Fc of human IgG1 binds to the complement receptor on myeloid cells and IgG2 was found to be superior in certain compositions and methods.

Three distinct types of Fc-gamma (γ) receptors occur: designated FcγRI, FcγRII, and FcγRIII are found on human leukocytes. FcγRI (CD64) is a high-affinity receptor expressed on monocytes, macrophages, neutrophils, myeloid precursors and dendritic cells. FcγRI has a high affinity for monomeric human IgG1 and IgG3, but does not bind IgG2. It has been demonstrated that binding of the Fc part of IgG to an FcγR is instrumental in the induction of the cell's effector function, including the release of inflammatory mediators.

It has been demonstrated that four IgG subclasses differ from each other with respect to their effector functions, for example, the length and flexibility of the hinge region are different. The flexibility of the hinge region decreases in the order IgG3>IgG1>IgG4>IgG2. The Fc IgG2 has 12 amino acids in the hinge region and is less flexible than Fc IgG1. It is contemplated that any hinge region of an Fc fragment can be manipulated to delete or modify the hinge region in order to reduce additional in vivo side effects of a fusion molecule including, but not limited to, complement activation. One or more amino acids can be modified or removed from this region to generate fusion molecules with increase AAT activity compared to an unmodified control. In certain embodiments, a hinge region can be shortened in order to modulate flexibility in the construct, to reduce in vivo side reactions to the Fc or alter tertiary structure to enhance AAT activities in an Fc-AAT construct contemplated herein. In some embodiments, Fc-AAT constructs disclosed herein have increased half-life compared to a plasma-derived AAT formulation.

In addition, the Fc IgG2 is resistant to proteases and, as stated previously, does not bind to the high affinity FcγRI, as well as, weak in its ability to activate complement. In certain embodiments, Fc used in fusion proteins contemplated herein may be from IgG1 or IgG2 or IgG3 or IgG4. In other embodiments, Fc can be a mutant molecule that does not bind to a receptor. In yet other embodiments, Fc can be a wildtype or mutant form from IgG2 linked to AAT or carboxyterminal peptide thereof. In certain embodiments, Fc molecules may be associated with AAT molecules to make dimers of Fc-AAT, for example, linked by disulfide bonds. In other embodiments, monomeric molecules of Fc-AAT can be generated and used in methods disclosed herein. Certain constructs disclosed concern Fc-AAT wherein the Fc of the construct is modified to further reduce flexibility in the hinge region, for example by removing additional amino acids in this region. Any of the molecules described herein can be rapidly purified using, for example, Protein A column or matrix or other quick purification or enrichment method for rapid separation to preserve activity.

Embodiments herein report generating constructs of alpha-1 antitrypsin (AAT) or carboxyterminal fragment thereof having superior properties to current commercially available AAT compositions. Other embodiments report methods for purifying fusion proteins or peptides and subsequent uses for purified AAT fusion molecules disclosed herein. It is contemplated that commercially available AAT derived from blood plasma is in short supply, is currently purified by methods that destroy important properties of AAT and a need exists for synthetic versions of this molecule or updated purification methods where the synthetically produced AATs are capable of performing as well if not better than native forms of AAT or AAT derived peptides.

With respect to AAT activities other than serine protease inhibition, AAT exerts anti-inflammatory properties by several mechanisms. Preliminary data using a mutation of the anti-protease site (e.g. to reduce anti-protease activity to insignificant levels) support the concept that some of AAT's activities do not require the anti-protease properties of AAT. In certain embodiments, different recombinant truncated and mutant forms of naturally occurring human AAT (e.g. 394 AA, $M_r$ about 51,000) are generated in order to assess anti-inflammatory properties of the molecule. This approach allows for producing AAT molecules of various compositions, which is extremely difficult and near impossible using the standard methods of plasma-derived AAT. It was demonstrated that anti-inflammatory properties of AAT can be oxidized by currently used purification procedures of commercially available compositions. Methods disclosed herein provide superior purification methods for preserving this activity in fusion molecules and constructs described.

In certain methods previously disclosed, it has been demonstrated that AAT blocks toxic activities of IL-1β on mouse model and human pancreatic islet cells. Some embodiments herein concern recombinant production of AAT fusion molecules capable of mimicking this activity. In certain embodiments, recombinantly-produced fusion peptides of the carboxyl terminal region of human AAT are generated for blocking toxic activities or production of IL-1β and for reducing caspase-1 activity (see Example section). These fusion peptides are useful for blocking or reducing production of or activities of pro-inflammatory molecules and therefore are useful for treatment and prevention of many health conditions.

Alpha 1-Antitrypsin or α1-antitrypsin (AAT) was first classified as a protease inhibitor belonging to the serpin superfamily. It is generally known as serum trypsin inhibitor. AAT can also be referred to as alpha-1 proteinase inhibitor (A1PI) because it inhibits a wide variety of proteases. AAT protects tissues from enzymes of inflammatory cells, especially neutrophil elastase, and typically has a range in blood of about 1.5 to 3.5 gram/liter but the concentration can rise many-fold upon acute inflammation. Over 100 different variants of $α_1$-antitrypsin have been described in various populations. The most common variety of AAT is termed M, based on its migration in an IEF gel. Other variants are termed A-L and N-Z, depending on whether they run proximal or distal to the M band. The presence of deviant bands on IEF can signify the presence of AAT deficiency. As indicated above, M type AAT has several subtypes and all of these subtypes are contemplated of use herein.

The current trend for obtaining therapeutic concentrates of AAT is to prepare AAT from the blood plasma of blood donors. This is a limited resource and requires extensive purification steps to get to a marketable product. So far, the United States Food & Drug Administration has approved the use of several commercial products derived from human plasma: For example, some of these products include Prolastin®, ProlastinC®, (Talecris (now Grifols, Raleigh, N.C.), Zemaira®, and Aralast® (Baxter) and Kamada has both an aerosol and an intravenous product (Kamada, Israel). Most of these formulations are administered intravenously for AAT therapy in AAT deficient patients and can cost up to $100,000 per year per patient. It has been demonstrated that plasma isolated AAT has reduced activity compared to AAT derived from blood. Compositions disclosed herein have increased anti-inflammatory activity similar to that of blood not of plasma-derived AAT; and greater activity than commercially available formulations which have activities that are based on anti-protease activities.

One study analyzed and compared three of the FDA-approved products in terms of its primary structure and glycosylation. Several of the products showed differences compared to the normal human plasma AAT that are likely introduced during purifications procedures. In addition, it was previously demonstrated that comparison of the commercial formulations in certain studies had large variability regarding serine protease inhibition activity and AAT purity. Recently, one of the standard commercially available formulations, Prolastin®, was evaluated and a new formulation ProlastinC® was purified differently than Prolastin®, in order to increase anti-protease activity (e.g. serine protease inhibition activity) in the final product. All of the activities reported for these products are directed to serine protease inhibition activities not anti-inflammatory or immune modulatory activity or alternative AAT-related activities.

In certain embodiments, compositions generated herein may be more useful as an aerosol formulation than other forms, in part, due to its reach to the lower respiratory tract than intravenous methods. It is contemplated herein that any of the construct formulations can be introduced to a subject by any method known in the art as a pharmaceutically acceptable formula.

In spite of efforts to improve plasma-derived AAT formulations, there is a finite supply of plasma available where AAT is derived and it is expensive to produce. Therefore, recombinant AAT molecules have been sought. One of the issues encountered by researchers developing recombinant AAT molecules has been reduced activity of these molecules compared to plasma-derived formulations. Recombinant molecules generated previously were often less active when assayed by serine protease inhibitor assays compared to the commercially available formulations previously indicated. Thus, limited supply of plasma and inferior recombinant AAT molecules of the past have left a void for generating adequate supplies of AAT for past and recently discovered methodologies.

Some embodiments herein concern generating a highly active, highly functional recombinant AAT construct relative to commercially available formulations for use in any AAT method or treatment known in the art. In certain embodiments, recombinant AAT disclosed herein includes a full length molecule or carboxyterminal peptide derivative thereof. Some embodiments concern simultaneous synthesis of more than one construct having AAT molecules each associated with an immunological element (e.g. an Fc fragment or other fragment) and co-purified. Other embodiments can concern generating a construct of one or more carboxyterminal derivative(s) or fragment(s) of AAT including, for example, a fragment of the last 80, 70, 60, 50, 40, 30 amino acids or other fragment of the carboxyterminus of the molecule associated with one or more immune molecule(s) to form a construct for methods and uses disclosed herein.

An AAT molecule of a construct contemplated herein can concern naturally occurring alpha-1 antitrypsin (e.g. human or other mammal), or fragments, or derivatives thereof, or mutant forms of AAT, any AAT molecule having no significant serine protease inhibitor activity, or alleles thereof (for example, there are approximately 100 naturally occurring AAT variants), or analogs thereof or fusion protein thereof (e.g. a human IgG or fragment of human IgG). In accordance with these embodiments, a construct can include dimeric AAT constructs each associated with an immunological fragment (e.g. an Fc fragment that links two molecules of AAT) wherein the Fc-AAT constructs are linked together by one or more disulfide bond(s). See for example, FIG. 1 and FIG. 2 disclosed herein. In certain methods, purification of recombinant AAT or AAT-peptide and immune molecule complexes increase activity of the AAT or AAT-peptide by significantly reducing purification steps and significantly increasing potency of AAT or AAT-peptide. In accordance with these embodiments, recombinant AAT molecules contemplated herein can be used as a fusion polypeptide (dimer or monomeric form) or can be cleaved from its immune molecule after purification and used as in reduced concentrations compared to commercially available formulations. Some embodiments concern, using $1/100^{th}$ to $1/1000^{th}$ of a concentration compared to commercially available formulations. In certain examples, these molecules can be used in compositions to inhibit cytokines or modulate the immune and inflammatory functions of the molecules compared to controls (e.g. typical purification of naturally occurring AAT and purification of commercially available formulas). In one embodiment, recombinant molecules of the instant application have demonstrated 100 to 1000 fold more activity than commercially available formulation. Certain activities known to be of interest regarding AAT constructs of the instant invention include immunomodulatory or inflammatory modulation activities. In some embodiments, constructs disclosed herein have increased IL-1β receptor antagonist activity compared to commercially available compositions.

Some Uses for Recombinant AAT in the Treatment of Health Conditions

Some embodiments reported herein concern using recombinant AAT or fusion protein or carboxyterminal fragment fusion molecule thereof to treat a subject in need of AAT therapy, AAT replacement or AAT supplementation. AAT treatments have been reported of use in a variety of conditions including, but not limited to, apoptosis-related conditions, nitric oxide-related conditions, ischemia-reperfusion dysfunction induced conditions, graft rejection and cellular rejection, diabetes, emphysema, other lung conditions, treatment and prevention of bacterial infection, treatment and prevention of viral infections, radiation induced injury and the like.

Some embodiments herein concern compositions of fusion molecules disclosed herein of use to treat an inflammatory disorder (e.g. IBD, Crohn's disease, arthritis). In some embodiments, fusion molecules disclosed herein have enhanced anti-inflammatory activity compared to commercially available AAT compositions. Some embodiments concern a hinge-deleted; truncated or mutated IgG2 Fc fused to synthetically generated AAT or carboxyterminal truncated version thereof (e.g. the last 36 to 80 amino acids of AAT).

In one embodiment, Fc-AAT comprises IgG2 hinge deletion with a 2 amino acid linker attached to an intact synthetically generated AAT molecule to make what is referred to in certain cases as clone 3.

In certain embodiments, compositions and methods disclosed herein can be used to reduce or prevent onset of inflammatory bowel disorder in a subject. In accordance with these embodiments, reduction in conditions associated with IBS in a subject may be on the order of about 10-20%, or about 30-40%, or about 50-60%, or about 75-100% reduction or inhibition. In accordance with these embodiments, a subject having IBS or IBD may be treated with a pharmaceutically acceptable composition of recombinant or a fusion protein of AAT or AAT-carboxyterminal peptide (Fc-AAT with a hinge deletion or hinge truncation) to reduce wasting or to reduce loss of or restore barrier function compared to a control subject not receiving such a composition. In other embodiments, compositions disclosed herein can be used to reduce onset of an inflammatory bowel disorder.

Some embodiments herein concern restoring bowel or intestinal hyperpermeability in a subject having an acute or chronic condition. In accordance with these embodiments bowel or intestinal hyperpermeability or loss of barrier function can be due to chronic diseases such as systemic inflammatory response syndrome (SIRS), inflammatory bowel disease, type 1 diabetes, allergies, and asthma. In certain embodiments, a subject having bowel or intestinal hyperpermeability can be treated by a health professional by a predetermined regimen such as daily, twice weekly, weekly or other predetermined regimen.

In certain embodiments, compositions disclosed herein can be used to treat certain indications including but not limited to diabetes (e.g. Type 1 and Type 2), immune diseases such as autoimmune disease, inflammatory diseases, cardiac disorders infectious disease and others. Some diseases disclosed herein may fall under more than one category such as asthma which can be considered an inflammatory disease, an autoimmune disease or a lung disease or other. In certain embodiments, compositions disclosed herein can be used to treat autoimmune diseases that include, but are not limited to, rheumatic diseases such as rheumatoid arthritis, systemic lupus erythematosus (SLE), Type I diabetes, and autoimmune diseases of the thyroid, gut, and central nervous system (e.g., rheumatoid arthritis, lupus erythematosus, Sjogren's syndrome, scleroderma, mixed connective tissue disease, dermatomyositis, polymyositis, Reiter's syndrome, and Behcet's disease); autoimmune diseases of the central nervous system (e.g., multiple sclerosis, myasthenia gravis, or encephalomyelitis); autoimmune disease of the gastrointestinal system: (e.g., Crohn's disease, ulcerative colitis, inflammatory bowel disease, Celiac disease, Sprue); autoimmune disease of the thyroid: (e.g., Hashimoto's thyroiditis, or Graves' Disease); and ocular autoimmune disease, (e.g., uveitis). Autoimmune disorder contemplated herein, can concern Alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, Bullous pemphigoid, cardiomyopathy, Celiac sprue-dermatitis, chronic fatigue immune dysfunction syndrome (CFIDS), chronic inflammatory demyelinating polyneuropathy, Churg-Strauss syndrome, Cicatrical pemphigoid, CREST syndrome, Crohn's disease, Discoid lupus, essential mixed cryoglobulinemia, fibromyalgia-fibromyositis, Glomerulonephritis, Guillain-Barre, Hashimoto's thyroiditis, idiopathic pulmonary fibrosis, idiopathic thrombocytopenia purpura (ITP), irritable bowel disease (IBD), IgA neuropathy, Juvenile arthritis, Lichen planus, Lupus erythematosus, Meniere's disease, mixed connective tissue disease, multiple sclerosis, Type 1 or immune-mediated diabetes mellitus, Myasthenia gravis, Pemphigus vulgaris. Pernicious anemia, Polyarteritis nodosa, Polychrondritis, Polyglandular syndromes, Polymyalgia rheumatic, Polymyositis and dermatomyositis, Primary agammaglobulinemia, Primary biliary cirrhosis, psoriasis, psoriatic arthritis, Raynauld's phenomenon, Reiter's syndrome, Rheumatoid arthritis, Sarcoidosis, Scleroderma Sjogren's syndrome, Stiff-man syndrome, Systemic lupus erythematosus, Lupus erythematosus, Takayasu arteritis, Temporal arteristis/giant cell arteritis, ulcerative colitis, Uveitis, Vasculitides such as dermatitis herpetiformis vasculitis, Vitiligo, Wegener's granulomatosis, T cell mediated autoimmune disease, rheumatic disease, rheumatic arthritis, and lupus erythematosus.

In other embodiments, compositions disclosed herein can include treating conditions such as inflammatory conditions including, but not limited to, allergic disorders, or for example, arthritis, inflammatory osteolysis, asthma, chronic inflammation (e.g. from chronic viral or bacterial infections), chronic obstructive pulmonary disease (COPD), Encephalitis, inflammatory bowel disease (IBD), psoriasis (e.g., plaque psoriasis, pustular psoriasis, erythrodermic psoriasis, guttate psoriasis or inverse psoriasis), pulmonary fibrosis, undifferentiated arthropathy, undifferentiated spondyloarthropathy. Other conditions can include, but are not limited to respiratory conditions, for example, asthma, COPD, emphysema. Certain embodiments concern treating a subject on a monthly, weekly, biweekly, daily, twice daily or other regimen to reduce deleterious effects of inflammation using 10- to 100-fold less AAT in the form of a recombinantly produced fusion molecule where the fusion molecule comprises Fc-AAT (hinge deleted or hinge truncated form). In certain examples, Fc-AAT3 or Fc-AAT4 can be used in a composition to inhibit deleterious effects of these disorders and ameliorate the symptoms associated thereof.

Radiation Protection and Cancer

In certain embodiments, compositions (e.g. construct compositions) and methods concern modulating adverse effects of radiation on a subject. In some embodiments, compositions and methods concern treating a subject having radiation therapy or radiation for example, when administered to a subject having cancer or suspected of developing a malignancy or for uncontrolled cellular growth. Other embodiments disclosed herein concern treating a subject having been exposed to radiation, for example, by accident or by a purposeful act in part, in order to reduce adverse side effects of radiation treatment.

Some embodiments disclosed herein concern treatment of a subject undergoing cancer therapies. In accordance with these embodiments, a subject undergoing cancer therapies can be treated with a composition disclosed herein to reduce or prevent detrimental effects of the treatment (e.g. from radiation and/or chemotherapy treatments). Cancer treatments include, but are not limited to, treatment for bladder cancer, breast cancer, kidney cancer, leukemia, lung cancer, myeloma, liposarcoma, lymphoma, tongue cancer, prostate cancer, stomach cancer, colon cancer, uterine cancer, melanoma, pancreatic cancer, brain cancer, eye cancer, skin cancer and other known cancers.

In other embodiments, compositions disclosed herein can be used to treat a subject having cancer. Cancers contemplated for these embodiments can include, but are not limited to, fibrosarcoma, myxosarcoma, liposarcoma, chondrosarcoma, osteogenic sarcoma, chordoma, angiosarcoma, endotheliosarcoma, lymphangiosarcoma, Kaposi's sarcoma, lymphangioendothelio sarcoma, synovioma, mesothelioma, Ewing's tumor, leiomyosarcoma, rhabdomyosarcoma, rhabdosarcoma, colorectal carcinoma, pancreatic cancer, breast cancer, ovarian cancer, prostate cancer, melanoma, squamous cell carcinoma, basal cell carcinoma adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, myeloma, lymphoma, leukemia, or other known cancer.

Other embodiments include regarding radioprotection and compositions disclosed herein can concern treatment for trigeminal neuralgia, treatment for severe thyroid eye disease, treatment for pterygium, treatment for pigmented villonodular synovitis, prevention of keloid scar growth, prevention of heterotopic ossification, cosmetic or reconstructive surgical application surgery (e.g. reducing in scar formation), during chemotherapy, in combination with hormone therapy, and/or as an immunotherapy combination.

Certain side effects can occur during radiation exposure and even as a side effect of radiation therapy or chemotherapy. Some embodiments herein concern reduction or prevention of these side effects in a subject by treating the subject with compositions disclosed herein. Compositions can include AAT. AAT carboxyterminal peptides (e.g. 80 mer, 36 mer etc.), recombinant/fusion forms of AAT and/or recombinant/fusion forms of AAT carboxyterminal peptides. Side effects of radiation therapy can include, but are not limited to, cellular damage, pain, swelling, local irritation, fibrosis, scaring, loss of tissue integrity, increased tissue friability, difficulty in swallowing and other symptoms associated with radiation treatment or exposure. Other side effects that can be reduced or prevented concern side effects from total body irradiation (TBI), for example during bone marrow transplantation. These side effects can include the above and in addition, acute and chronic immunodeficiency and opportunistic infections.

Some embodiments disclosed herein concern treating a subject having or suspected of developing prostate cancer. In accordance with these embodiments, a male subject having or suspected of developing prostate cancer can be treated with compositions disclosed herein before, during or after radiation and/or chemotherapy treatment(s) in order to reduce side effects attributed to these therapies. For example, side effects can be, but are not limited to, development of impotence or erectile dysfunction.

Other conditions contemplated herein include systemic lupus erythematosis (SLE, or lupus), rheumatoid arthritis, sepsis, systemic lupus erythematosis (SLE, or lupus), rheumatoid arthritis, inflammatory bowel disease, sepsis, autoimmune diseases, atherosclerosis, Alzheimer's disease, arthritis, muscular dystrophy, Downs syndrome, multiple sclerosis, stroke, neurodegenerative disorders, other inflammatory diseases or conditions and seronegative spondyloarthropathies.

In certain embodiments, compositions disclosed herein can be used to treat a subject in septic shock (see animal models for these confirmation studies: Doi et al The Journal of Clinical Investigation Volume 119 Number 10 Oct. 2009, for an animal model of sepsis and sepsis-induced kidney injury). It has been demonstrated that plasma-derived AAT can be used systemically to treat both viral and bacterial infections in mouse models and in human cohort studies therefore, Fc-AAT (hinge deletion or hinge truncation of Fc e.g. FcAAT3) having been demonstrated as an improvement compared to plasma-derived AAT can be used to treat sepsis. For example, a subject having sepsis due to one or more infection or other cause can be treated with a composition disclosed herein to ameliorate the condition and potentially prevent death in the subject.

In certain embodiments, the subject is a mammal. In some embodiments, the mammal is a human. In yet other embodiments, the subject is a male, a female, a pregnant female, an infant or a juvenile.

Graft Rejection and Graft Survival

In other embodiments, recombinant or fusion polypeptides (e.g. Fc-AAT or Fc-AAT fragment) contemplated herein can be used to treat a subject undergoing a transplant, such as an organ or non-organ (e.g. cellular) transplant. In certain embodiments, cellular transplantation can include bone marrow, islet cell (e.g. islet allograft), corneal cell, stem cell, skin (e.g. cellular or larger), temporary cadaver transplants of skin (e.g. soft tissue, facial or other) or conditions related to cellular transplant rejection such as graft versus host disease (GVHD). Embodiments of the present invention provide for methods for ameliorating symptoms or signs experienced by a subject having or in need of a transplant. In accordance with these embodiments, symptoms or signs may include conditions associated with graft versus host disease (GVHD), or graft rejection. In one example, methods disclosed herein may be used to treat a subject undergoing bone marrow transplantation. In other embodiments, methods disclosed herein may be used to treat a subject undergoing stem cell or other cellular transplantation. In accordance with these embodiments, a subject may be treated to reduce transplantation rejection, preserve the cells of a transplant and/or prolong transplanted cell (graft) survival. Other embodiments can include treating a subject undergoing an organ transplant such as a heart, lung, intestinal, liver, pancreas, kidney or other organ transplant.

In one example, methods disclosed herein may be used to treat a subject undergoing bone marrow transplantation. In accordance with these embodiments, a subject can be treated before, during or after bone marrow transplantation to reduce or prevent graft rejection and/or GVHD in the subject.

In other embodiments, compositions and methods disclosed herein concern prevention or reducing the occurrence of organ transplant rejection. In other embodiments, compositions and methods disclosed herein concern prolonging organ transplantation. Transplants contemplated herein can concern transplantation of kidney, heart, liver, soft tissue, facial component transplant, intestinal transplants, and pancreas transplant. In addition, compositions disclosed herein can concern reduction or prevention of symptoms associated with transplantation of an organ or non-organ. Symptoms that can be reduced or prevented by treating a subject undergoing a transplant with compositions disclosed herein can include, graft rejection, kidney failure, lung failure, heart failure, mucosal ulcerations, reduced islet function (increased glucose, diabetes mellitus), graft versus host disease (GVHD), gastrointestinal (GI), ulceration, pulmonary failure, skin ulceration, coagulopathy, CNS dysfunction, and coma.

Yet other aspects of the present invention concern organ or cell preservation prior to transplantation. For example, cryoprotection or protection during transport or other preservation method may be enhanced by exposing an organ, tissues or cells to compositions disclosed herein. Certain embodiments herein concern using a composition disclosed herein for preserving an organ, tissue or cells in preparation for transplantation or for cryoprotection. In accordance with these embodiments, organs, tissue or cells can include any of those disclosed herein, for example, pancreatic islet cells, stem cells, bone marrow cells, kidney, liver, lung and other organ or cellular transplants.

Embodiments of the present invention provide methods for promoting prolonged graft survival and function in a subject including administering to a subject in need thereof a therapeutically effective amount of a composition including a substance of recombinant AAT or fusion protein thereof and a pharmaceutically acceptable excipient.

In certain embodiments of the present invention, compositions disclosed herein can further include combination therapy. For example, combination therapies can include one or more of interferon, interferon derivatives including beta-seron, beta-interferon, prostane derivatives including iloprost, cicaprost; glucocorticoids including cortisol, prednisolone, methyl-prednisolone, dexamethasone; immunosuppressives including cyclosporine A, FK-506, methoxsalene, thalidomide, sulfasalazine, azathioprine, methotrexate; lipoxygenase inhibitors comprising zileutone, MK-886, WY-50295, SC-45662, SC-41661A, BI-L-357; leukotriene antagonists; peptide derivatives including ACTH and analogs thereof; soluble TNF-receptors; TNF-antibodies; soluble receptors of interleukins, other cytokines, T-cell-proteins; antibodies against receptors of interleukins, other cytokines, T-cell-proteins; and calcipotriols; Celcept®, mycophenolate mofetil, and analogues thereof taken either alone or in combination.

Plastic Surgery and Reduction Prevention of Scarring

Other aspects disclosed herein concern reducing side effects and enhancing recovery post-reconstructive surgery, enhancement or cosmetic surgery (e.g. elective, cosmetic, burn victims or due to treatment such as radiation etc.). Reconstructive plastic surgery can performed to correct functional impairments caused by for example, burns; traumatic injuries, such as facial bone fractures and breaks; congenital abnormalities, such as cleft palates or cleft lips; developmental abnormalities; viral or bacterial infection and disease; and cancer or tumors. Reconstructive plastic surgery can be performed to improve function, but it may be done to reform a subject to a normal appearance.

One of the most common reconstructive procedures is tumor removal, laceration repair, scar repair, hand surgery, and breast reduction. Some other common reconstructive surgical procedures include breast reconstruction after a mastectomy, cleft lip and palate surgery, contracture surgery for burn survivors, and creating a new outer ear when one is congenitally absent. Medical professionals often use microsurgery to transfer tissue for coverage of a defect when no local tissue is available. Flaps of skin, muscle, bone, fat, or a combination can be excised from a subject's own body and moved to another site on the body, and reconnected to a blood supply etc. Therefore, compositions disclosed herein can be used before, during or after reconstructive or cosmetic surgery to reduce scarring and enhance tissue transfer and retention (e.g. reduction of graft rejection and scarring), if applicable. In certain embodiments, therapeutic compositions that include AAT fusion molecules such as Fc-AAT (hinge deletion or intact hinge region) can be used to reduce side effects of cosmetic and reconstructive procedures such as preventing or reducing inflammation, a common side effect of these surgeries that can lead to swelling and tissue damage. Other embodiments can include treating a subject having undergone or undergoing a reconstructive procedure to reduce recovery time and enhance the reconstructive process using compositions disclosed herein to augment or ameliorate inflammatory and immune reactions in a subject undergoing such a process. Compositions disclosed herein may be used to treat the subject systemically or by direct application to an affected area (e.g. applied as a salve or lotion or other mode) depending on need as determined by a health professional.

Diabetes

Some embodiments concern using compositions disclosed herein to treat a subject having or suspected of developing diabetes. In accordance with these embodiments, a subject can be administered a composition disclosed herein to any subject having diabetes to treat the disease in the subject. A subject having Type 1 or Type 2 diabetes can be treated with a composition disclosed herein. These treatments can be combined with any treatment known in the art for diabetes. In certain embodiments, compositions disclosed herein can be administered to a subject at reduced levels (e.g. concentrations) compared to currently available commercial formulations to treat a subject having diabetes. In accordance with these embodiments, a subject having diabetes can be a subject having early onset diabetes Type 1 such as one diagnosed within 5 years having with for example, detectable c-peptide levels, and/or with detectable insulin production, and/or with residual islet cell function.

Other embodiments can concern using a composition disclosed herein to protect islet cells in vivo (e.g. to preserve or rejuvenate islet cell function) or in vitro (e.g. during transport for transplantation). It is contemplated that compositions disclosed herein can be used to treat a subject having diabetes that has some remaining islet cell function and/or treat islet cells prior to transplanting them into a subject, to preserve islet cell integrity and function. Thus, it is contemplated that a subject may be treated before, during or after islet cell transplantation. In other embodiments, diabetes treatments can include treating a subject having insulin resistant diabetes, Type I and Type II. It has been demonstrated that Fc-AAT fusion molecules disclosed herein are capable of modulating production of pro-inflammatory cytokines as observed for plasma-derived AAT, only at significantly reduced concentrations. Compositions including Fc-AAT fusion molecules (hinge deleted or hinge truncation) can be used to preserve islet cell populations in a subject in need thereof.

Cardiac Conditions

Some embodiments of the present invention comprise treating a subject having a cardiac condition or undergoing cardiac intervention (e.g. surgery, preventative treatment). In accordance with these embodiments, a subject having a cardiac condition may have one or more of the following conditions including, but not limited to, myocardial infarction, myocardial ischemia, chronic systemic arterial and venous hypertension, pulmonary arterial and venous hypertension, congenital heart disease (with and without intracardiac shunting), valvular heart disease, idiopathic dilated cardiomyopathy, infectious and non-infectious myocarditis, stress cardiomyopathy (as seen associated with critical care illnesses, physical and emotional stress, and intracranial hemorrhage and stroke), septic cardiomyopathy, atrial and ventricular arrhythmias, endocarditis, pericarditis, damage to heart muscle, cardioplegia, cardiac arrest, acute myocardial infarction (AMI), myocardial ischemia-reperfusion injury, ventricular remodeling, concentric hypertrophy, eccentric hypertrophy and any other known cardiac condition.

In certain embodiments, a subject having or suspected of having a myocardial infarction can be administered a composition disclosed herein to ameliorate the conditions such as the symptoms or side effects of the cardiac condition. In certain embodiments, compositions disclosed herein that include an Fc-AAT fusion molecule and a pharmaceutically acceptable carrier can be used to reduce or prevent cardiac ventricular remodeling or reduce the effects of ischemia reperfusion. Methods for treating any cardiac condition disclosed herein can include administering a composition before, during or after a cardiac event. In certain embodiments, compositions can be administered to a subject for a period determined by health professional to have optimum benefit after a cardiac event has occurred in a subject. For example, a subject may be treated with a composition for up to one week, up to two weeks or more following an event. In certain embodiments, compositions administered to a subject described herein can be 5-fold, 10-fold, 100-fold or 1,000 fold less than using a commercially available AAT formulation (e.g. Aralast™, Zemaira™, Prolastin C™), such as 0.001 mg/kg to 10 mg/kg recombinant or Fc-AAT fusion molecule per dose.

Gastrointestinal Disorders

Some embodiments of the present invention include treating a subject having a gastrointestinal order or condition (e.g. intermittent, solitary or chronic condition) or inflammatory bowel disorder. In accordance with these embodiments, a subject having a gastrointestinal condition may have one or more of the following conditions including, but not limited to, inflammatory bowel disease (e.g. IBS or IBD), ulcerative colitis (UC), Crohn's disease (CD), systemic inflammatory response syndrome (SIRS), allergy-linked bowel disease, bowel disease linked to Type 1 diabetes, other colitis types (e.g. collagenous colitis, ischaemic colitis, diversion colitis, indeterminate colitis), Behcet's syndrome associated with inflammation of the bowels and other bowel disorders. In certain embodiments, symptoms or side effects of bowel disorders can be treated by compositions disclosed herein. For example, side effects of bowel disorders include, but are not limited to, skin manifestations, weight loss, colon shortening, intestinal mucosa, bowel or intestinal hyperpermeability can be ameliorated with a composition having an Fc-AAT fusion construct (e.g. hinge deletion or hinge truncation) and a pharmaceutically acceptable carrier. Certain embodiments can include treating a subject having a bowel disorder with compositions disclosed herein to reduce or prevent weight loss in a subject having the disorder. Compositions disclosed herein are supported by previous observations that Fc-AAT (IgG1) has anti-inflammatory activity superior to plasma-derived AAT demonstrated in a gastrointestinal mouse model and Fc-AAT3 (hinge deletion of Fc from IgG1) has comparable anti-inflammatory activities as Fc-AAT (IgG1).

Bacterial Conditions

Some embodiments of the present invention include treating a subject having a bacterial infection. Other embodiments can include administering a composition disclosed herein to prevent a bacterial infection in a subject. Bacterial infections contemplated herein can include, but are not limited to, Gram negative or Gram positive bacteria or mycobacterial organisms. Gram negative bacteria can include, but are not limited to, *N. gonorrhoeae*, *N. meningitidi*, *M. catarrhalis*, *H. influenzae*, *E. coli*, all *Klebsiela* spp., all *Enterobacter* spp., all *Serratia* spp, all *Salmonella* spp., *Proteus mirabilis*, *Proteus vulgaris*, all *Providencia* spp., all *Morganella* spp., *Pseudomonas aeruginosa*, all *Citrobacter* spp., all *Pasteurella* spp., all *Aeromonas* spp., *Pseudomonas cepacia*, all *Shigella* spp, *Stenotrophomonas maltophilia*, all *Acinetobacter* spp., all *Legionella* spp., *Y. enterocolitica*, other *Yersinoiiosis*, *H. ducreyeii*, all *Chlamyidia* spp., *Mycoplasma pneumonia*, *Mycoplasma hominis*, *Bacteroides fragilis*, *P. melaninogenica*, all *Moraxella* spp., all *Bortedella* spp., and *P. multocida*.

Mycobacteria contemplated herein can include, but are not limited to, *M. bovis*, *M. tuberculosis*, *Mycobacterium avium* complex (MAC) organisms, *M. intracellulare*, *M. avium*, *M. paratuberculosis*, leprosy causing (*M. leprae*, *M. flavascens*, *M. lepraemurium*) *M. microti*, *M. chelonei*, *M. africanum*, *M. marinium*, *M. buruli*, *M. fortuitum*, *M. haemophilum*, *M. kansasii*, *M. littorale*, *M. malmoense*, *M. marianum*, *M. simiae*, *M. szulgai*, *M. ulcerans*, *M. gordonae*, *M. gastri*, *M. phlei*, *M. nonchromogenicum*, *M. smegmatis*, *M. terrae*, *M. trivial*, *M. scrofulaceum*, *M. xenopi*, *M. gordonae*, *M. haemophilum*, *M. genavense*, *M. simiae*, *M. vaccae*.

Gram positive bacteria contemplated herein include, but are not limited to, *C. tetani*, *C. botulinum*, *C. diflicile*. Group A, B C. and G *Streptococcus*, *Streptococcus pneumonia*, *Streptococcus milleri* group, *Viridans streptococcus*, all *Listeria* spp., all *Staphylococcus* spp. *S. aureus* (MSSA), *S. aureus* (MRSA), *S. epidermidis*, *Enterococcus faecalis*, *Enterococcus faecium*, all *Clostridium* spp., *C. diptheriea*, *C. jeikium*, all *Rhodococcus* spp., all *Leukonostoc* spp. and *Bacillus anthracis* (e.g. that causes anthrax).

In certain embodiments, compositions disclosed herein can be used to treat a subject having a bacterial condition, reducing or preventing onset of a bacterial associated condition.

Yet other embodiments concern treating or reducing septic shock in a subject. Septic shock can be caused by systemic bacterial infection of a subject, for example, to bacterial endotoxins, such as Gram negative lipopolysaccharides. In certain embodiments, it is thought that nitric oxide overproduction contributes to septic shock. Reduction in NO production has been demonstrated to reduce symptoms of septic shock. In accordance with these embodiments, methods disclosed herein relate to treating septic shock by administering an AAT fusion molecule such as Fc-AAT. Some embodiments include administering an AAT fusion molecule in conjunction with other therapies, e.g., antibodies to proinflammatory cytokines etc. Or agents that reduce lipopolysaccharides, reduce tumor necrosis factor or interleukin-1 expression, or interleukin-1 receptor antagonist expression, or soluble TNF or IL-1 receptors. In certain embodiments, macrophages and endothelium can be cellular targets for inhibition of nitric oxide activity. To date, septic shock has eluded successful therapies.

Viral Conditions

Some embodiments of the present invention include treating a subject having a viral infection. Other embodiments herein can include administering a composition disclosed herein to prevent a viral infection from developing in a subject exposed to a virus. Viral infections contemplated herein can include, but are not limited to, Human Immunodeficiency Virus (HIV) AIDS, influenza virus (e.g. type A, B, C, influenza A H1N1, H1N2, H3N2, H9N2, H7N2, H10N7), Herpes zoster, Herpes simplex, human papilloma virus. Variola major virus (small pox), Lassa fever virus, avian flu, AIDS Related Complex, Chickenpox (Varicella), Cytomegalovirus (CMV), Colorado tick fever, Dengue fever, Ebola haemorrhagic fever, Hand, foot and mouth disease, Hepatitis, HPV, infectious mononucleosis, Mumps, Poliomyelitis, Progressive multifocal leukoencephalopathy, Rabies, Rubella, SARS, viral encephalitis, viral gastroenteritis, viral meningitis, West Nile disease, Yellow fever, Marburg haemorrhagic fever, Measles and other viral-related disorders.

Other embodiments disclosed herein concern reducing or preventing developing cancer attributed to infection by a virus by inhibiting viral replication and/or infection in a subject using compositions disclosed herein. Cancers induced by viruses can include, but are not limited to, Rous sarcoma induced cancer, human papilloma virus (HPV) induced cancer (e.g. cervical cancer), polyoma induced cancer, Hepatitis B virus induced cancer, fibrosarcoma, myxosarcoma, liposarcoma, chondrosarcoma, osteogenic sarcoma, angiosarcoma, chordoma, endotheliosarcoma, lymphangiosarcoma, lymphangioendothelio sarcoma, mesothelioma, synovioma, Ewing's tumor, leiomyosarcoma, rhabdomyosarcoma, rhabdosarcoma, colorectal carcinoma, pancreatic cancer, breast cancer, melanoma, prostate cancer, ovarian cancer, squamous cell carcinoma, basal cell carcinoma, sebaceous gland carcinoma, adenocarcinoma, sweat gland carcinoma, papillary carcinoma, hepatoma cystadenocarcinoma, papillary adenocarcinomas, bronchogenic carcinoma, medullary carcinoma, renal cell carcinoma, seminoma, bile duct carcinoma, cervical cancer, Wilms' tumor, embryonal carcinoma, lung carcinoma, choriocarcinoma, testicular tumor, bladder carcinoma, epithelial carcinoma, small cell lung carcinoma, craniopharyngioma, medulloblastoma, astroctoma, glioma, ependymoma, pinealoma, hemangioblastoma, acoustic neuroma, oligodendroglioma, meningioma neuroblastoma, retinoblastoma, myeloma, lymphoma, and leukemia. Yet other embodiments concern viral pneumonia and bronchial pneumonia.

In certain embodiments, compositions disclosed herein can be used to treat a subject having a viral infection, reducing or preventing onset of a viral associated condition. For example, compositions disclosed herein can be used to treat a subject having a viral infection to reduce transmission of the virus and reduce viral replication in the subject (e.g. influenza or other disease transmitted from subject to subject) thereby reducing subject to subject transmission.

Constructs of Various Peptides

Embodiments herein provide for rapidly generating and using AAT fusion molecules either full-length AAT or carboxyterminal peptides derived from AAT (e.g. a carboxyterminal peptide of AAT found in the last 80 amino acids of AAT or a carboxyterminal peptide of AAT found in the last 36 amino acids of AAT etc.).

In one embodiment of the present invention, a composition may include constructs for treating a subject in need of AAT therapy (e.g. mammalian derived AAT) for example, a series of peptides including carboxyterminal amino acid peptides corresponding to AAT and derivatives thereof. These peptides can include, pentapeptides including, FVFLM (SEQ ID NO:2), FVFAM (SEQ ID NO:3), FVALM (SEQ ID NO:4), FVFLA (SEQ ID NO:5), FLVFI (SEQ ID NO:6), FLMII (SEQ ID NO:7), FLFVL (SEQ ID NO:8), FLFVV (SEQ ID NO:9), FLFLI (SEQ ID NO: 10), FLFFI (SEQ ID NO: 11), FLMFI (SEQ ID NO: 12), FMLLI (SEQ ID NO: 13), FIIMI (SEQ ID NO: 14), FLFCI (SEQ ID NO: 15), FLFAV (SEQ ID NO: 16), FVYLI (SEQ ID NO: 17), FAFLM (18), AVFLM (SEQ ID NO: 19), and any combination thereof.

In other embodiments, AAT peptides contemplated for use in constructs, pharmaceutical compositions and methods herein are also intended to include any and all of those specific AAT peptides of SEQ ID NO: 1 or SEQ ID NO:33 (naturally-occurring AAT of 394 amino acids, the most common form is the M type with subtypes M1, M2, M3 etc. are also contemplated herein) associated with the carboxyterminal amino acids. All AAT polypeptides are contemplated of use in methods disclosed herein, that possess anti-inflammatory activity and/or immune regulatory activity. Any combination of consecutive amino acids simulating AAT or AAT-like activity may be used, such as amino acids ranging from 315-394, amino acids ranging from 325-384, 358-394, 340-380 etc. In addition, combinations of consecutive amino acid sequences such as 5-mers, 10-mers, 15-mers, 20-mers, 25-mers, 30-mers, 35-mers etc. of the carboxyterminus can also be used. For example, any combinations of consecutive amino acids of 5-mers, 10-mers, 15-mers, 20-mers from SEQ ID NO: 1 AAs 314-394 can be used in developing or purifying a construct contemplated herein.

Certain embodiments concern generating a recombinant fusion protein including linking an entire AAT molecule (e.g. SEQ ID NO: 1 or 33) or a peptide molecule derived from the carboxyterminal amino acid region of AAT, to an IgG (e.g. Fc or mutant Fc for example, to reduce the hinge region) or fragment thereof. One common form of AAT is denoted by SEQ ID NO:33. One construct contemplated herein is referenced as SEQ ID NO:32 (e.g. full-length AAT, a leader sequence and an Fc portion/fragment of an immunoglobulin molecule). These constructs can be used in dimer form or as a monomeric form in compositions disclosed herein. In accordance with these embodiments, a pharmaceutically acceptable composition can include a dimer of Fc-AAT or a monomer of Fc-AAT or AAT cleaved from the Fc or combinations thereof, and a pharmaceutically acceptable excipient. In addition, point mutations can be made in the Fc region to reduce the flexibility of the hinge region and generate novel Fc-AAT molecules. In other embodiments, the hinge region of Fc derived from IgG1, IgG2, IgG3 or IgG4 can be deleted or truncated prior to linking an Fc to AAT or AAT peptide. Fc can be further manipulated to modify the region to reduce receptor interactions and enhance Fc-AAT construct activity. For example, point mutations can be made in the Fc region to reduce the flexibility of the hinge region or deletions or additions to this region can be made to affect secondary interactions regarding this region or that alter tertiary structure of the fusion molecule to generate novel Fc-AAT molecules.

```
SEQ ID NO: 33:
EDPQGDAAQKTDTSHHDQDHPTFNKITPNLAEFAFSLYRQLAHQSNSTNI

FFSPVSIATAFAMLSLGTKADTHDEILEGLNFNLTEIPEAQIHEGFQELL

RTLNQPDSQLQLTTGNGLFLSEGLKLVDKFLEDVKKLYHSEAFTVNFGDT

EEAKKQINDYVEKGTQGKIVDLVKELDRDTVFALVNYIFFKGKWERPFEV

KDTEEEDFHVDQATTVKVPMMKRLGMFNIQHCKKLSSWVLLMKYLGNATA

IFFLPDEGKLQHLENELTHDIITKFLENEDRRSASLHLPKLSITGTYDLK

SVLGQLGITKVFSNGADLSGVTEEAPLKLSKAVHKAVLTIDEKGTEAAGA

MFLEAIPMSIPPEVKFNKPFVFLMIEQNTKSPLFMG KVVNPTQK
```

In other embodiments, AAT protease binding domain can be mutated in order to reduce or eliminate the protease function of the molecule and not inhibit elastase activity; these molecules can be used in any construct contemplated herein such as a Fc-AAT mutant. In certain embodiments, a mutated AAT can be used to generate an AAT construct by methods disclosed herein. In other embodiments, a mutated molecule (e.g. having reduced or essentially no protease activity) retains its anti-inflammatory effects and/or immunomodulatory effects and can be used as an anti-inflammatory molecule in a subject having a need for AAT therapy. One skilled in the art would understand a non-protease binding domain of AAT as well as what is termed the carboxyterminal last 80 amino acids of naturally-occurring AAT.

In each of the above-recited methods, α1-antitrypsin or carboxyterminal peptide derivatives thereof are contemplated for use in a composition herein. These peptide derivatives may include but are not limited to amino acid peptides containing the last 80 carboxyterminal derived amino acids of AAT, GITKVFSNGA (SEQ ID NO:20), DLSGVTEEAP (SEQ ID NO:21), LKLSKAVHKA (SEQ ID NO:22), VLTIDEKGTE (SEQ ID NO:23), AAGAMFLEAI (SEQ ID NO:24), PMSIPPEVKF (SEQ ID NO:25), NKPFVFLMIE (SEQ ID NO:26), QNTKSPLFMG (SEQ ID NO:27), KVVNPTQK (SEQ ID NO:28), LEAIPMSIPPEVKFNKPFVFLM (SEQ ID NO:29); and LEAIPMSIPPEVKFNKPFVF (SEQ ID NO:30), GADLSGVTEEAPLKLSKAVHKAVLTIDEKGTEAAGAMFLEAIPMSIPPEVKFNKPFVFLMIEQNTKSPLFMGKVVNPTQK (SEQ ID NO:31), SEQ ID NO:34 or any combination thereof. In certain embodiments, the carboxyterminal peptides of AAT are 80%, or 85%, or 90%, or 95%, or 99% identical to the naturally occurring M type amino acid sequence identified by SEQ ID NO. 33. In certain embodiments, about 3, or about 4, or about 5 amino acids can vary (e.g. point mutations) from an 80-mer from the carboxy terminal of M type sequence.

Certain embodiments include compositions of the fusion molecule SEQ ID NO: 32 or other Fc-AAT fusion molecule with or without an Fc hinge region where an Fc region originates from IgG1, IgG2, IgG3 or IgG4 or even IgD. In accordance with these embodiments, the compositions can be a pharmaceutical composition.

In certain embodiments, compositions of recombinant AAT or AAT-derived carboxyterminal peptides capable of binding to SEC receptors or compositions with AAT-like activities may be administered to a subject in need thereof.

As disclosed herein the carboxy terminal region of AAT includes the last 80 amino acids (SEQ ID NO:31) or other human AAT molecule or other naturally occurring AAT molecule. In other embodiments, peptides derived from AAT can include 5-mers, 10-mers, 20-mers, 25-mers, 30-mers, 35-mers, 40-mers, 50-mers, and up to an 80 mer of an AAT molecule wherein any of the contemplated peptides have no significant serine protease inhibitor activity, are derived from the carboxyterminus of AAT and are capable of being used for treating subjects undergoing radiation or subjects exposed to large doses of radiation by accident or other cause.

In one embodiment of the present invention, a construct may include compounds that engage or associate with the SEC receptor. In some of the recited methods, an AAT-mutant or AAT derived peptide (e.g. mammalian derived) having no significant serine protease inhibitor activity contemplated for use within the methods of the present invention can include a series of peptides including carboxyterminal amino acid peptides corresponding to AAT. In addition, combinations of amino acid 5-mers or 10-mers or 20-mers or 30-mers or more can also be used. For example, one or more 5-mers or 10-mers or 20-mers etc. can include consecutive amino acids starting from AA 315 and ending with AA 394 of naturally occurring AAT represented as SEQ ID NO: 1. As contemplated herein, the later half of a sequence toward the carboxy end is referred to as the carboxyterminus. In certain embodiments, the carboxyl domain of AAT going backwards from the carboxyl terminus is defined as those amino acids most conserved among the difference species and do not participate in the protease binding domain of AAT. In addition, in other embodiments, AAT protease binding domain can be mutated in order to reduce or eliminate the protease function of the molecule and this molecule can be used in any composition contemplated herein. In other embodiments, a mutated molecule can retain its anti-inflammatory and/or immunomodulatory effects. Also contemplated herein is that the carboxyl domain is the non-protease binding domain. One skilled in the art would understand a non-protease binding domain of AAT.

In each of the above-recited methods, compositions herein may include peptides derived from the carboxyterminus of AAT. In certain embodiments, AAT-associated molecules used in the methods and compositions herein can include, but are not limited to, compositions of SEQ ID NO: 1, naturally occurring AAT (394 AA length molecule making up approximately 90% of AAT isolated from serum), other AAT M-types or other AAT molecules.

```
Grid:
Underline= restriction site
No marking= human AAT molecule

Fc= shaded

Hinge region= italic and bold (Lucida console)
AAT-Fc2 (pCAG.neo-hAAT-hIgG1 Fc) (nucleic acid sequence to SEQ ID NO: 32)
Artificial: derived from human alpha-1 antitrypsin and human Fc fragment of IgG1)
< DNA sequence > dsDNA 1977 bp
                                                                  SEQ ID NO: 47
GAATTCGCCA CCATGCCGTC TTCTGTCTCG TGGGGCATCC TCCTGCTGGC AGGCCTGTGC        60

TGCCTGGTCC CTGTCTCCCT GGCTGAGGAT CCCCAGGGAG ATGCTGCCCA GAAGACAGAT       120

ACATCCACC ACGATCAGGA TCACCCAACC TTCAACAAGA TCACCCCCAA CCTGGCTGAG       180

TTCGCCTTCA GCCTATACCG CCAGCTGGCA CACCAGTCCA ACAGCACCAA TATCTTCTTC       240
```

```
TCCCCAGTGA GCATCGCTAC AGCCTTTGCA ATGCTCTCCC TGGGGACCAA GGCTGACACT       300

CACGATGAAA TCCTGGAGGG CCTGAATTTC AACCTCACGG AGATTCCGGA GGCTCAGATC       360

CATGAAGGCT TCCAGGAACT CCTCCGTACC CTCAACCAGC CAGACAGCCA GCTCCAGCTG       420

ACCACCGGCA ATGGCCTGTT CCTCAGCGAG GGCCTGAAGC TAGTGGATAA GTTTTTGGAG       480

GATGTTAAAA AGTTGTACCA CTCAGAAGCC TTCACTGTCA ACTTCGGGGA CACCGAAGAG       540

GCCAAGAAAC AGATCAACGA TTACGTGGAG AAGGGTACTC AAGGGAAAAT TGTGGATTTG       600

GTCAAGGAGC TTGACAGAGA CACAGTTTTT GCTCTGGTGA ATTACATCTT CTTTAAAGGC       660

AAATGGGAGA GACCCTTTGA AGTCAAGGAC ACCGAGGAAG AGGACTTCCA CGTGGACCAG       720

GCGACCACCG TGAAGGTGCC TATGATGAAG CGTTTAGGCA TGTTTAACAT CCAGCACTGT       780

AAGAAGCTGT CCAGCTGGGT GCTGCTGATG AAATACCTGG GCAATGCCAC CGCCATCTTC       840

TTCCTGCCTG ATGAGGGGAA ACTACAGCAC CTGGAAAATG AACTCACCCA CGATATCATC       900

ACCAAGTTCC TGGAAAATGA AGACAGAAGG TCTGCCAGCT TACATTTACC CAAACTGTCC       960

ATTACTGGAA CCTATGATCT GAAGAGCGTC CTGGGTCAAC TGGGCATCAC TAAGGTCTTC      1020

AGCAATGGGG CTGACCTCTC CGGGGTCACA GAGGAGGCAC CCCTGAAGCT CTCCAAGGCC      1080

GTGCATAAGG CTGTGCTGAC CATCGACGAG AAAGGGACTG AAGCTGCTGG GGCCATGTTT      1140

TTAGAGGCCA TACCCATGTC TATCCCCCCC GAGGTCAAGT TCAACAAACC CTTTGTCTTC      1200

TTAATGATTG AACAAAATAC CAAGTCTCCC CTCTTCATGG AAAAGTGGT GAATCCCACC       1260

CAAAAAACGC GTGAGCCCAA ATCTTGTGAC AAAACTCACA CATGCCCACC GTGCCCAGCA      1320

CCTGAACTCC TGGGGGGACC GTCAGTCTTC CTCTTCCCCC CAAAACCCAA GGACACCCTC      1380

ATGATCTCCC GGACCCCTGA GGTCACATGC GTGGTGGTGG ACGTGAGCCA CGAAGACCCT      1440

GAGGTCAAGT TCAACTGGTA CGTGGACGGC GTGGAGGTGC ATAATGCCAA GACAAAGCCG      1500

CGGGAGGAGC AGTACAACAG CACGTACCGT GTGGTCAGCG TCCTCACCGT CCTGCACCAG      1560

GACTGGCTGA ATGGCAAGGA GTACAAGTGC AAGGTCTCCA ACAAAGCCCT CCCAGCCCCC      1620

ATCGAGAAAA CCATCTCCAA AGCCAAAGGG CAGCCCCGAG AACCACAGGT GTACACCCTG      1680

CCCCCATCCC GGGATGAGCT GACCAAGAAC CAGGTCAGCC TGACCTGCCT GGTCAAAGGC      1740

TTCTATCCCA GCGACATCGC CGTGGAGTGG GAGAGCAATG GGCAGCCGGA GAACAACTAC      1800

GTGGACAAGA GCAGGTGGCA GCAGGGGAAC GTCTTCTCAT GCTCCGTGAT GCATGAGGCT      1920

CTGCACAACC ACTACACGCA GAAGAGCCTC TCCCTGTCTC CGGGTAAATG AGGATCT        1977

AAT-Fc2 < Amino acid sequence >
652 a.a.
                                                                 SEQ ID NO: 32
MPSSVSWGIL LLAGLCCLVP VSLAEDPQGD AAQKTDTSHH DQDHPTFNKI TPNLAEFAFS        60

LYRQLAHQSN STNIFFSPVS IATAFAMLSL GTKADTHDEI LEGLNFNLTE IPEAQIHEGF       120

QELLRTLNQP DSQLQLTTGN GLFLSEGLKL VDKFLEDVKK LYHSEAFTVN FGDTEEAKKQ      180

INDYVEKGTQ GKIVDLVKEL DRDTVFALVN YIFFKGKWER PFEVKDTEEE DFHVDQATTV      240

KVPMMKRLGM FNIQHCKKLS SWVLLMKYLG NATAIFFLPD EGKLQHLENE LTHDIITKFL      300

ENEDRRSASL HLPKLSITGT YDLKSVLGQL GITKVFSNGA DLSGVTEEAP LKLSKAVHKA      360

VLTIDEKGTE AAGAMFLEAI PMSIPPEVKF NKPFVFLMIE QNTKSPLFMG KVVNPTQKTR      420
```

*EPKSCDKTHT CPPCPAPELL* GGPSVFLFPP KPKDTLMISR TPEVTCVVVD VSHEDPEVKF        480

NWYVDGVEVH NAKTKPREEQ YNSTYRVVSV LTVLHQDWLN GKEYKCKVSN KALPAPIEKT        540

ISKAKGQPRE PQVYTLPPSR DELTKNQVSL TCLVKGFYPS DIAVEWESNG QPENNYKTTP        600

PVLDSDGSFF LYSKLTVDKS RWQQGNVFSC SVMHEALHNH YTQKSLSLSP GK               652

AAT-Fc3 (pCAG.neo-hAAT-hIgG1 Fc; hinge deletion)
(Artificial: derived from human alpha-1 antitrypsin and human Fc fragment
of IgG1 hinge deletion)
< DNA sequence > dsDNA 1950 bp

SEQ ID NO: 48

```
GAATTCGCCA CCATGCCGTC TTCTGTCTCG TGGGGCATCC TCCTGCTGGC AGGCCTGTGC        60

TGCCTGGTCC CTGTCTCCCT GGCTGAGGAT CCCCAGGGAG ATGCTGCCCA AGAAGACAGAT     120

ACATCCCACC ACGATCAGGA TCACCCAACC TTCAACAAGA TCACCCCCAA CCTGGCTGAG      180

TTCGCCTTCA GCCTATACCG CCAGCTGGCA CACCAGTCCA ACAGCACCAA TATCTTCTTC      240

TCCCCAGTGA GCATCGCTAC AGCCTTTGCA ATGCTCTCCC TGGGGACCAA GGCTGACACT      300

CACGATGAAA TCCTGGAGGG CCTGAATTTC AACCTCACGG AGATTCCGGA GGCTCAGATC      360

CATGAAGGCT TCCAGGAACT CCTCCGTACC CTCAACCAGC CAGACAGCCA GCTCCAGCTG      420

ACCACCGGCA ATGGCCTGTT CCTCAGCGAG GGCCTGAAGC TAGTGGATAA GTTTTTGGAG      480

GATGTTAAAA AGTTGTACCA CTCAGAAGCC TTCACTGTCA ACTTCGGGGA CACCGAAGAG      540

GCCAAGAAAC AGATCAACGA TTACGTGGAG AAGGGTACTC AAGGGAAAAT TGTGGATTTG      600

GTCAAGGAGC TTGACAGAGA CACAGTTTTT GCTCTGGTGA ATTACATCTT CTTTAAAGGC      660

AAATGGGAGA GACCCTTTGA AGTCAAGGAC ACCGAGGAAG AGGACTTCCA CGTGGACCAG      720

GCGACCACCG TGAAGGTGCC TATGATGAAG CGTTTAGGCA TGTTTAACAT CCAGCACTGT      780

AAGAAGCTGT CCAGCTGGGT GCTGCTGATG AAATACCTGG GCAATGCCAC CGCCATCTTC      840

TTCCTGCCTG ATGAGGGGAA ACTACAGCAC CTGGAAAATG AACTCACCCA CGATATCATC      900

ACCAAGTTCC TGGAAAATGA AGACAGAAGG TCTGCCAGCT TACATTTACC CAAACTGTCC      960

ATTACTGGAA CCTATGATCT GAAGAGCGTC CTGGGTCAAC TGGGCATCAC TAAGGTCTTC     1020

AGCAATGGGG CTGACCTCTC CGGGGTCACA GAGGAGGCAC CCCTGAAGCT CTCCAAGGCC     1080

GTGCATAAGG CTGTGCTGAC CATCGACGAG AAAGGGACTG AAGCTGCTGG GGCCATGTTT     1140

TTAGAGGCCA TACCCATGTC TATCCCCCCC GAGGTCAAGT TCAACAAACC CTTTGTCTTC     1200

TTAATGATTG AACAAAATAC CAAGTCTCCC CTCTTCATGG GAAAAGTGGT GAATCCCACC     1260

CAAAAAACGC GTACATGCCC ACCGTGCCCA GCACCTGAAC TCCTGGGGGG ACCGTCAGTC     1320

TTCCTCTTCC CCCCAAAACC CAAGGACACC CTCATGATCT CCCGGACCCC TGAGGTCACA     1380

TGCGTGGTGG TGGACGTGAG CCACGAAGAC CCTGAGGTCA AGTTCAACTG GTACGTGGAC     1440

GGCGTGGAGG TGCATAATGC CAAGACAAAG CCGCGGGAGG AGCAGTACAA CAGCACGTAC     1500

CGTGTGGTCA GCGTCCTCAC CGTCCTGCAC CAGGACTGGC TGAATGGCAA GGAGTACAAG     1560

TGCAAGGTCT CCAACAAAGC CCTCCCAGCC CCCATCGAGA AAACCATCTC CAAAGCCAAA     1620

GGGCAGCCCC GAGAACCACA GGTGTACACC CTGCCCCCAT CCCGGGATGA GCTGACCAAG     1680

AACCAGGTCA GCCTGACCTG CCTGGTCAAA GGCTTCTATC CCAGCGACAT CGCCGTGGAG     1740

TGGGAGAGCA ATGGGCAGCC GGAGAACAAC TACAAGACCA CGCCTCCCGT GCTGGACTCC     1800
```

-continued

```
GACGGCTCCT TCTTCCTCTA CAGCAAGCTC ACCGTGGACA AGAGCAGGTG GCAGCAGGGG      1860

AACGTCTTCT CATGCTCCGT GATGCATGAG GCTCTGCACA ACCACTACAC GCAGAAGAGC      1920

CTCTCCCTGT CTCCGGGTAA ATGAGGATCT                                       1950
```

AAT-Fc3 <Amino acid sequence > new sequence 49 (Artificial: derived from human alpha-1 antitrypsin and human Fc fragment of IgG1)
643 a.a.

SEQ ID NO: 49

```
MPSSVSWGIL LLAGLCCLVP VSLAEDPQGD AAQKTDTSHH DQDHPTFNKI TPNLAEFAFS       60
LYRQLAHQSN STNIFFSPVS IATAFAMLSL GTKADTHDEI LEGLNFNLTE IPEAQIHEGF      120
QELLRTLNQP DSQLQLTTGN GLFLSEGLKL VDKFLEDVKK LYHSEAFTVN FGDTEEAKKQ      180
INDYVEKGTQ GKIVDLVKEL DRDTVFALVN YIFFKGKWER PFEVKDTEEE DFHVDQATTV      240
KVPMMKRLGM FNIQHCKKLS SWVLLMKYLG NATAIFFLPD EGKLQHLENE LTHDIITKFL      300
ENEDRRSASL HLPKLSITGT YDLKSVLGQL GITKVFSNGA DLSGVTEEAP LKLSKAVHKA      360
VLTIDEKGTE AAGAMFLEAI PMSIPPEVKF NKPFVFLMIE QNTKSPLFMG KVVNPTQKTR      420
TCPPCPAPEL LGGPSVFLFP PKPKDTLMIS RTPEVTCVVV DVSHEDPEVK FNWYVDGVEV      480
HNAKTKPREE QYNSTYRVVS VLTVLHQDWL NGKEYKCKVS NKALPAPIEK TISKAKGQPR      540
EPQVYTLPPS RDELTKNQVS LTCLVKGFYP SDIAVEWESN GQPENNYKTT PPVLDSDGSF      600
FLYSKLTVDK SRWQQGNVFS CSVMHEALHN HYTQKSLSLS PGK                        643
```

AAT-Fc4 (pCAG.neo-hAAT-hIgG2 Fc, intact) >
(Artificial: derived from human alpha-1 antitrypsin and human Fc fragment of IgG2)
< DNA sequence > dsDNA 1962 bp

SEQ ID NO: 50

```
GAATTCGCCA CCATGCCGTC TTCTGTCTCG TGGGGCATCC TCCTGCTGGC AGGCCTGTGC       60
TGCCTGGTCC CTGTCTCCCT GGCTGAGGAT CCCCAGGGAG ATGCTGCCCA AAAGACAGAT      120
ACATCCCACC ACGATCAGGA TCACCCAACC TTCAACAAGA TCACCCCCAA CCTGGCTGAG      180
TTCGCCTTCA GCCTATACCG CCAGCTGGCA CACCAGTCCA ACAGCACCAA TATCTTCTTC      240
TCCCCAGTGA GCATCGCTAC AGCCTTTGCA ATGCTCTCCC TGGGGACCAA GGCTGACACT      300
CACGATGAAA TCCTGGAGGG CCTGAATTTC AACCTCACGG AGATTCCGGA GGCTCAGATC      360
CATGAAGGCT TCCAGGAACT CCTCCGTACC CTCAACCAGC CAGACAGCCA GCTCCAGCTG      420
ACCACCGGCA ATGGCCTGTT CCTCAGCGAG GGCCTGAAGC TAGTGGATAA GTTTTTGGAG      480
GATGTTAAAA AGTTGTACCA CTCAGAAGCC TTCACTGTCA ACTTCGGGGA CACCGAAGAG      540
GCCAAGAAAC AGATCAACGA TTACGTGGAG AAGGGTACTC AAGGGAAAAT TGTGGATTTG      600
GTCAAGGAGC TTGACAGAGA CACAGTTTTT GCTCTGGTGA ATTACATCTT CTTTAAAGGC      660
AAATGGGAGA GACCCTTTGA AGTCAAGGAC ACCGAGGAAG AGGACTTCCA CGTGGACCAG      720
GCGACCACCG TGAAGGTGCC TATGATGAAG CGTTTAGGCA TGTTTAACAT CCAGCACTGT      780
AAGAAGCTGT CCAGCTGGGT GCTGCTGATG AAATACCTGG GCAATGCCAC CGCCATCTTC      840
TTCCTGCCTG ATGAGGGGAA ACTACAGCAC CTGGAAAATG AACTCACCCA CGATATCATC      900
ACCAAGTTCC TGGAAAATGA AGACAGAAGG TCTGCCAGCT TACATTTACC CAAACTGTCC      960
ATTACTGGAA CCTATGATCT GAAGAGCGTC CTGGGTCAAC TGGGCATCAC TAAGGTCTTC     1020
AGCAATGGGG CTGACCTCTC CGGGGTCACA GAGGAGGCAC CCTGAAGCT CTCCAAGGCC      1080
GTGCATAAGG CTGTGCTGAC CATCGACGAG AAAGGGACTG AAGCTGCTGG GGCCATGTTT     1140
```

```
TTAGAGGCCA TACCCATGTC TATCCCCCCC GAGGTCAAGT TCAACAAACC CTTTGTCTTC        1200

TTAATGATTG AACAAAATAC CAAGTCTCCC CTCTTCATGG AAAAGTGGT GAATCCCACC         1260

CAAAAAACGC GTCGCAAATG TTGTGTCGAG TGCCCACCGT GCCCAGCACC ACCTGTGGCA        1320

GGACCGTCAG TCTTCCTCTT CCCCCCAAAA CCCAAGGACA CCCTCATGAT CTCCCGGACC        1380

CCTGAGGTCA CATGCGTGGT GGTGGACGTG AGCCACGAAG ACCCTGAGGT CAAGTTCAAC        1440

TGGTACGTGG ACGGGGTGGA GGTGCATAAT GCCAAGACAA AGCCGCGGGA GGAGCAGTAC        1500

AACAGCACGT ACCGTGTGGT CAGCGTCCTC ACCGTCCTGC ACCAGGACTG GCTGAATGGC        1560

AAGGAGTACA AGTGCAAGGT CTCCAACAAA GCCCTCCCAG CCCCCATCGA GAAAACCATC        1620

TCCAAAGCCA AAGGGCAGCC CCGAGAACCA CAGGTGTACA CCCTGCCCCC ATCCCGGGAT        1680

GAGCTGACCA AGAACCAGGT CAGCCTGACC TGCCTGGTCA AAGGCTTCTA TCCCAGCGAC        1740

ATCGCCGTGG AGTGGGAGAG CAATGGGCAG CCGGAGAACA ACTACAAGAC CACGCCTCCC        1800

GTGCTGGACT CCGACGGCTC CTTCTTCCTC TACAGCAAGC TCACCGTGGA CAAGAGCAGG        1860

TGGCAGCAGG GGAACGTCTT CTCATGCTCC GTGATGCATG AGGCTCTGCA CAACCACTAC        1920

ACGCAGAAGA GCCTCTCCCT GTCTCCGGGT AAATGAGGAT CT                          1920
```

AAT-Fc4 < Amino acid sequence >(Artificial: derived from human alpha-1
antitrypsin and human Fc fragment of IgG2)
647 a.a.

```
                                                              SEQ ID NO: 51
MPSSVSWGIL LLAGLCCLVP VSLAEDPQGD AAQKTDTSHH DQDHPTFNKI TPNLAEFAFS        60

LYRQLAHQSN STNIFFSPVS IATAFAMLSL GTKADTHDEI LEGLNFNLTE IPEAQIHEGF        120

QELLRTLNQP DSQLQLTTGN GLFLSEGLKL VDKFLEDVKK LYHSEAFTVN FGDTEEAKKQ        180

INDYVEKGTQ GKIVDLVKEL DRDTVFALVN YIFFKGKWER PFEVKDTEEE DFHVDQATTV        240

KVPMMKRLGM FNIQHCKKLS SWVLLMKYLG NATAIFFLPD EGKLQHLENE LTHDIITKFL        300

ENEDRRSASL HLPKLSITGT YDLKSVLGQL GITKVFSNGA DLSGVTEEAP LKLSKAVHKA        360

VLTIDEKGTE AAGAMFLEAI PMSIPPEVKF NKPFVFLMIE QNTKSPLFMG KVVNPTQKTR        420

RKCCVECPPC PAPPVAGPSV FLFPPKPKDT LMISRTPEVT CVVVDVSHED PEVKFNWYVD        480

GVEVHNAKTK PREEQYNSTY RVVSVLTVLH QDWLNGKEYK CKVSNKALPA PIEKTISKAK        540

GQPREPQVYT LPPSRDELTK NQVSLTCLVK GFYPSDIAVE WESNGQPENN YKTTPPVLDS        600

DGSFFLYSKL TVDKSRWQQG NVFSCSVMHE ALHNHYTQKS LSLSPGK                     647
```

AAT-Fc5 (pCAG.neo-hAAT-hIgG3 Fc, intact) (Artificial: derived from human
alpha-1 antitrypsin and human Fc fragment of IgG3)
<DNA sequence > dsDNA 1995 bp

```
                                                              SEQ ID NO: 52
GAATTCGCCA CCATGCCGTC TTCTGTCTCG TGGGGCATCC TCCTGCTGGC AGGCCTGTGC        60

TGCCTGGTCC CTGTCTCCCT GGCTGAGGAT CCCCAGGGAG ATGCTGCCCA AGAGACAGAT        120

ACATCCCACC ACGATCAGGA TCACCCAACC TTCAACAAGA TCACCCCCAA CCTGGCTGAG        180

TTCGCCTTCA GCCTATACCG CCAGCTGGCA CACCAGTCCA ACAGCACCAA TATCTTCTTC        240

TCCCCAGTGA GCATCGCTAC AGCCTTTGCA ATGCTCTCCC TGGGGACCAA GGCTGACACT        300
```

-continued

```
CACGATGAAA TCCTGGAGGG CCTGAATTTC AACCTCACGG AGATTCCGGA GGCTCAGATC        360

CATGAAGGCT TCCAGGAACT CCTCCGTACC CTCAACCAGC CAGACAGCCA GCTCCAGCTG        420

ACCACCGGCA ATGGCCTGTT CCTCAGCGAG GGCCTGAAGC TAGTGGATAA GTTTTTGGAG        480

GATGTTAAAA AGTTGTACCA CTCAGAAGCC TTCACTGTCA ACTTCGGGGA CACCGAAGAG        540

GCCAAGAAAC AGATCAACGA TTACGTGGAG AAGGGTACTC AAGGGAAAAT TGTGGATTTG        600

GTCAAGGAGC TTGACAGAGA CACAGTTTTT GCTCTGGTGA ATTACATCTT CTTTAAAGGC        660

AAATGGGAGA GACCCTTTGA AGTCAAGGAC ACCGAGGAAG AGGACTTCCA CGTGGACCAG        720

GCGACCACCG TGAAGGTGCC TATGATGAAG CGTTTAGGCA TGTTTAACAT CCAGCACTGT        780

AAGAAGCTGT CCAGCTGGGT GCTGCTGATG AAATACCTGG GCAATGCCAC CGCCATCTTC        840

TTCCTGCCTG ATGAGGGGAA ACTACAGCAC CTGGAAAATG AACTCACCCA CGATATCATC        900

ACCAAGTTCC TGGAAAATGA AGACAGAAGG TCTGCCAGCT TACATTTACC CAAACTGTCC        960

ATTACTGGAA CCTATGATCT GAAGAGCGTC CTGGGTCAAC TGGGCATCAC TAAGGTCTTC        1020

AGCAATGGGG CTGACCTCTC CGGGGTCACA GAGGAGGCAC CCCTGAAGCT CTCCAAGGCC        1080

GTGCATAAGG CTGTGCTGAC CATCGACGAG AAAGGGACTG AAGCTGCTGG GGCCATGTTT        1140

TTAGAGGCCA TACCCATGTC TATCCCCCCC GAGGTCAAGT TCAACAAACC CTTTGTCTTC        1200

TTAATGATTG AACAAAATAC CAAGTCTCCC CTCTTCATGG GAAAAGTGGT GAATCCCACC        1260

CAAAAAACGC GTCCATGCCC ACGGTGCCCA GAGCCCAAAT CTTGTGACAC ACCTCCCCCG      1320

TGCCCAAGGT GCCCAGCACC TGAACTCCTG GGGGGACCGT CAGTCTTCCT CTTCCCCCCA        1380

AAACCCAAGG ACACCCTCAT GATCTCCCGG ACCCCTGAGG TCACATGCGT GGTGGTGGAC        1440

GTGAGCCACG AAGACCCTGA GGTCAAGTTC AACTGGTACG TGGACGGCGT GCAGGTGCAT        1500

AATGCCAAGA CAAAGCCGCG GGAGGACCAG TACAACAGCA CGTACCGTGT GGTCAGCGTC        1560

CTCACCGTCC TGCACCAGGA CTGGCTGAAT GGCAAGGAGT ACAAGTGCAA GGTCTCCAAC        1620

AAAGCCCTCC CAGCCCCCAT CGAGAAAACC ATCTCCAAAG CCAAAGGGCA GCCCCGAGAA        1680

CCACAGGTGT ACACCCTGCC CCCATCCCGG GATGAGCTGA CCAAGAACCA GGTCAGCCTG        1740

ACCTGCCTGG TCAAAGGCTT CTATCCCAGC GACATCGCCG TGGAGTGGGA GAGCAATGGG        1800

CAGCCGGAGA ACAACTACAA GACCACGCCT CCCGTGCTGG ACTCCGACGG CTCCTTCTTC        1860

CTCTACAGCA AGCTCACCGT GGACAAGAGC AGGTGGCAGC AGGGGAACGT CTTCTCATGC        1920

TCCGTGATGC ATGAGGCTCT GCACAACCAC TACACGCAGA AGAGCCTCTC CCTGTCTCCG        1980

GGTAAATGAG GATCT                                                      1995
```

AAT-Fc5 < Amino acid sequence >(Artificial: derived from human alpha-1
antitrypsin and human Fc fragment of IgG3)
658 a.a.

SEQ ID NO: 53

```
MPSSVSWGIL LLAGLCCLVP VSLAEDPQGD AAQKTDTSHH DQDHPTFNKI TPNLAEFAFS         60

LYRQLAHQSN STNIFFSPVS IATAFAMLSL GTKADTHDEI LEGLNFNLTE IPEAQIHEGF        120

QELLRTLNQP DSQLQLTTGN GLFLSEGLKL VDKFLEDVKK LYHSEAFTVN FGDTEEAKKQ        180

INDYVEKGTQ GKIVDLVKEL DRDTVFALVN YIFFKGKWER PFEVKDTEEE DFHVDQATTV        240

KVPMMKRLGM FNIQHCKKLS SWVLLMKYLG NATAIFFLPD EGKLQHLENE LTHDIITKFL       300
```

```
ENEDRRSASL HLPKLSITGT YDLKSVLGQL GITKVFSNGA DLSGVTEEAP LKLSKAVHKA      360

VLTIDEKGTE AAGAMFLEAI PMSIPPEVKF NKPFVFLMIE QNTKSPLFMG KVVNPTQKTR   420

*PCPRCPEPKS CDTPPPCPRC PAPELL*GGPS VFLFPPKPKD TLMISRTPEV TCVVVDVSHE    480

DPEVKFNWYV DGVEVHNAKT KPREEQYNST YRVVSVLTVL HQDWLNGKEY KCKVSNKALP     540

APIEKTISKA KGQPREPQVY TLPPSRDELT KNQVSLTCLV KGFYPSDIAV EWESNGQPEN     600

NYKTTPPVLD SDGSFFLYSK LTVDKSRWQQ GNVFSCSVMH EALHNHYTQK SLSLSPGK       658

AAT-Fc6 (pCAG.neo-hAAT-hIgG4 Fc, intact) Artificial: derived from human
alpha-1 antitrypsin and human Fc fragment of IgG4)
<DNA sequence > dsDNA 1965 bp
                                                               SEQ ID NO: 54
GAATTCGCCA CCATGCCGTC TTCTGTCTCG TGGGGCATCC TCCTGCTGGC AGGCCTGTGC    60

TGCCTGGTCC CTGTCTCCCT GGCTGAGGAT CCCCAGGGAG ATGCTGCCCA GAAGACAGAT     120

ACATCCCACC ACGATCAGGA TCACCCAACC TTCAACAAGA TCACCCCCAA CCTGGCTGAG     180

TTCGCCTTCA GCCTATACCG CCAGCTGGCA CACCAGTCCA ACAGCACCAA TATCTTCTTC     240

TCCCCAGTGA GCATCGCTAC AGCCTTTGCA ATGCTCTCCC TGGGGACCAA GGCTGACACT     300

CACGATGAAA TCCTGGAGGG CCTGAATTTC AACCTCACGG AGATTCCGGA GGCTCAGATC     360

CATGAAGGCT TCCAGGAACT CCTCCGTACC CTCAACCAGC CAGACAGCCA GCTCCAGCTG     420

ACCACCGGCA ATGGCCTGTT CCTCAGCGAG GGCCTGAAGC TAGTGGATAA GTTTTTGGAG     480

GATGTTAAAA AGTTGTACCA CTCAGAAGCC TTCACTGTCA ACTTCGGGGA CACCGAAGAG     540

GCCAAGAAAC AGATCAACGA TTACGTGGAG AAGGGTACTC AAGGGAAAAT TGTGGATTTG     600

GTCAAGGAGC TTGACAGAGA CACAGTTTTT GCTCTGGTGA ATTACATCTT CTTTAAAGGC     660

AAATGGGAGA GACCCTTTGA AGTCAAGGAC ACCGAGGAAG AGGACTTCCA CGTGGACCAG     720

GCGACCACCG TGAAGGTGCC TATGATGAAG CGTTTAGGCA TGTTTAACAT CCAGCACTGT     780

AAGAAGCTGT CCAGCTGGGT GCTGCTGATG AAATACCTGG GCAATGCCAC CGCCATCTTC     840

TTCCTGCCTG ATGAGGGGAA ACTACAGCAC CTGGAAAATG AACTCACCCA CGATATCATC     900

ACCAAGTTCC TGGAAAATGA AGACAGAAGG TCTGCCAGCT TACATTTACC CAAACTGTCC     960

ATTACTGGAA CCTATGATCT GAAGAGCGTC CTGGGTCAAC TGGGCATCAC TAAGGTCTTC    1020

AGCAATGGGG CTGACCTCTC CGGGGTCACA GAGGAGGCAC CCCTGAAGCT CTCCAAGGCC    1080

GTGCATAAGG CTGTGCTGAC CATCGACGAG AAAGGGACTG AAGCTGCTGG GGCCATGTTT    1140

TTAGAGGCCA TACCCATGTC TATCCCCCCC GAGGTCAAGT TCAACAAACC CTTTGTCTTC    1200

TTAATGATTG AACAAAATAC CAAGTCTCCC CTCTTCATGG GAAAAGTGGT GAATCCCACC    1260

CAAAAAACGC GTTCCAAATA TGGTCCCCCA TGCCCATCAT GCCCAGCACC TGAGTTCCTG    1320

GGGGGACCGT CAGTCTTCCT CTTCCCCCCA AAACCCAAGG ACACCCTCAT GATCTCCCGG    1380

ACCCCTGAGG TCACATGCGT GGTGGTGGAC GTGAGCCACG AAGACCCTGA GGTCAAGTTC    1440

AACTGGTACG TGGACGGCGT GGAGGTGCAT AATGCCAAGA CAAAGCCGCG GGAGGAGCAG    1500

TACAACAGCA CGTACCGTGT GGTCAGCGTC CTCACCGTCC TGCACCAGGA CTGGCTGAAT    1560

GGCAAGGAGT ACAAGTGCAA GGTCTCCAAC AAAGCCCTCC CAGCCCCCAT CGAGAAAACC    1620

ATCTCCAAAG CCAAAGGGCA GCCCCGAGAA CCACAGGTGT ACACCCTGCC CCCATCCCGG    1680
```

```
                                                       -continued
GATGAGCTGA CCAAGAACCA GGTCAGCCTG ACCTGCCTGG TCAAAGGCTT CTATCCCAGC          1740

GACATCGCCG TGGAGTGGGA GAGCAATGGG CAGCCGGAGA ACAACTACAA GACCACGCCT          1800

CCCGTGCTGG ACTCCGACGG CTCCTTCTTC CTCTACAGCA AGCTCACCGT GGACAAGAGC          1860

AGGTGGCAGC AGGGGAACGT CTTCTCATGC TCCGTGATGC ATGAGGCTCT GCACAACCAC          1920

TACACGCAGA AGAGCCTCTC CCTGTCTCCG GGTAAATGAG GATCT                         1965
```

AAT-Fc6 <Amino acid sequence >(Artificial: derived from human alpha-1
antitrypsin and human Fc fragment of IgG4)
648 a.a.

SEQ ID NO: 55

```
MPSSVSWGIL LLAGLCCLVP VSLAEDPQGD AAQKTDTSHH DQDHPTFNKI TPNLAEFAFS           60
LYRQLAHQSN STNIFFSPVS IATAFAMLSL GTKADTHDEI LEGLNFNLTE IPEAQIHEGF          120
QELLRTLNQP DSQLQLTTGN GLFLSEGLKL VDKFLEDVKK LYHSEAFTVN FGDTEEAKKQ          180
INDYVEKGTQ GKIVDLVKEL DRDTVFALVN YIFFKGKWER PFEVKDTEEE DFHVDQATTV          240
KVPMMKRLGM FNIQHCKKLS SWVLLMKYLG NATAIFFLPD EGKLQHLENE LTHDIITKFL          300
ENEDRRSASL HLPKLSITGT YDLKSVLGQL GITKVFSNGA DLSGVTEEAP LKLSKAVHKA          360
VLTIDEKGTE AAGAMFLEAI PMSIPPEVKF NKPFVFLMIE QNTKSPLFMG KVVNPTQKTR          420
SKYGPPCPSC PAPEFLGGPS VFLFPPKPKD TLMISRTPEV TCVVVDVSHE DPEVKFNWYV          480
DGVEVHNAKT KPREEQYNST YRVVSVLTVL HQDWLNGKEY KCKVSNKALP APIEKTISKA          540
KGQPREPQVY TLPPSRDELT KNQVSLTCLV KGFYPSDIAV EWESNGQPEN NYKTTPPVLD          600
SDGSFFLYSK LTVDKSRWQQ GNVFSCSVMH EALHNHYTQK SLSLSPGK                       648
```

AAT-Fc7 <Amino acid sequence >(Artificial: derived from human alpha-1
antitrypsin and human Fc fragment of IgG2 with hinge deletion)
634 a.a.

SEQ ID NO: 56

```
MPSSVSWGIL LLAGLCCLVP VSLAEDPQGD AAQKTDTSHH DQDHPTFNKI TPNLAEFAFS           60
LYRQLAHQSN STNIFFSPVS IATAFAMLSL GTKADTHDEI LEGLNFNLTE IPEAQIHEGF          120
QELLRTLNQP DSQLQLTTGN GLFLSEGLKL VDKFLEDVKK LYHSEAFTVN FGDTEEAKKQ          180
INDYVEKGTQ GKIVDLVKEL DRDTVFALVN YIFFKGKWER PFEVKDTEEE DFHVDQATTV          240
KVPMMKRLGM FNIQHCKKLS SWVLLMKYLG NATAIFFLPD EGKLQHLENE LTHDIITKFL          300
ENEDRRSASL HLPKLSITGT YDLKSVLGQL GITKVFSNGA DLSGVTEEAP LKLSKAVHKA          360
VLTIDEKGTE AAGAMFLEAI PMSIPPEVKF NKPFVFLMIE QNTKSPLFMG KVVNPTQKTR          420
PVAGPSVFLF PPKPKDTLMI SRTPEVTCVV VDVSHEDPEV KFNWYVDGVE VHNAKTKPRE          480
EQYNSTYRVV SVLTVLHQDW LNGKEYKCKV SNKALPAPIE KTISKAKGQP REPQVYTLPP          540
SRDELTKNQV SLTCLVKGFY PSDIAVEWES NGQPENNYKT TPPVLDSDGS FFLYSKLTVD          600
KSRWQQGNVF SCSVMHEALH NHYTQKSLSL SPGK                                     634
```

AAT-Fc7 <Amino acid sequence >(Artificial: derived from human alpha-1
antitrypsin and human Fc fragment of IgG2 with hinge deletion)
634 a.a.

SEQ ID NO: 57

```
MPSSVSWGIL LLAGLCCLVP VSLAEDPQGD AAQKTDTSHH DQDHPTFNKI TPNLAEFAFS           60
LYRQLAHQSN STNIFFSPVS IATAFAMLSL GTKADTHDEI LEGLNFNLTE IPEAQIHEGF          120
QELLRTLNQP DSQLQLTTGN GLFLSEGLKL VDKFLEDVKK LYHSEAFTVN FGDTEEAKKQ          180
```

-continued

```
INDYVEKGTQ GKIVDLVKEL DRDTVFALVN YIFFKGKWER PFEVKDTEEE DFHVDQATTV        240

KVPMMKRLGM FNIQHCKKLS SWVLLMKYLG NATAIFFLPD EGKLQHLENE LTHDIITKFL        300

ENEDRRSASL HLPKLSITGT YDLKSVLGQL GITKVFSNGA DLSGVTEEAP LKLSKAVHKA        360

VLTIDEKGTE AAGAMFLEAI PMSIPPEVKF NKPFVFLMIE QNTKSPLFMG KVVNPTQKTR        420

GGPSVFLFPP KPKDTLMISR TPEVTCVVVD VSHEDPEVKF NWYVDGVEVH NAKTKPREEQ

YNSTYRVVSV LTVLHQDWLN GKEYKCKVSN KALPAPIEKT ISKAKGQPRE PQVYTLPPSR

DELTKNQVSL TCLVKGFYPS DIAVEWESNG QPENNYKTTP PVLDSDGSFF LYSKLTVDKS

RWQQGNVFSC SVMHEALHNH YTQKSLSLSP GK

AAT-Fc9 <Amino acid sequence >(Artificial: derived from human alpha-1
antitrypsin and human Fc fragment of IgG4 with hinge deletion)
632 a.a.
                                                           SEQ ID NO: 58
MPSSVSWGIL LLAGLCCLVP VSLAEDPQGD AAQKTDTSHH DQDHPTFNKI TPNLAEFAFS         60

LYRQLAHQSN STNIFFSPVS IATAFAMLSL GTKADTHDEI LEGLNFNLTE IPEAQIHEGF        120

QELLRTLNQP DSQLQLTTGN GLFLSEGLKL VDKFLEDVKK LYHSEAFTVN FGDTEEAKKQ        180

INDYVEKGTQ GKIVDLVKEL DRDTVFALVN YIFFKGKWER PFEVKDTEEE DFHVDQATTV        240

KVPMMKRLGM FNIQHCKKLS SWVLLMKYLG NATAIFFLPD EGKLQHLENE LTHDIITKFL        300

ENEDRRSASL HLPKLSITGT YDLKSVLGQL GITKVFSNGA DLSGVTEEAP LKLSKAVHKA        360

VLTIDEKGTE AAGAMFLEAI PMSIPPEVKF NKPFVFLMIE QNTKSPLFMG KVVNPTQKTR        420

GGPSVFLFPP KPKDTLMISR TPEVTCVVVD VSHEDPEVKF NWYVDGVEVH NAKTKPREEQ        480

YNSTYRVVSV LTVLHQDWLN GKEYKCKVSN KALPAPIEKT ISKAKGQPRE PQVYTLPPSR        540

DELTKNQVSL TCLVKGFYPS DIAVEWESNG QPENNYKTTP PVLDSDGSFF LYSKLTVDKS        600

RWQQGNVFSC SVMHEALHNH YTQKSLSLSP GK                                     632
```

Commercially available formulations for comparisons and/or controls with recombinant or fusion molecules disclosed herein can include plasma-derived AAT in commercially available formulations of Aralast™ (Baxter), Zemaira™ (Aventis Behring), Prolastin™ or ProlastinC™ (Talecris), Aprotonin™ or Trasylol™ (Bayer Pharmaceutical Corporation), Ulinistatin™ (Ono Pharmaceuticals, Inc.), and inhalation and/or injectable AAT, Glassia™ (Kamada, Ltd., Israel), or any other commercially available AAT compositions or any combination thereof.

Other embodiments concern mutants of human AAT where the mutant is generated to have no significant serine protease inhibitor activity. Any method known in the art for generating mutants is contemplated. Some embodiments include using site-directed mutagenesis to generate a hAAT having no significant serine protease inhibitor activity (see Examples section and pEF-hAAT). In some embodiments, compositions can be a pharmaceutical composition having a mutated human alpha-1 antitrypsin (hAAT) wherein the AAT includes AAT with one or more point mutations at AAT's protease-binding site within AAT's reactive center loop (RCL). These one or more point mutations can significantly reduce or eliminate serine protease inhibition activity of the AAT compared to a control human AAT. Other methods include disrupting the serine protease inhibiting region of hAAT by other disruption methods such as heating hAAT, or generating a mutant such as an RCL mutant with a modified proline to cysteine residue at position 357 within the RCL to eliminate or dramatically reduce serine protease inhibitor activity, or chemically modifying AAT (e.g. human AAT). In certain embodiments, a fusion molecule can include linking manipulated Fc (e.g. IgG1, 2, 3 or 4) or FAB to an AAT mutant having one or more point mutations at one or more of amino acids within the RCL, (e.g. amino acids 355-363 of native AAT), wherein the AAT mutant has no significant serine protease inhibition activity and the RCL remains intact.

Pharmaceutical Compositions

Embodiments herein provide for administration of compositions to subjects in a biologically compatible form suitable for pharmaceutical administration in vivo. By "biologically compatible form suitable for administration in vivo" is meant a form of the active agent (e.g. pharmaceutical chemical, protein, gene, antibody etc. of the embodiments) to be administered in which any toxic effects are outweighed by the therapeutic effects of the active agent. Administration of a therapeutically active amount of the therapeutic compositions is defined as an amount effective, at dosages and for periods of time necessary to achieve the desired result. For example, a therapeutically active amount of a compound may vary according to factors such as the disease state, age, sex, and weight of the individual, and the ability of antibody to elicit a desired response in the individual. Dosage regimen may be adjusted to provide the optimum therapeutic response.

Pharmaceutical compositions containing AAT or peptide fragment thereof, or analog thereof, or mutant thereof, or a functional derivative thereof (e.g. pharmaceutical chemical, protein, peptide of some of the embodiments) may be administered to a subject, for example by subcutaneous, intravenous, intracardiac, intracoronary, intramuscular, by oral administration, by inhalation, transdermal application, intravaginal application, topical application, intranasal or rectal administration. Depending on the route of administration, the active compound may be coated in a material to protect the compound from the degradation by enzymes, acids and other natural conditions that may inactivate the compound. In a preferred embodiment, the compound may be orally administered. In another preferred embodiment, the compound may be administered intravenously. In one particular embodiment, the composition may be administered intranasally, such as inhalation.

Some embodiments disclosed herein concern using a stent or a catheter to deliver one or more chemotherapeutic agents (e.g. along with compositions disclosed herein) to a subject having or suspected being treated for cancer. Any stent or other delivery method known in the art that can deliver one or more agents directly to tumor site is contemplated. These delivery techniques can be used alone or in combination with other delivery methods.

A compound (e.g. a peptide, protein or mixture thereof) may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used.

Sterile injectable solutions can be prepared by incorporating active compound (e.g. a compound that reduces serine protease activity) in the required amount in an appropriate solvent with one or a combination of ingredients enumerated above, as required, followed by filtered sterilization.

Aqueous compositions can include an effective amount of a therapeutic compound, peptide, epitopic core region, stimulator, inhibitor, and the like, dissolved or dispersed in a pharmaceutically acceptable carrier or aqueous medium. Compounds and biological materials disclosed herein can be purified by means known in the art. Solutions of the active compounds as free-base or pharmacologically acceptable salts can be prepared in water suitably mixed with a surfactant, such as hydroxypropylcellulose.

Upon formulation, solutions will be administered in a manner compatible with the dosage formulation and in such amount as is therapeutically effective. The formulations are easily administered in a variety of dosage forms, such as the type of injectable solutions described above. It is contemplated that slow release capsules, timed-release microparticles, and the like can also be employed. These particular aqueous solutions are especially suitable for intravenous, intramuscular, subcutaneous and intraperitoneal administration.

The active therapeutic agents may be formulated within a mixture to comprise about 0.0001 to 1.0 milligrams, or about 0.001 to 0.1 milligrams, or about 0.1 to 1.0 or even about 1 to 10 gram per dose. Single dose or multiple doses can also be administered on an appropriate schedule for a predetermined condition such as daily, bi-weekly, weekly, bi-monthly etc. Pharmaceutical compositions are administered in an amount, and with a frequency, that is effective to modulate side effects. The precise dosage and duration of treatment may be determined empirically using known testing protocols or by testing the compositions in model systems known in the art and extrapolating therefrom. Dosages may also vary with the severity of the condition. In certain embodiments, the composition range can be between 1.0 and 75 mg/kg introduced daily or weekly to a subject. A therapeutically effective amount of $\alpha$1-antitrypsin, peptides, or drugs that have similar activities as $\alpha$1-antitrypsin or peptides can be also measured in molar concentrations and can range between about 1 nM to about 2 mM.

In another embodiment, nasal solutions or sprays, aerosols or inhalants may be used to deliver the compound of interest. Additional formulations that are suitable for other modes of administration may include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1%-2%.

Liposomes or microparticles can be used as a therapeutic delivery system and can be prepared in accordance with known laboratory techniques. In addition, dried lipids or lyophilized liposomes prepared as previously described may be reconstituted in a solution of active agent (e.g. nucleic acid, peptide, protein or chemical agent), and the solution diluted to an appropriate concentration with a suitable solvent known to those skilled in the art. The amount of active agent encapsulated can be determined in accordance with standard methods.

In some embodiments, pharmaceutical construct compositions concerns a construct derived from an AAT molecule having no significant serine protease inhibitor activity but having other $\alpha$1-antitrypsin activity or analog thereof may be used in a single therapeutic dose, acute manner or a chronic manner to treat a subject. For example, the fusion polypeptides contemplated herein can be a fusion polypeptide having no significant protease inhibition activity.

In certain embodiments, compositions herein can be administered orally, systemically, via an implant, time released or slow-release compositions (e.g. gel, microparticles etc.), intravenously, topically, intrathecally, subcutaneously, by inhalation, nasally, or by other means known in the art or a combination thereof.

Expression Proteins and Constructs

Once the target gene or portion of a gene has been determined, the gene can be inserted into an appropriate expression system. The gene can be expressed in any number of different recombinant DNA expression systems to generate large amounts of the polypeptide product, which can then be purified and used in compositions and methods disclosed herein.

Examples of expression systems known to the skilled practitioner in the art include bacteria such as *E. coli*, yeast such as *Pichia pastoris*, baculovirus, and mammalian expression systems such as in Cos or CHO cells. A complete gene can be expressed or, alternatively, fragments of the gene encoding portions of polypeptide can be produced.

The AAT gene or gene fragment encoding a polypeptide may be inserted into an expression vector by standard subcloning techniques. An *E. coli* expression vector may be used which produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.).

Amino acid sequence variants of the polypeptide may also be prepared. These may, for instance, be minor sequence variants of the polypeptide which arise due to natural variation within the population or they may be homologues found in other species. They also may be sequences which do not occur naturally but which are sufficiently similar that they function similarly and/or elicit an immune response that cross-reacts with natural forms of the polypeptide. Sequence variants may be prepared by standard methods of site-directed mutagenesis such as those described herein for removing the transmembrane sequence.

Amino acid sequence variants of the polypeptide may be substitutional, insertional or deletion variants. Deletion variants lack one or more residues of the native protein which are not essential for function or immunogenic activity, and are exemplified by the variants lacking a transmembrane sequence.

The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

As used herein, the terms "engineered" and "recombinant" cells are intended to refer to a cell into which an exogenous DNA segment or gene, such as an AAT full-length cDNA or gene has been introduced through the hand of man. Therefore, engineered cells are distinguishable from naturally occurring cells which do not contain a recombinantly introduced exogenous DNA segment or gene. Recombinant cells include those having an introduced cDNA or genomic gene, and also include genes positioned adjacent to a heterologous promoter not naturally associated with the particular introduced gene.

To express a recombinant encoded protein or peptide, whether full-length AAT mutant or wild-type or carboxyterminal peptide thereof, in accordance with embodiments herein, one could prepare an expression vector that includes an isolated nucleic acid under the control of, or operatively linked to, one or more promoters as known in the art. Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic. ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells.

In addition, phage vectors containing replicon and control sequences that are compatible with the host microorganism may be used as transforming vectors in connection with these hosts. For example, the phage lambda GEM™-11 may be utilized in making a recombinant phage vector which may be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in *Saccharomyces*, the plasmid YRp7, for example, is commonly used. This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan. Suitable promoting sequences in yeast vectors are known in the art. In constructing suitable expression plasmids, the termination sequences associated with these genes are also ligated into the expression vector 3' of the sequence desired to be expressed to provide polyadenylation of the mRNA and termination. Other suitable promoters, which have the additional advantage of transcription controlled by growth conditions, are also contemplated of use herein.

In addition to microorganisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV or other plants) or transformed with recombinant plasmid expression vectors (e.g., Ti plasmid) containing one or more coding sequences. Insect systems are also contemplated.

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cells lines or host systems may be chosen to ensure the correct modification and processing of the foreign protein expressed. Expression vectors for use in mammalian cells ordinarily include an origin of replication (as necessary), a promoter located in front of the gene to be expressed along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient. The promoters may be derived from the genome of mammalian cells. Further, it is also possible, and may be desirable, to utilize promoter or control sequences normally associated with the desired gene sequence, provided such control sequences are compatible with the host cell systems.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons may be of a variety of origins, both natural and synthetic. The efficiency of expression may be enhanced by the inclusion of appropriate transcription enhancer elements or transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells may be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn may be cloned and expanded into cell lines.

A number of selection systems may be used, including but not limited to, the herpes simplex virus thymidine kinase, hypoxanthine-guanine phosphoribosyltransferase, and adenine phosphoribosyltransferase genes, in tk-, hgprt- or aprt-cells, respectively. Also, antimetabolite resistance may be used as the basis of selection for dhfr, that confers resistance to methotrexate: gpt, that confers resistance to mycophenolic acid; neo, that confers resistance to the aminoglycoside G-418 and hygro, that confers resistance to hygromycin or any other method known the art.

It is contemplated that the isolated nucleic acids of the invention may be "overexpressed", i.e., expressed in increased levels relative to its natural expression in human prostate, bladder or breast cells, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural human prostate, bladder or breast cells is indicative of overexpression, as is a relative abundance of the specific protein in relation to the other proteins produced by the host cell and, e.g., visible on a gel.

It is contemplated herein that constructs generated utilizing an immune molecule (e.g. Fc portion) can be isolated using various affinity columns. In addition, Fc fragments can also be further manipulated such as removing the hinge region. These Fc fragments can include any of IgG1, IgG2, IgG3, IgG4 or IgD. The hinge region can be eliminated or truncated or mutated prior to linking the immune fragment to an AAT target molecule.

Isolated Proteins

One embodiment pertains to isolated proteins, and biologically active peptides thereof. In one embodiment, the native polypeptide can be isolated from cells or tissue sources by an appropriate purification scheme using standard protein purification techniques. In certain embodiments, the native polypeptide may be heated or otherwise treated to reduce or eliminate serine protease inhibitor activity. In certain particular embodiments, serine protease inhibitor activity is reduced where no significant activity remains. In another embodiment, polypeptides contemplated herein are produced by recombinant DNA techniques. Alternative to recombinant expression, a polypeptide can be synthesized chemically using standard peptide synthesis techniques. Any of the peptide or protein molecules contemplated of use in compositions disclosed herein can be compositions having no significant serine protease inhibitor activity. For example, AAT compositions may be mutated or truncated in order to reduce or eliminate serine protease inhibitor activity or an AAT polypeptide may be isolated wherein the polypeptide has reduced or no significant serine protease inhibitor activity.

An "isolated" or "purified" protein or biologically active portion thereof is substantially free of cellular material or other contaminating proteins from the cell or tissue source from which the protein is derived, or substantially free of chemical precursors or other chemicals when chemically synthesized. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium. When the protein is produced by chemical synthesis, it is preferably substantially free of chemical precursors or other chemicals. For example, such preparations of the protein have less than about 30%, 20%, 10%, 5% (by dry weight) of chemical precursors or compounds other than the polypeptide of interest.

In certain embodiments, nucleotides that encode polypeptides can be inserted to any construct known in the art for generating a peptide or protein. These peptides can include a polypeptide having a consecutive amino acid sequence corresponding to a portion or all of the last 80 amino acids of carboxyterminus of AAT or AAT allele. Other useful proteins are substantially identical to any portion of the carboxyterminus, and retain the functional activity of the peptide of the corresponding naturally-occurring protein other than serine protease inhibitor activity yet differ in amino acid sequence due to natural allelic variation or mutagenesis.

In certain embodiments, purification of Fc-AAT constructs disclosed herein can include using a Protein A column or protein A matrix or the like (Pierce or other IgG purification kit). In certain embodiments, purification of constructs disclosed herein can be by using minimal steps to preserve anti-inflammatory or immune modulatory activity of a target AAT protein or peptide. In accordance with these embodiments, purification of constructs contemplated herein may be by a single step (e.g. protein A column purification of Fc-AAT molecules) (See for example Kin-Ming et al. Protein Engineering vol. 11 no. 6 pp. 495-500, 1998; expression/FcFc-X/fusion protein; and diabody technologies).

It is contemplated herein that a nucleic acid encoding any protein or peptide capable of reversibly binding to itself (e.g. through disulfide or other binding) can be used to generate AAT constructs disclosed herein. These constructs can be used as doublets of AAT for increased purification with reduced loss of function and can also be used as a dimeric molecule for use in therapeutic applications or for research purposes. In accordance with these embodiments, the portion linked to AAT or the carboxyterminal fragment can be inert or essentially non-immunogenic unless increased immugenicity is desired. Further, Fc is manipulated in constructs disclosed herein to reduce or eliminate complement interaction or activation (e.g. hinge is deleted). Positioning Fc at the carboxyterminal region of AAT has been demonstrated to not interfere with certain AAT activities such as anti-inflammatory and elastase inhibition.

Other Uses

Some compositions disclosed herein may be used as therapeutic agents in the treatment of a physiological condition caused in whole or part, by excessive serine protease activity. In addition, a physiological condition can be inhibited in whole or part. Peptides contemplated herein may be administered in a composition as free peptides or pharmaceutically acceptable salts thereof. Peptides may be administered to a subject as a pharmaceutical composition, which, in most cases, will include the fusion molecule and a pharmaceutically acceptable excipient, or pharmaceutically acceptable carrier or a pharmaceutically acceptable salt formulation thereof.

Biologically active portions of AAT or a peptide derivative thereof can include amino acid sequences sufficiently identical to or derived from the amino acid sequence of the protein (e.g., the amino acid sequence captured by any of SEQ ID NOs:2 to 32, 34, 49 or 51 which exhibit at least one activity of the corresponding full-length protein). A biologically active portion of a protein of the invention can be a polypeptide, which is, for example, 5, 10, 20, 30, 40 or more amino acids in length. Moreover, other biologically active portions having no significant serine protease inhibitor activity, in which other regions of the protein are deleted, can be prepared by recombinant techniques and evaluated for one or more of the functional activities of the native form of a polypeptide disclosed herein.

In certain embodiments, polypeptides may have the amino acid sequence of SEQ ID NOs:2 to 32, 34, 49 or 51. Other useful proteins are substantially identical (e.g., at least about, 85%, 90%, 95%, or 99%) to any of SEQ ID NOs1: to 34, 49 and 51, and AAT linked to Fc represented by SEQ ID No. 49, 56, 57, 58 or other construct with or without an Fc hinge region manipulation.

Variants of AAT molecules having no significant serine protease activity can be generated by mutagenesis, e.g., discrete point mutation or truncation. For example, a point mutation may be generated in AAT or peptide derivative thereof that still leaves the reactive center loop intact (RCL) while interfering with or preventing serine protease binding capabilities with the AAT or peptide but retaining its ability to modulate radiation adverse effects. An agonist can retain substantially the same, or a subset, of the biological activities of the naturally occurring form of the protein except no significant serine protease activity remains. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Fusion Polypeptides

In other embodiments, agents such as AAT and/or analog thereof, or peptide derivative or fragment thereof may be part of a fusion polypeptide. In one example, a fusion polypeptide may include AAT (e.g. naturally occurring mammalian α1-antitrypsin, such as human) or an analog thereof or fragment thereof and a different amino acid sequence that may be an immunofragment such as an IgG fragment (e.g. Fc hinge deletion or hinge truncation or mutant thereof). In addition, a fusion polypeptide disclosed herein can include a pharmaceutically acceptable carrier, excipient or diluent. Any known methods for generating a fusion protein or fusion peptide are contemplated herein.

In yet another embodiment, AAT polypeptide or peptide fusion protein can be a GST fusion protein in which is fused to the C-terminus of GST sequences. Fusion expression vectors and purification and detection means are known in the art. Expression vectors can routinely be designed for expression of a fusion polypeptide of the invention in prokaryotic (e.g., *E. coli*) or eukaryotic cells (e.g., insect cells (using baculovirus expression vectors), yeast cells or mammalian cells) by means known in the art. In yet another embodiment, a nucleic acid of the invention is expressed in mammalian cells using a mammalian expression vector as described in the art.

When examining effects of plasma-derived AAT formulations on a system compared to fusion molecules disclosed herein, protein concentration is taken into consideration because Fc-AAT disclosed herein occur as a doublet of 2 AAT molecules unless they are cleaved or reduced which generates two Fc-AAT single molecules. Fc-AAT fusion molecules of use in compositions disclosed herein can include a pharmaceutically acceptable composition of one or more of SEQ ID NO: 32, 49, 51, 53, or 55-58 to treat a subject having an inflammatory condition or other condition responsive to plasma-derived AAT treatment as provided herein or known in the art. In certain embodiments, Fc linked to AAT, a mutant AAT form or AAT peptide fragment may increase the half-life of AAT in vivo or facilitate cellular uptake and transport of the construct in vivo. Thus, novel molecules have been made where multiple improvements have been observed regarding generating a recombinant form of AAT compared to plasma-derived AAT and other recombinants, as well as improvements in vivo compared to Fc-AAT (IgG1, Fc-AAT2).

Combination Therapies

Any of the embodiments detailed herein may further include one or more other therapeutically effective agent in combination with compositions disclosed herein. In certain embodiments, these alternative agents can include cancer-related medications in the treatment of cancer. For example, these therapies can include, but are not limited to, aspirin and other antiplatelet therapy including for example, clopidogrel, prasugrel, ticagrelor, abciximab, eptifibatide, tirofiban; heparin and derivatives; direct thrombin inhibitors or Xa inhibitors; warfarin; angiotensin converting enzyme inhibitors or angiotensin receptor blockers; beta- and alpha-adrenergic receptor blockers; calcium channel blockers; HMGCoA reductase inhibitors (e.g. statins); niacin and derivatives; fenofibrate; fish oil; aldosterone blockers; hydralazine and nitroderivates; phosphodiesterase inhibitors; direct guanylil cyclase activators, anti-microbial drugs, anti-inflammatory agent, immunomodulatory agent, or immunosuppressive agent or combination thereof.

Examples of anti-bacterial agents include, but are not limited to, penicillins, quinolones, aminoglycosides, vancomycin, monobactams, cephalosporins, carbacephems, cephamycins, carbapenems, and monobactams and their various salts, acids, bases, and other derivatives.

Anti-fungal agents contemplated of use herein can include, but are not limited to, caspofungin, terbinafine hydrochloride, nystatin, amphotericin B, griseofulvin, ketoconazole, miconazole nitrate, flucytosine, fluconazole, itraconazole, clotrimazole, benzoic acid, salicylic acid, and selenium sulfide.

Anti-viral agents contemplated of use herein can include, but are not limited to, valgancyclovir, amantadine hydrochloride, rimantadin, acyclovir, famciclovir, foscamet, ganciclovir sodium, idoxuridine, ribavirin, sorivudine, trifluridine, valacyclovir, vidarabin, didanosine, stavudine, zalcitabine, zidovudine, interferon alpha, and edoxudine.

Anti-parasitic agents contemplated of use herein can include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole, (sulfamethoxazole/trimethoprim), and pentamidine isethionate.

Immunomodulatory agents can include for example, agents which act on the immune system, directly or indirectly, by stimulating or suppressing a cellular activity of a cell in the immune system, (e.g., T-cells, B-cells, macrophages, or antigen presenting cells (APC)), or by acting upon components outside the immune system which, in turn, stimulate, suppress, or modulate the immune system (e.g., hormones, receptor agonists or antagonists, and neurotransmitters); other immunomodulatory agents can include immunosuppressants or immunostimulants. Anti-inflammatory agents can include, for example, agents which treat inflammatory responses, tissue reaction to injury, agents that treat the immune, vascular, or lymphatic systems or any combination thereof.

Anti-inflammatory or immunomodulatory drugs or agents contemplated of use herein can include, but are not limited to, interferon derivatives, e.g., betaseron, 3-interferon; prostane derivatives, iloprost, cicaprost; glucocorticoids such as cortisol, prednisolone, methylprednisolone, dexamethasone; immunosuppressive agents such as cyclosporine A, FK-506, methoxsalene, thalidomide, sulfasalazine, azathioprine, methotrexate; lipoxygenase inhibitors, e.g., zileutone, MK-886, WY-50295, SC-45662, SC-41661A, BI-L-357; leukotriene antagonists; peptide derivatives for example ACTH and analogs; soluble TNF (tumor necrosis factor)-receptors; TNF-antibodies; soluble receptors of interleukins, other cytokines, T-cell-proteins; antibodies against receptors of interleukins, other cytokines, and T-cell-proteins.

Other agents of use in combination with compositions herein can be molecules having serine protease inhibitor activity. For example other serine protease inhibitors contemplated of use herein can include, but are not limited to, leukocyte elastase, thrombin, cathepsin G, chymotrypsin, plasminogen activators, and plasmin.

In addition, other combination compositions of methods disclosed herein can include certain antibody-based therapies. Non-limiting examples include, polyclonal anti-lymphocyte antibodies, monoclonal antibodies directed at the T-cell antigen receptor complex (OKT3, TIOB9), monoclonal antibodies directed at additional cell surface antigens, including interleukin-2 receptor alpha. In certain embodiments, antibody-based therapies may be used as induction therapy in combination with the compositions and methods disclosed herein.

Subjects contemplated herein can include human subjects, male or female, adult or infant, or fetus, or other subjects such as non-human subjects, including but not limited to, primates, dogs, cats, horses, cows, pigs, guinea pigs, birds and rodents.

AAT

Human AAT is a single polypeptide chain with no internal disulfide bonds and only a single cysteine residue normally intermolecularly disulfide-linked to either cysteine or glutathione. One reactive site of AAT contains a methionine residue, which is labile to oxidation upon exposure to tobacco smoke or other oxidizing pollutants. Such oxidation reduces the elastase-inhibiting activity of AAT; therefore substitution of another amino acid at that position, e.g., alanine, valine, glycine, phenylalanine, arginine or lysine, produces a form of AAT which is more stable. Native AAT can be represented by the formula of SEQ ID NO: 1 or 33 or other known naturally-occurring AAT molecule.

Any means known for producing and purifying fusion molecules disclosed herein is contemplated (e.g. in mammalian cells, by bacteria, by fungi or other organisms or produced in plants).

Kits

In still further embodiments, kits for use with compositions, constructs (e.g. recombinant and/or fusion molecules) and methods described above are contemplated. Kits may include AAT fusion or recombinant constructs (e.g. Fc-AAT;

Fc-mutant AAT, IgG2 mutant linked to AAT or carboxyterminal derivative of AAT or Fc, hinge deleted constructs, SEQ ID NO. 32, 49-58 etc.), constructs of one or more peptides derived from AAT, a mutant AAT construct composition, a mutant AAT molecule associated with a gene therapy delivery system or other combinations. Small molecules, proteins or peptides may be employed for use in any of the disclosed methods. In addition, other agents such as anti-bacterial agents, immunosuppressive agents, anti-inflammatory agents may be provided in the kit. The kits can include, suitable container means, a protein or a peptide or analog agent, and optionally one or more additional agents.

The kits may further include a suitably aliquoted construct composition of the encoded protein or polypeptide antigen, whether labeled or unlabeled, as may be used to prepare a standard curve for a detection assay or for therapeutic applications described.

Containers of the kits will generally include at least one vial, test tube, flask, bottle, syringe or other container means or other delivery device (e.g. a stent or catheter). A kit will also generally contain a second, third or other additional container into which other combination agents may be placed. Such containers may include injection or blow-molded plastic containers into which the desired vials are retained.

In certain embodiments, a kit can include a composition including, but not limited to, constructs of AAT, AAT fragment, or an AAT analog or polypeptide, having no significant serine protease inhibitor activity. In accordance with these embodiments, a kit can contain AAT or an analog thereof having no significant serine protease inhibitor activity.

EXAMPLES

The following examples are included to illustrate various embodiments. It should be appreciated by those of skill in the art that the techniques disclosed in the examples which follow represent techniques discovered to function well in the practice of the claimed methods, compositions and apparatus. However, those of skill in the art should, in light of the present disclosure, appreciate that changes may be made in the some embodiments which are disclosed and still obtain a like or similar result without departing from the spirit and scope of the invention.

Example 1

Generation of Expression Plasmid for Production of Recombinant Human AAT

Figure 2:
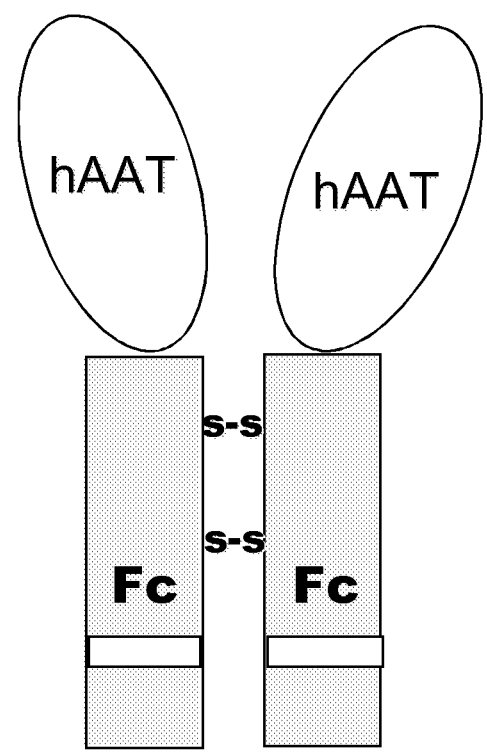
FIG. 2 represents a schematic of human AAT constructs with associated immune molecules contemplated of use for some embodiments disclosed herein.
Figure 3:
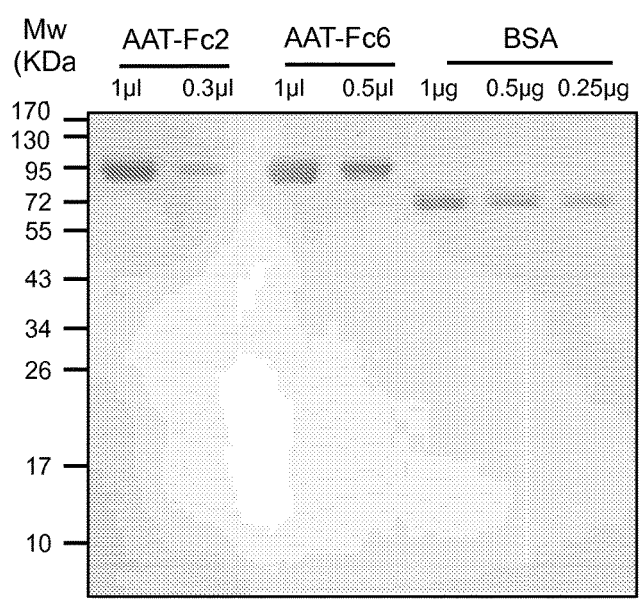
FIG. 3 represents a SDS-PAGE gel illustrating migration of some fusion molecules generated by certain embodiments disclosed herein.

In one exemplary method, Fc-AAT constructs can be generated. Recombinant AAT can be generated for fusion molecules as indicated in FIG. 1. Insertion of human AAT (or AAT peptides such as carboxyterminal peptides) sequences into an expression vector, pCAGGS. Human full-length AAT cDNA of 1260 base pairs was isolated from a human liver library and inserted into pCAGGS as illustrated in FIG. 1. Chinese Hamster Ovary (CHO) cells were transfected with the plasmid for expression. Using limiting dilution, AAT-positive clones were selected and grown in serum free media The supernatants were collected and pooled. Using an antibody to human AAT, a band of about 55 kDa was observed on Western blots (data not shown) verifying AAT. A fusion protein with the human IgG1, IgG2, IgG3 or IgG4 (with or without varying hinge region deletions, mutations and up to a total hinge region deletion) Fc receptor was used to generate recombinant AAT or fusion molecules thereof. These constructs were purified. In certain exemplary methods, these constructs were purified using Protein A (as a column or matrix etc.) to bind Fc and rapidly isolate a target fusion molecule from a solution. See FIG. 3 for a representative SDS-PAGE gel separation of fusion molecules produced herein (e.g. Fc-AAT2/AAT-Fc2 and Fc-AAT-6/AAT-Fc6)

Example 2

In another exemplary method, fusion constructs disclosed herein can be purified and used for methods or therapeutic treatment for any condition known to be treated by commercially available AAT compositions or other inflammatory condition.

Human Fc IgG plasmids can be purchased from Qiagen (e.g. IgG1, IgG2, IgG3 and IgG4 etc.). The human cDNA was excised and inserted into the human Fc vector via PCR cloning. The in-frame sequence was performed for validation. The plasmid was transfected into CHO cells and after limiting dilutions to obtain single clones, several stable clones were isolated. The stable clones were expanded and further selected using serum-free medium. Large scale cell culture was performed and the supernatants collected and pooled.

Supernatant containing Fc-AAT fusion molecules can be purified using Protein A as a matrix, in a gel or in a column. In certain methods, human Fc-AAT generated herein was eluted from the protein A using glycine (about pH 2.4) and then rapidly neutralized to physiological pH, about pH 7.4. These methods produced a single band on an SDS-PAGE gel under reducing conditions. Purified Fc-AAT fusion constructs could then be readily compared to commercially available formulations such as Aralast™, Glassia™, Prolastin C™ for AAT-related activities such as elastase inhibition assay, anti-inflammatory assays (e.g. effects on cytokine levels etc.).

Purification of human AAT Fc: A Western blot demonstrated bands (about 170 kDa) that represent intact dimer of two Fc-AAT full length molecules without manipulation to the Fc from IgG1. Other lanes on the Western blot represented when all disulfide bonds were broken to form 2 singular molecules of FC-AAT. Both non-reducing gels as well as reducing gels demonstrated level of purity of the AAT constructs. Fc-AAT can be purified in a single step from a mammalian cell culture supernatant using protein A chromatography thus dramatically reducing side-effects of purification deleterious to AAT activities. The following clones were generated Clone 2: Fc-AAT using IgG1 and a linker to the carboxyterminus of AAT: Clone 3: Fc-AAT using IgG1 where the hinge region of Fc is removed and a linker that is again linked to the carboxyterminus of AAT. Other clones have been generated that include Fc from IgG2, IgG3 and IgG4 with and without hinge region deletions. It is noted that Fc-AAT2 and Fc-AAT3 retain elastase inhibition activity but behave differently under certain conditions when compared both in vivo and in vitro implicating another active region of AAT other than the serine protease inhibition activity region is involved and proposed to be anti-inflammatory and anti-immune active regions AAT.

Example 3

It was hypothesized that effects of Fc-AAT (or mouse AAT Fc) on cytokine-induced TNFα from mouse RAW macrophages would be more potent to reduce TNFα than that of native AAT (e.g. commercially available formulations) due in part to rapid purification and conserved AAT activity of the clones. It is also hypothesized that clone 3, having a complete hinge deletion may be more potent in vitro in certain activities tested but also an improved formulation for in vivo use due to reduced secondary activity issues (e.g. reduced complement activation etc.): In one exemplary method, ATT-Fc2/Fc-AAT2 (clone 2 intact IgG1 hinge) and AAT-Fc3/Fc-AAT (clone 3, deleted IgG1 hinge) were examined for effects on spontaneous production of immune stimulatory activities, mouse TNFα production, in order to examine an unwanted immune activities.

Figure 4A:
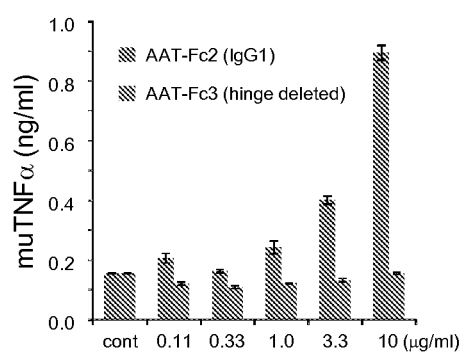
FIGS. 4A and 4B illustrate, by histogram plot, cytokine production (e.g. TNFα, tumor necrosis factor-alpha) in an in vitro cell model exposed to certain AAT fusion molecules disclosed herein (4A) in comparison to a commercially available AAT formulation (4B).
Figure 4:
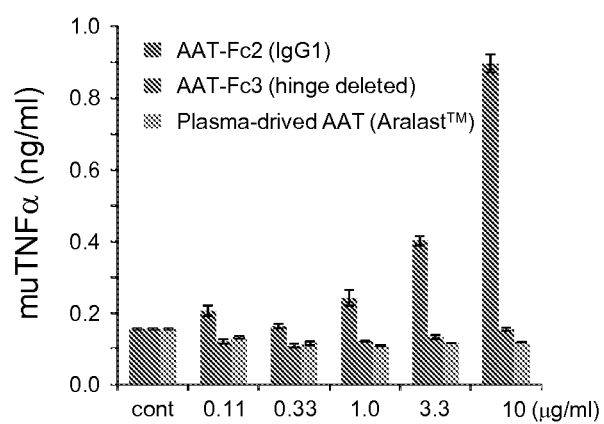

Cytokine Assays for AAT fusion molecules: assays on cell cultures for cytokine production in vitro. RAW macrophages were used for the following experiments. Raw 264.7 cells in 96 well plate ($3 \times 10^5$ cells per well) were used. Increased concentrations of AAT-Fc2 and AAT-Fc3 were applied to stimulate the mouse RAW cells as indicated in the figures. Mean±SEM of mouse TNFα production by the AAT-Fcs were measured by a standard ELISA kit according to manufactures' instruction (R&D Systems, Minneapolis Minn.). Here, the difference in spontaneous induction of mouse TNFα by two different AAT-Fc molecules was examined. These results support that AAT-Fc3 (hinge deleted) is more effective in reducing TNFα production, a pro-inflammatory cytokine marker, even in this in vitro model. FIG. 4A represents a comparison of two fusion molecules, Fc-AAT2 and FcAAT3 and effects of TNFα production in an in vitro system. FIG. 4B represents a comparison of two fusion molecules, Fc-AAT2 and Fc-AAT3, with a commercially available plasma-derived AAT formulation (Aralast™). Fc-AAT3 demonstrates superior results comparable to plasma-derived AAT (Aralast™). Of note, tumor necrosis factor (TNF), cachexin, or cachectin, and formerly known as tumor necrosis factor-alpha or TNF-α is a cytokine involved in systemic inflammation and is a member of a group of cytokines that stimulate the acute phase reaction. It is produced chiefly by activated macrophages (M1), although it can be produced by many other cell types as CD4+ lymphocytes, NK cells and neurons. This in vitro study supports that Fc-AAT where the hinge region is deleted or modified has certain superior qualities to Fc-AAT with an intact Fc hinge region and is as active as plasma-derived formulations to inhibit TNF production.

These experiments were performed three times in order ensure that the observed results of AAT-Fc2 (IgG1, clone 2) and AAT-Fc3 (hinge deleted, IgG2, clone 3) were comparable and an accurate reflection of their potency compared to a commercially available formulations (see for example, FIGS. 4A and 4B). Here, it was observed that there was a significant difference in spontaneous production of mouse TNFα by AAT-Fc2 (IgG1) and AAT-Fc3 (hinge deleted) (FIG. 4A) where AAT-Fc3 induction of TNFα is dramatically reduced compared to AAT-Fc2. Further, there was a dramatic difference when comparing commercially available formulations (e.g. Aralast) with AAT-Fc2 (clone 2) and AAT-Fc3 (clone 3).

Similar data were observed using human IL-33 as a stimulant. Recombinant mouse IL-33 was also tested and demonstrated consistent suppression of TNFα by 100 and 50 ng/mL levels of Fc-AAT (IgG1 Fc intact with AAT full length (data not shown)).

Example 4

IL-1 Receptor Antagonist Induction and IL-8 Induction

Figure 5A:
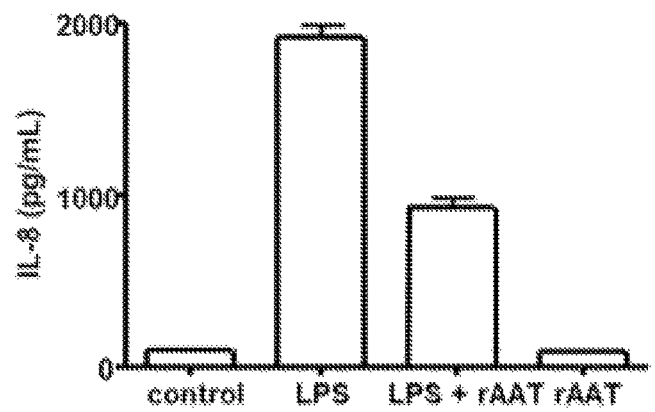
FIGS. 5A and 5B represent reduction in expression of various pro-inflammatory cytokines in the presence or absence of LPS (5A) with or without an AAT fusion molecule (rAAT or recombinant AAT) and expression of IL-1Ra using decreasing amounts of an AAT fusion molecule (rec AAT-Fc; recombinant Fc-AAT) (5B).

In this exemplary method, production of IL-8 is assessed. IL-8 is an inflammatory molecule and its production is an indication of an induced inflammatory response. In this example, human blood neutrophils ($3 \times 10^6$ cells/ml) were incubated for 6 hours alone or in the presence of LPS (10 ng/ml), recombinant AAT (clone 2) (10 µg/ml) or a combination of the two. Production of IL-8 was measured in the cell culture supernatants (N=3). It was demonstrated that recombinant AAT dramatically reduced IL-8 expression in the presence of the stimulant LPS. It is proposed that clone 3 (hinge deletion of IgG1) will have a similar activity as reflected in this experiment (see FIG. 5A) because the AAT portion of this clone is intact while the Fc is manipulated. This data is supported by previous data using plasma-derived AAT (data not shown). Thus, these molecules are capable of inhibiting inflammation.

Figure 5B:
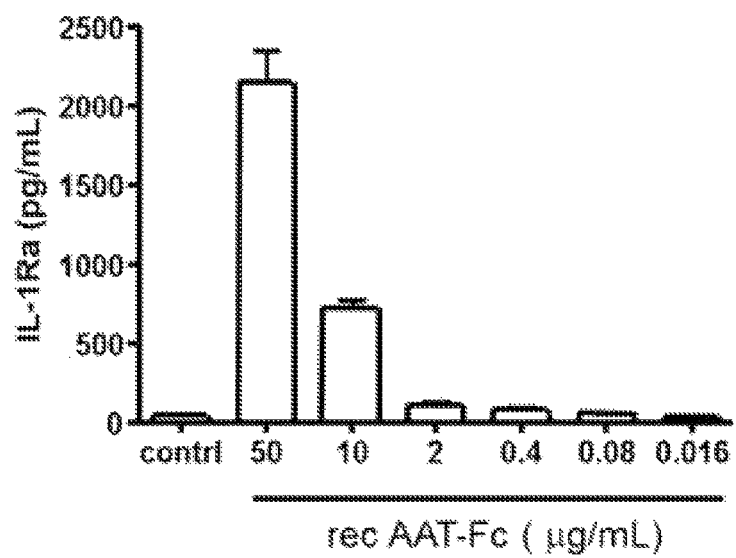

In another exemplary method, IL-1 receptor antagonist (IL-1Ra) was analyzed in order to assess recombinant molecule formulations effects on another inflammation marker. In this example, productions of IL-1 receptor antagonists from human neutrophils cells were measured in various concentrations of recombinant AAT (Fc-AAT2, clone 2: See Fig. Y2, con equals a negative control having no induction of the molecule). These experiments revealed that recombinant AAT at very low levels was able to dramatically inhibit IL-1Ra production. Because the region of AAT found in this clone is identical to Fc-AAT3 (without hinge), this data supports similar activity in Fc-AAT3 would be obtained as compared to Fc-AAT2 demonstrated here (see FIG. 5B).

Example 5

Other cytokine expression has been examined where effects of FcAAT (clone 2) were analyzed (e.g. IL-1beta, IFNgamma, IL-17 etc.), parts of these results are illustrated in Table 1 below. It was demonstrated that recombinant AAT having an Fc fusion was capable of blocking deleterious cytokine production.

TABLE 1

| Suzhao Trial 1 | Percent Inhibition | | |
|---|---|---|---|
| | Donor 1 | Donor 2 | Donor 3 |
| TNF-a | | | |
| 10 ug/mL FcAAT + Anti CD3/CD28 | 54% | 54% | 47% |
| 1 ug/mL FcAAT + Anti CD3/CD28 | 17% | 50% | 29% |
| 0.1 ug/mL FcAAT + Anti CD3/CD28 | 28% | 56% | 100% |
| 0.01 ug/mL FcAAT + Anti CD3/CD28 | −15% | 63% | 100% |
| 0.001 ug/mL FcAAT + Anti CD3/CD29 | | 0% | |
| IL-6 | | | |
| 10 ug/mL FcAAT + Anti CD3/CD28 | −35% | −250% | 100% |
| 1 ug/mL FcAAT + Anti CD3/CD28 | 52% | −344% | 47% |

TABLE 1-continued

| | | | | |
|---|---|---|---|---|
| 0.1 ug/mL FcAAT + Anti CD3/CD28 | | 30% | 77% | 100% |
| 0.01 ug/mL FcAAT + Anti CD3/CD28 | | −35% | 69% | 100% |
| 0.001 ug/mL FcAAT + Anti CD3/CD29 | | | 15% | |
| IL-1beta | | | | |
| 10 ug/mL FcAAT + Anti CD3/CD28 | | −55% | −305% | 100% |
| 1 ug/mL FcAAT + Anti CD3/CD28 | | 30% | −532% | 72% |
| 0.1 ug/mL FcAAT + Anti CD3/CD28 | | 7% | 8% | 100% |
| 0.01 ug/mL FcAAT + Anti CD3/CD28 | | −45% | 17% | 97% |
| 0.001 ug/mL FcAAT + Anti CD3/CD29 | | | −100% | |
| IFN-g | | | | |
| 10 ug/mL FcAAT + Anti CD3/CD28 | | −262% | 30% | |
| 1 ug/mL FcAAT + Anti CD3/CD28 | | −9% | 20% | |
| 0.1 ug/mL FcAAT + Anti CD3/CD28 | | 17% | 100% | |
| 0.01 ug/mL FcAAT + Anti CD3/CD28 | | 65% | 100% | |
| 0.001 ug/mL FcAAT + Anti CD3/CD29 | | | 14% | |
| IL-17 | | | | |
| 26% | 10 ug/mL FcAAT + Anti CD3/CD28 | | | 100% |
| 19% | 1 ug/mL FcAAT + Anti CD3/CD28 | | | 100% |
| 51% | 0.1 ug/mL FcAAT + Anti CD3/CD28 | | | 100% |
| | 0.01 ug/mL FcAAT + Anti CD3/CD28 | | | 92% |
| | 0.001 ug/mL FcAAT + Anti CD3/CD29 | | | |

| | | | | | AAT-Fc 2 | AAT-Fc 2 | AAT-Fc 3 | AAT-Fc 3 | | | | |
|---|---|---|---|---|---|---|---|---|---|---|---|---|
| IL-1b pg/ml | Donor 1 | Alone | Control | | 0 | 0 | 0 | 0 | Alone | Control | 0 | 0 |
| | | | 30 ug/ml | | 12 | 26 | 6 | 7 | | E. LPS 100 ng/ml | 5 | 8 |
| | | | 15 ug/ml | | 5 | 13 | 2 | 2 | | E. LPS 10 ng/ml | 4 | 3 |
| | | Plus Bartonella | Control | | 0 | 2 | | 2 | Plus Bartonella | Control | 0 | 0 |
| | | | 30 ug/ml | | 11 | 42 | 5 | 6 | | E. LPS 100 ng/ml | 3 | 3 |
| | | | 15 ug/ml | | 7 | 13 | 2 | 3 | | E. LPS 10 ng/ml | 2 | 2 |
| | Donor 2 | Alone | Control | | 3 | 1 | 0 | 2 | Alone | Control | 0 | 0 |
| | | | 30 ug/ml | | 373 | 110 | 2 | 2 | | E. LPS 100 ng/ml | 73 | |
| | | | 15 ug/ml | | 138 | 30 | 0 | 0 | | E. LPS 10 ng/ml | 34 | 55 |
| | | Plus Bartonella | Control | | 3 | 1 | 0 | 2 | Plus Bartonella | Control | 0 | 0 |
| | | | 30 ug/ml | | 227 | 76 | 2 | 1 | | E. LPS 100 ng/ml | 14 | 13 |
| | | | 15 ug/ml | | 53 | 36 | 2 | 1 | | E. LPS 10 ng/ml | 1 | 1 |
| IL-6 pg/ml | Donor 1 | Alone | Control | | 0 | 0 | 0 | 0 | Alone | Control | 0 | 0 |
| | | | 30 ug/ml | | 866 | 923 | 0 | 0 | | E. LPS 100 ng/ml | 2488 | 2141 |
| | | | 15 ug/ml | | 777 | 797 | 0 | 0 | | E. LPS 10 ng/ml | 1718 | 1444 |
| | | Plus Bartonella | Control | | 0 | 0 | 0 | 0 | Plus Bartonella | Control | 0 | 0 |
| | | | 30 ug/ml | | 873 | 930 | 0 | 0 | | E. LPS 100 ng/ml | 2398 | 2132 |
| | | | 15 ug/ml | | 898 | 800 | 0 | 0 | | E. LPS 10 ng/ml | 1605 | 1623 |
| | Donor 2 | Alone | Control | | 36 | 0 | 0 | 0 | Alone | Control | 0 | 0 |
| | | | 30 ug/ml | | 1939 | 1829 | 0 | 0 | | E. LPS 100 ng/ml | 5205 | |
| | | | 15 ug/ml | | 1928 | 1319 | 0 | 0 | | E. LPS 10 ng/ml | 4447 | 4828 |
| | | Plus Bartonella | Control | | 35 | 0 | 0 | 0 | Plus Bartonella | Control | 0 | 0 |
| | | | 30 ug/ml | | 1128 | 1054 | 0 | 0 | | E. LPS 100 ng/ml | 2812 | 2908 |
| | | | 15 ug/ml | | 183 | 112 | 0 | 0 | | E. LPS 10 ng/ml | 772 | 658 |
| TNF-a pg/ml | Donor 1 | Alone | Control | | 7 | 0 | 7 | 0 | Alone | Control | 7 | 0 |
| | | | 30 ug/ml | | 596 | 629 | 174 | 18 | | E. LPS 100 ng/ml | 901 | |
| | | | 15 ug/ml | | 520 | 386 | 89 | 101 | | E. LPS 10 ng/ml | 776 | 724 |
| | | Plus Bartonella | Control | | 0 | 6 | 0 | 6 | Plus Bartonella | Control | 0 | 6 |
| | | | 30 ug/ml | | 646 | 593 | 123 | 92 | | E. LPS 100 ng/ml | 442 | 516 |
| | | | 15 ug/ml | | 537 | 403 | 20 | 80 | | E. LPS 10 ng/ml | 274 | 256 |

Figure 6A:
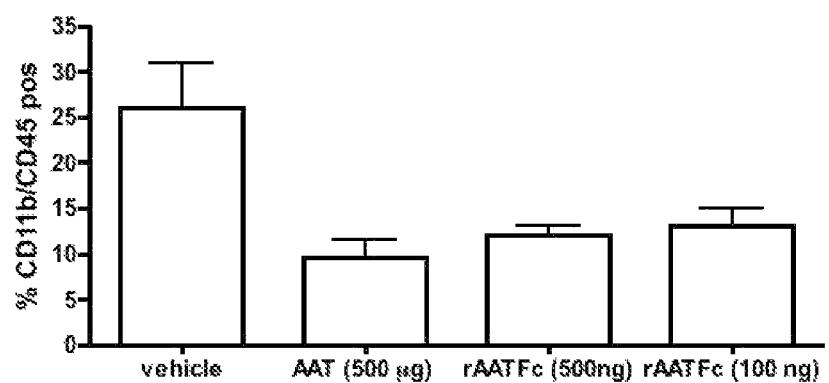
FIGS. 6A-6C represent percent expression of CD11b/CD45 positive cells and percent of TLR4 and TLR2 expression in the presence of plasma-derived AAT versus AAT fusion molecule, Fc-AAT2, and found that about 100 to about 1000 fold less recombinant AAT (Fc-AAT2) had the same inhibitory effect on these deleterious molecules. For example, Toll-like Receptor 4 at either 500 or 100 ng as effective as 500 µg of plasma-derived AAT (see FIG. 6A).
Figure 6B:
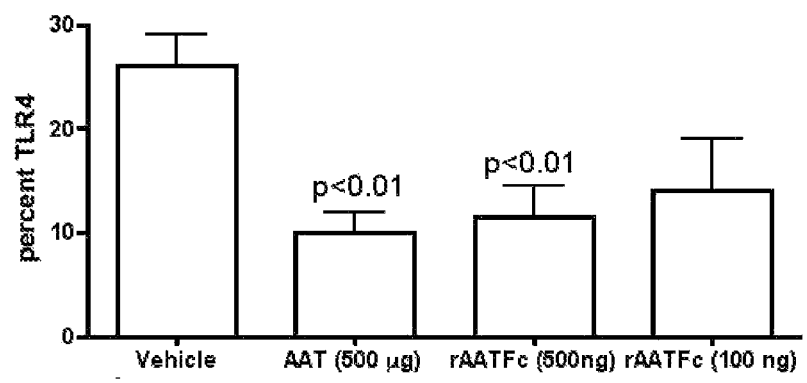
Figure 6C:
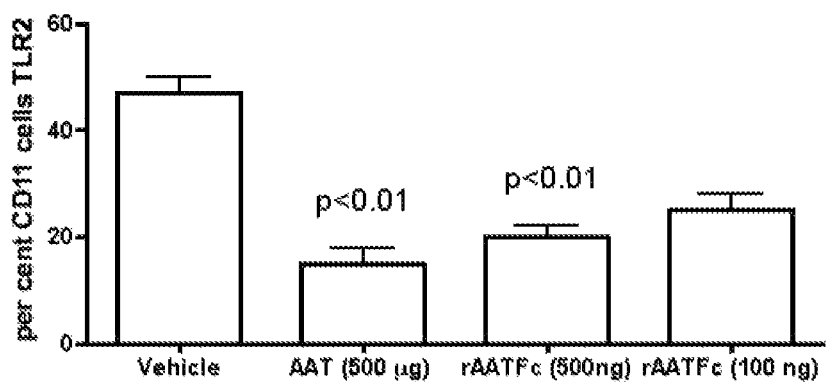

FIGS. 6A-6C represent percent expression of CD11b/CD45 positive cells and percent TLR4 and TLR2 expression in the presence of plasma-derived AAT versus Fc-AAT2 and found that about 100 to about 1000 fold less recombinant AAT (Fc-AAT2) had the same inhibitory effect on these deleterious molecules. For example, Toll-like Receptor 4 at either 500 or 100 ng as effective as 500 µg of plasma-derived AAT (see FIG. 6A).

Example 6

Gout Model

Effect of recombinant Fc-AAT on IL-1β production in PBMC stimulated with monosodium urate crystals, a model for gouty arthritis. Effects of Fc-AAT induced IL-1β production in PBMC stimulated with monosodium urate crystals (MSU) together with C-18 (C18) fatty acids were analyzed using a previously described gout model.

IL-1β Production in In Vivo Inflammation Study

Figure 7A:
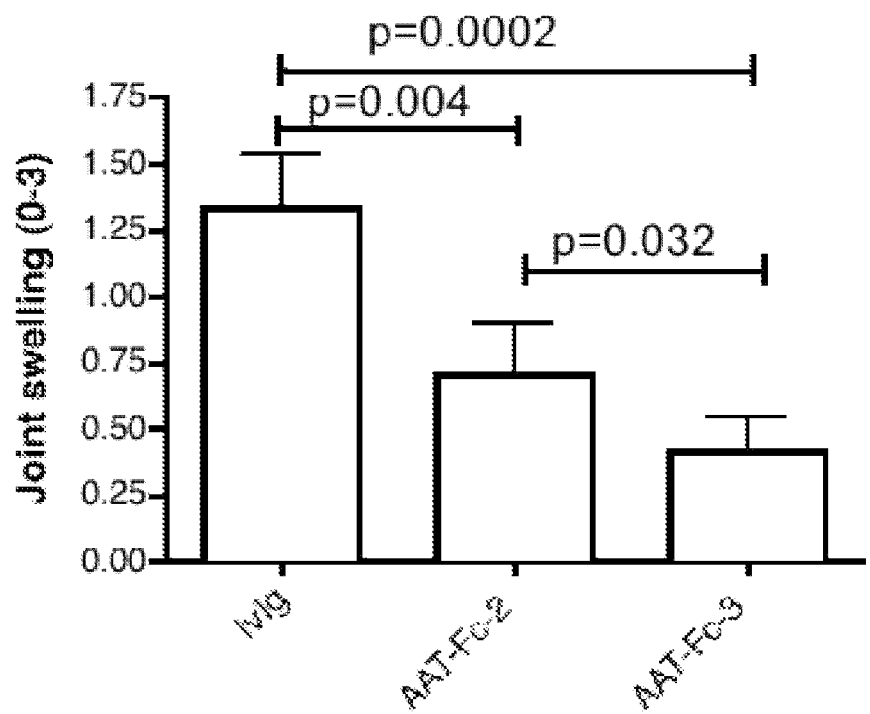
FIGS. 7A-7D represent histogram data plots representing an in vivo Gouty arthritis assay in mice related to effects of fusion molecules of some embodiments disclosed herein on joint swelling (7A comparing two Fc AAT fusion molecules, 7C an Fc AAT fusion molecule versus controls) and IL-6 production in the same model (7B) as well as effects of exposure to an Fc AAT fusion molecule and inhibition of IL-1β over time (7D, from 24 to 72 hours).
Figure 7B:
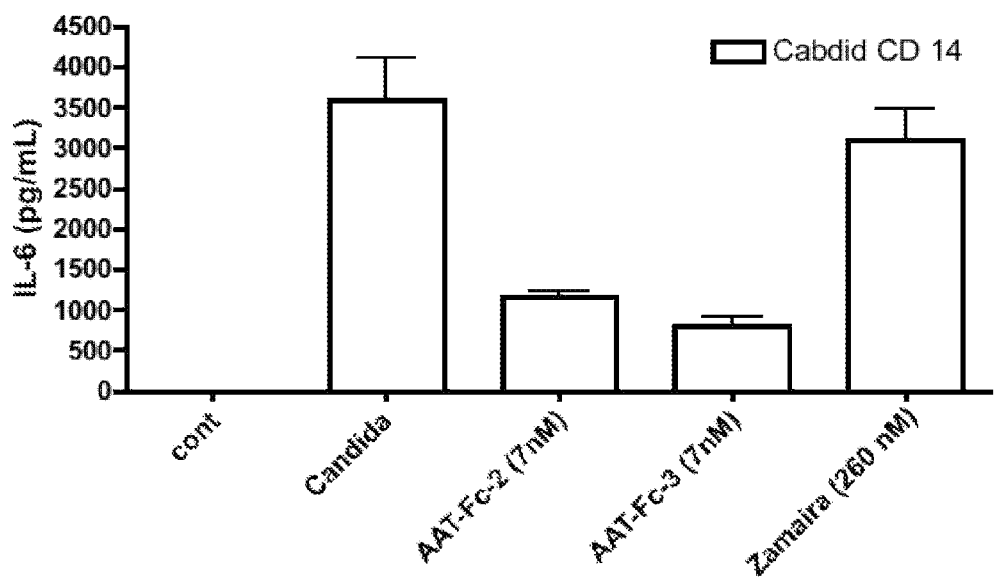

Experiments were performed using the mouse gout (Gouty arthritis) model to compare in vivo, effects of Fc-AAT2 (IgG1) versus Fc-AAT3 (hinge deletion) (see FIG. 7A). It was hypothesized that Fc-AAT3 (and other Fc having a deleted hinge) would have superior results in vivo to Fc-AAT2 (intact hinge of IgG1). First, protein concentrations of AAT-Fc-2 and AAT-Fc-3 were determined. Mice were weighed and dosing adjusted to 2.0 mg/kg. After 2 hours, MSU C16.0 was injected intra-articularly. After 4 hours, mice were euthanized and joints scored. Synovial tissues were homogenized for cytokine levels (e.g. 144,000 g/L=1 mole; 144,000 mg/mL=1M:144 mg/mL=1 mM:144 µg/mL=1 µM: 14 µg/mL=100 nM) Molecular weight of plasma-derived AAT=42,000 (less glycosylations) 42 micrograms/mL of plasma-derived AAT is 240 nM and the molecular weight of AAT-Fc=144,000 (less glycosylations) 14 micrograms/mL AAT-Fc is 7 nM. Additional studies concerned assessment of IL-6 in the presence or absence of AAT where a commercial formula (Zemaira™) was compared to Fc-AAT2 and Fc-AAT3 (FIG. 7B). It was noted that using an in vitro model of human blood monocyte cells induced by *Candida albicans* that IL-6 expression was dramatically reduced. Both recombinant formulations outperformed native AAT formulations (Zemaira™) (See FIG. 7B). The commercial formulation failed to significantly inhibit IL-6 expression compared to the Fc-AAT2 and Fc-AAT3.

Figure 7C:
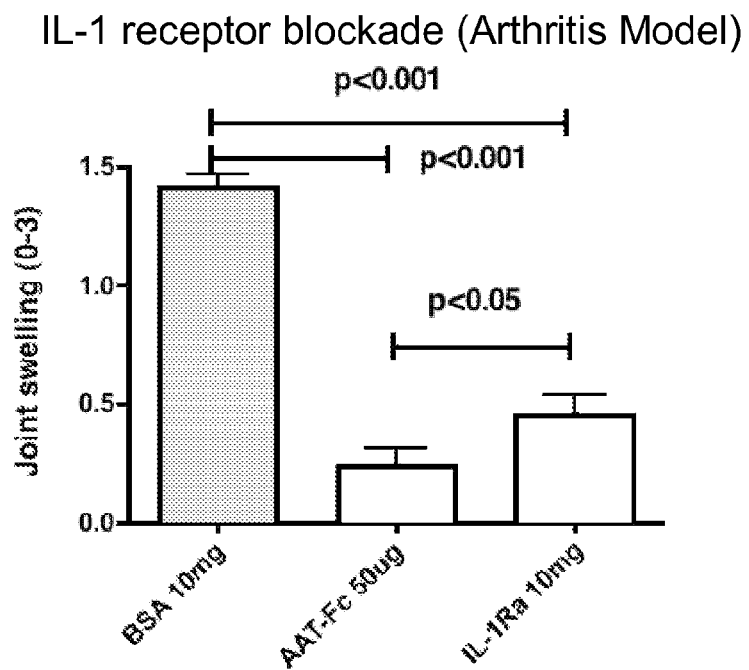
Figure 7D:
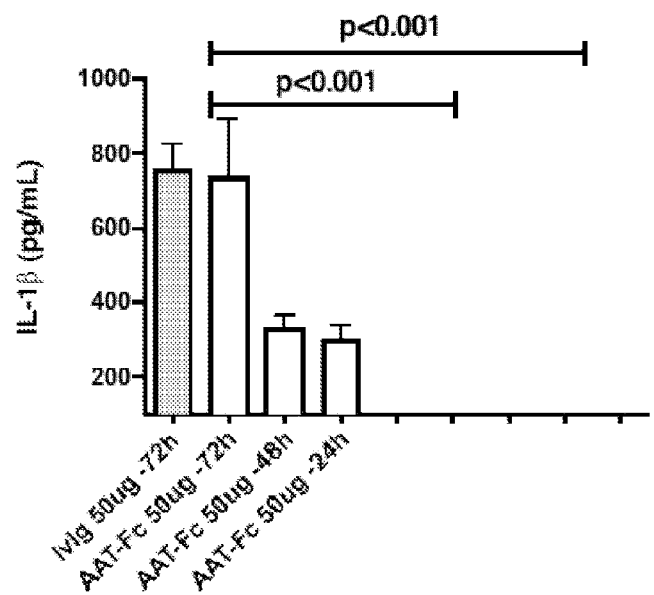

Another experiment was performed using a gout mouse model to observe total IL-1 receptor blockade (see FIG. 7C). In yet another exemplary method, a time course analysis of Fc-AAT2 (clone 2) effect on levels of IL-13 was assessed. The time course was between 0 to 72 hours after exposure to various amounts of recombinant AAT. A time-course study of Fc-AAT2 was performed where the fusion molecule was introduced as a pretreatment intraperitoneally before instillation of monosodium urate (NSU) crystals into the knee joint. About 4 hours after instillation, the mice were sacrificed and the knee joint excised and cultured. After about 2 hours in culture, IL-1β was measured in supernatants of the cultures (N=10 per group). The data is illustrated in FIG. 7D where IL-1β was inhibited with the pretreatment of FcAAT2 for greater than 48 hours thus supporting a role for novel recombinants in the inhibition of IL-1β adverse effects and as a potential treatment in Gout patients. See for example experimental procedures of Joosten et al, Arthritis Rheum. 2010 November; 62(11): 3237-3248.

Methods in brief: joint inflammation can be induced by intraarticular injection (i.a.) of a dose-range highly pure MSU (30-300 μg), 200 μM C18.0, MSU/C18.0 (300 μg/200 μM) or 25 μg SCW (rhamnose content) in 10 μl of PBS into the right knee joint of naïve mice. 4 hour after i.a. injection, joint swelling was determined, synovial tissue was isolated and knee joints were removed for histology. Joint swelling measurement can be measured by either macroscopic scoring or by the 99mTc uptake method. Macroscopic joint swelling is scored on a scale ranging from 0-3. After the skin is removed the knee joint was scored, 0=no swelling and 3=severe swelling. 99 mT cupcake method was performed as previously described (21,22). Joint swelling is expressed as the ratio of the 99mTc uptake in the inflamed over the control joint (left knee joint). All values exceeding 1.10 are assigned as joint swelling.

Example 7

Myocardial Infarction Model

Figure 8:
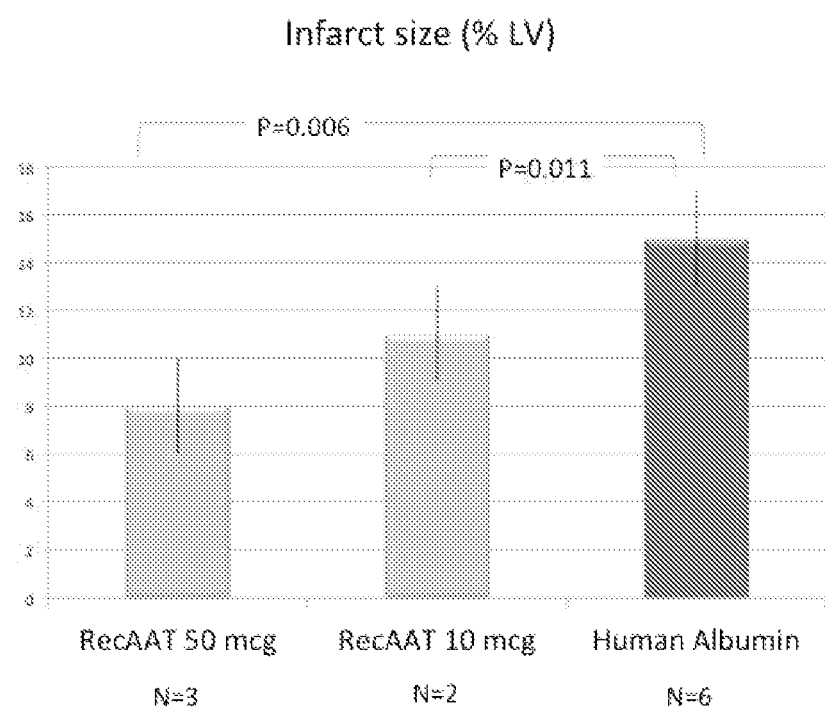
FIG. 8 represents a histogram plot representing infarct size in the presence or absence of Fc-AAT2 (recombinant AAT at 2 concentrations) after a cardiac event using a myocardial infarction-induced mouse model where the mouse undergoes ischemia reperfusion.

In another exemplary method, a myocardial infarction mouse model was used to assess the ability of Fc-AAT fusion molecules to inhibit cardiac remodeling, reduce infarct size as previously demonstrated for plasma-derived AAT models (data not shown). The experimental model of AMI (acute myocardial infarction) due to transient myocardial ischemia (30 min) simulates the clinical setting of patients with reperfused AMI. The mice experience an ischemic damage followed by a reperfusion injury. The average infarct size is 15-20% of the left ventricle. The mice develop a mild form of dilated cardiomyopathy with dilatation and dysfunction of the left ventricle. In this model of AMI, an increase in the LVEDD and LVESD, and a fall in LVFS (p<0.05 vs Sham for all comparisons) at 7 days was observed. It is demonstrated that at increasing concentrations of 10 or 50 microgram of Fc-AAT fusion molecules that infarct size measures as percent of left ventricle affected by infarct was significantly reduced at both concentrations (FIG. 8). This concentration is dramatically reduced compared to plasma-derived AAT formulations (approximately 100 times more were used in a comparable study, 2 milligrams intraperitoneally) (data not shown).

Another experimental model of AMI due to permanent coronary artery occlusion simulates a clinical setting of patients with non-reperfused large AMI. The mice experience a severe ischemic damage. The average infarct size is 25-35% of the left ventricle. The mice develop a severe form of dilated cardiomyopathy with dilatation and dysfunction of the left ventricle, and high mortality rate. This model also demonstrated that plasma derived AAT is effective at reducing the effects of an acute myocardial infarction.

Figure 9:
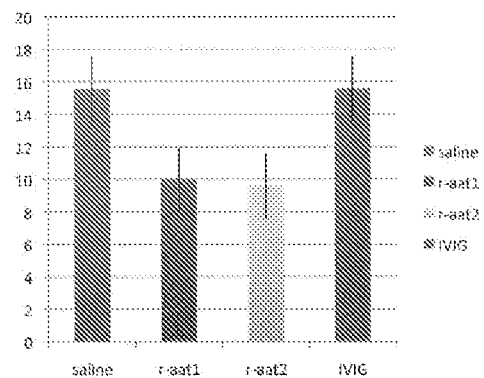
FIG. 9 represents a histogram plot representing infarct size in the presence or absence of two Fc-AAT constructs, each having an intact AAT molecule linked to intact Fc (at the same concentration) after a cardiac event using a myocardial infarction-induced mouse model where the mouse undergoes ischemia reperfusion.

Further, as illustrated in FIG. 9 using another mouse model simulating a heart attack, Fc-AAT1 (clone 1) which was demonstrated to have no elastase activity and Fc-AAT2 (clone 2) demonstrated to have elastase inhibition were equally effective at reducing cardiac remodeling measured as infarct size. Both recombinant molecules were active as a single dose (50 micrograms/mouse) compared to 5 days of 2 mg/mouse of other agents (IVIG). It is proposed that Fc-AAT3 (clone3, without hinge of IGg1) will be even more effective in this in vivo model to reduce cardiac remodeling and other effects of ischemia reperfusion. Thus, these experiments support that fusion molecules disclosed here are effective at reducing the deleterious effects of ischemia-reperfusion injury and adverse cardiac conditions.

Fc-AAT fusion molecules limit ischemia-reperfusion damage and reduce infarct size.

Fc-AAT fusion molecules limit the cytokine release after ischemia-reperfusion.

plasma-derived AAT does not reduce infarct size in the non-reperfused AMI which suggests that AAT affects the inflammatory component related to reperfusion injury (data not shown) thus supporting a role for Fc-AAT fusion molecules for treatment of adverse cardiac conditions.

4) Fc-AAT Fusion Molecules Limit Adverse Cardiac Remodeling in Both Models of AMI Example 8

Figure 10:
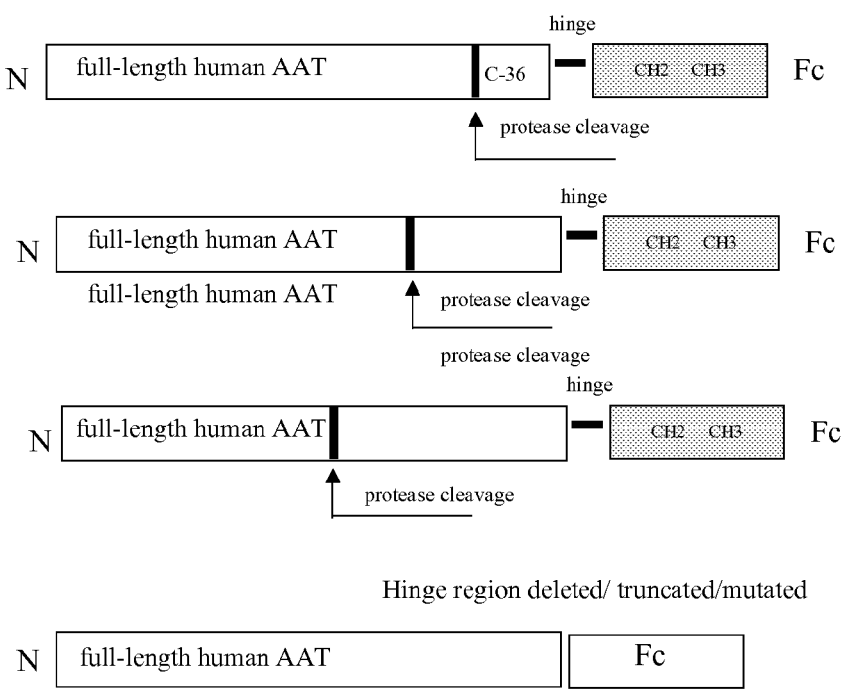
FIG. 10 illustrates schematics of Fc-AAT fusion molecules of certain embodiments of the present invention.

FIG. 10 illustrates some Fc-AAT fusion molecules contemplated herein where the hinge region is deleted, truncated or mutated.

Example 9

Colitis/IBD Model

As presented above, Fc-AAT3 both in vivo and in vitro inhibits the production of cytokines thus modulating deleterious effects of pro-inflammatory cytokines. It is thought that this data and previous studies of plasma-derived AAT in colitis/IBD models both support a role for Fc-AAT (hinge deleted) in the treatment of or prophylactic for inflammatory bowel diseases.

It has been demonstrated that plasma-derived AAT treatment attenuates loss of weight in DSS colitis model of mice, which is one of the most dependable indicators of inflammatory bowel disease activity in this model. In addition, there is significant reduction in cytokines secreted into the supernatant of colonic explants.

Mice can be with Fc-AAT (2 micrograms to 2 mg/day i.p.) in the DSS model compared to vehicle treated mice and control plasma-derived AAT formulations (2 mg/day). Mice will be weighed at various times and then sacrificed to assess body weight and assess decrease in colon shortening as observed for native AAT. It is hypothesized that the supportive evidence presented herein will be further substantiated by observations of decreased weight loss and colon shortening in the fusion molecule treated DSS colitis mice. Further, it expected that the concentration to see the same or similar results as plasma-derived AAT (positive control) will be about 10- and up to 1000-fold less for the fusion molecule. In addition cytokine production (e.g. IL-1, IL-6, MCP-1 and KC) by colonic explants will be assessed and compared to the control mice.

Example 10

A mouse model for assessing glucose regulation in islet cell toxicity induced scenario will be used to assess Fc-AAT fusion molecules ability to reduce cellular transplant rejection and reduce for example, islet cell degradation as further supported by the previous observations that plasma-derived AAT is capable of protecting islet cells from degradation. In certain methods, a standard toxin can be used on a mouse model islet beta cell toxicity assay the toxin streptozotozin (STZ). As previously illustrated, a commercially available source of AAT (Aralast™) demonstrated protection in STZ-induced diabetes to protect islet cells. The previous study used a single dose of STZ to induce beta cell death. After two injections of STZ, mice become diabetic (blood sugar rises to over 400 mg/dL). This double dose is used as an acceptable model of immune destruction of the beta cells. Fc-AAT fusion molecules will be compared to plasma-derived AAT to assess protective effects on the islets. Either control (PBS), plasma-derived AAT (commercially available) or Fc-AAT (hinge intact and deleted at about 1 microgram or 10 times less per mouse) will be injected each day. It was previously observed that commercially available formulations of AAT reverse the adverse effects and preserve islet cell function. It is predicted that Fc-AAT (hinge deletion) will have superior effects compared to plasma-derived AAT and demonstrate less side effects than Fc-AAT without hinge deletion thus supporting the use of compositions disclosed herein to aid in cellular and organ transplantation to reduce organ rejection and preserve transplants.

Use of fusion molecules disclosed herein before, during and/or after transplantation are supported. In certain embodiments, Fc-AAT fusion molecules disclosed herein can be used to maintain a graft and/or reduce adverse effects of graft rejection such as GVHD.

Preliminary data also support that fusion molecules of Fc-AAT (hinge deletion) can be used to reduce or prevent the onset of diabetes by for example, protecting islet cells in a subject from adverse effects of inflammation and immune responses.

Example 11

Construction of truncated variants of Fc-AAT. In certain exemplary embodiments, protease cleavage of AAT can be a simple insertion of a protease site within the sequence of AAT, for example, tobacco mosaic virus protease. Insertion of the protease recognition site generates a truncated carboxyl end of AAT. This site is upstream from a Carboxy-36-terminal peptide of naturally-occurring AAT:

(SEQ. ID NO. 34)
SIPPEVKFNKPFVFLMIEQNTKSPLFMGKVVNPTQK

These truncated AAT molecules are capable of inhibiting LPS-induced IL-1β, IL-6 and TNFα. A bi-valent truncated fusion molecule will be superior to the peptide itself in terms of increased plasma half-life. Given the likelihood that natural AAT is found in the lipid rafts of the cell membrane, it would be unlikely that the insertion would be at the N-terminus but rather the C-terminus. Therefore, having the C-terminal 36 amino acids linked to Fc for a bi-valent structure will likely be more effective in the lipid rafts.

Cleavage of the Fc domain. The other cleavage site is that of the Fc itself, in order to remove the Fc fragment. This site generates monomeric AAT or truncated AAT. However, the enzyme for Fc-IgG1 differs from that of Fc-IgG2.

A fusion protein of the N-terminus. The construct of N-terminal AAT is a novel concept that is based on data showing the anti-inflammatory properties of AAT are independent of the elastase inhibition property. Thus using the N-terminal for an inframe construction facilitates the formation of a molecule with a bi-valent C-terminal. For each construct, the expression in CHO is essential as glycosylation is an important component of the molecule. Therefore, CHO cells will be used for the expression of wild-type as well as truncated AAT-Fc. Other examples include constructs linked at the carboxy terminus (e.g. Fc-AAT2 and Fc-AAT3)

Purification and assays of truncated AAT-Fc. In the case of the protease insertion site, the protease to cleave the molecule can be introduced first and then use Protein A to isolate only fragments. That would yield a near pure form of product. In certain methods, such as in the case of the Fc cleavage site, the molecule would be best purified on Protein A, add the Fc cleavage protease and then remove the Fc fragment on protein A leaving the remaining protein nearly pure.

Example 12

Effect of Fc-AAT on IL-1β-induced IL-17 in Type 2 Diabetes (T2D). Evidence demonstrates that immune system cells, especially monocytes of the PBMC fraction, play pro-inflammatory roles in type 2 diabetes (T2D). Monocytes from T2D patients hyper-produce key pro-inflammatory cytokines, including IL-1β. IL-1β is implicated in skewing of human T cells to the pro-inflammatory IL-17 production by T cells from T2D patients (compared to non-diabetic donors) is elevated constitutively and in response to stimuli. Effects of Fc-AAT (rec-AAT, rAAT) will be tested on production of IL-1β-induced IL-17 in PBMC as a model.

Generation of AAT $Tg^{wt}$ mice. The unique aspect of these mice that differs from the AAT Tg strain is the promoter. The new strain will have the chicken beta-actin global promoter and blood levels will be higher than those of the AAT Tg mice expressing AAT in the type 2 lung epithelial. Once generated, heterozygous mice (expressing one copy of wild-type AAT) will be subjected to in vivo challenge assays. a. Characterization of AAT $Tg^{wt}$ mice. Once there are heterozygous mice by DNA analysis, western blot assessment will be carried out using various tissues to examine steady state expression. These include histological examinations of the tissues. b. Assays on primary cells for cytokine production in vitro. Similar to humans, it is possible to study cytokines from PBMC of mice. The stimulants include all Toll Like Receptors (TLR) agonists, and the combination of IL-18 plus IL-12. c. cytokine responses in vivo following various challenges. LPS or heat-killed Staphylococcus epidermidis will be injected intraperitoneally and circulating cytokines will be measured at specific time intervals. Models of IL-18 plus IL-2 will also be tested. In this model, mice develop a wasting syndrome with hypothermia, colitis and hypoglycemia. In preliminary data, the AAT Tg mouse is resistant to this model. d. Effect on islet allograft rejection. Once demonstrated that the AAT $Tg^{wt}$ mice are resistant to TLR challenges, the mice will be assessed for islet allograft rejection and related studies on mouse islets.

Mutation and cloning of AAT without serine protease inhibitory activity (AAT $Tg^{mu}$). As previously demonstrated, mutation of a cysteine in human AAT results in a molecule without the ability to inhibit protease (listed as non-functional, in the table below). The AAT plasmid shown above will be mutated by standard PCR methods and the Cys will be replaced with Ala. The sequence will be confirmed. This has already been mutated where Cys in human AAT was inserted into an EBV-gene expression vector. When the wild-type AAT EBV-gene expression vector is injected using high pressure bolus into the tail vein of a wild-type mouse, the DNA enter hepatocytes and AAT is expressed in the liver and serum levels of AAT rise.

TABLE 3

| Reactive centre: engineered and natural variants | | | | | | | | | | |
|---|---|---|---|---|---|---|---|---|---|---|
| Serpin | P$_4$ | P$_3$ | P$_2$ | P$_1$ | P$_1$' | P$_2$' | P$_3$' | P$_4$' | P$_5$' | Inhibits | Oxidation |
| α$_1$-Antitrypsin | Ala | Ile | Pro | Met | Ser | Ile | Pro | Pro | Glu | elastase | + |
| Pittsburgh variant | Ala | Ile | Pro | Arg | Ser | Ile | Pro | Pro | Glu | thrombin | - |
| Val-recombinant | Ala | Ile | Pro | Val | Ser | Ile | Pro | Pro | Glu | elastase | - |
| Leu-recombinant | Ala | Ile | Pro | Leu | Ser | Ile | Pro | Pro | Glu | Cat G. elastase | - |
| P$_2$Cys-recombinant | Ala | Ile | Cys | Met | Ser | Ile | Pro | Pro | Glu | non-functional | |
| Ala-recombinant | Ala | Ile | Pro | Ala | Ser | Ile | Pro | Pro | Glu | elastase | - |
| Christchurch variant | Ala | Ile | Pro | Met | Ser | Ile | Pro | Pro | Lys | elastase | + |
| P$_3$-P$_3$'-recombinant | Ala | Ala | Gly | Arg | Ser | Leu | Asn | Pro | Glu | non-functional | |
| Antithrombin | Ile | Ala | Gly | Arg | Ser | Leu | Asn | Pro | Asn | thrombin | - |
| Denver variant* | Ile | Ala | Gly | Arg | Leu | Leu | Asn | Pro | Asn | non-functional | - |

Stephens, Thalley and Hirs (1985).

All of the COMPOSITIONS and METHODS disclosed and claimed herein may be made and executed without undue experimentation in light of the present disclosure. While the COMPOSITIONS and METHODS have been described in terms of preferred embodiments, it will be apparent to those of skill in the art that variation may be applied to the COMPOSITIONS and METHODS and in the steps or in the sequence of steps of the METHODS described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A nucleic acid construct encoding a fusion polypeptide represented by SEQ ID NO: 49, SEQ ID NO: 56, SEQ ID NO: 57, or SEQ ID NO: 58.

2. A nucleic acid construct encoding the fusion polypeptide represented by SEQ ID NO: 49.

3. A composition comprising a fusion polypeptide represented by SEQ ID NO: 49, SEQ ID NO: 56, SEQ ID NO: 57 or SEQ ID NO: 58 and a pharmaceutically acceptable carrier.

4. A vector comprising the nucleic acid construct of claim 1.

5. An isolated preparation of inclusion bodies comprising a fusion polypeptide represented by SEQ ID NO: 49, SEQ ID NO: 56, SEQ ID NO: 57 or SEQ ID NO: 58.

6. A nucleic acid construct encoding a fusion polypeptide represented by SEQ ID NO:56.

7. The composition of claim 3, wherein the fusion polypeptide is represented by SEQ ID NO: 49.

8. A vector comprising the nucleic acid construct of claim 2.

9. The isolated preparation of inclusion bodies of claim 5, wherein the fusion polypeptide is represented by SEQ ID NO: 49.

10. The composition of claim 3, wherein the fusion polypeptide is represented by SEQ ID NO: 56.

11. A vector comprising the nucleic acid construct of claim 6.

12. The isolated preparation of inclusion bodies of claim 5, wherein the fusion polypeptide is represented by SEQ ID NO: 56.

13. A nucleic acid construct encoding the fusion polypeptide represented by SEQ ID NO: 57.

14. The composition of claim 3, wherein the fusion polypeptide is represented by SEQ ID NO: 57.

15. A vector comprising the nucleic acid construct of claim 13.

16. The isolated preparation of inclusion bodies of claim 5, wherein the fusion polypeptide is represented by SEQ ID NO: 57.

17. A nucleic acid construct encoding a fusion polypeptide represented by SEQ ID NO: 58.

18. The composition of claim 3, wherein the fusion polypeptide is represented by SEQ ID NO: 58.

19. A vector comprising the nucleic acid construct of claim 17.

20. The isolated preparation of inclusion bodies of claim 5, wherein the fusion polypeptide is represented by SEQ ID NO: 58.

* * * * *